(12) United States Patent
Ramaci

(10) Patent No.: US 10,580,284 B2
(45) Date of Patent: Mar. 3, 2020

(54) WEARABLE INTERACTIVE NOTIFICATION DEVICE AND INTERACTIVE NOTIFICATION SYSTEM

(71) Applicant: ELEMENTS OF GENIUS, INC., Isle of Palms, SC (US)

(72) Inventor: Jonathan E. Ramaci, Isle of Palms, SC (US)

(73) Assignee: Elements of Genius, Inc., Mt. Pleasant, SC (US)

( * ) Notice: Subject to any disclaimer, the term of this patent is extended or adjusted under 35 U.S.C. 154(b) by 0 days.

(21) Appl. No.: 15/878,929

(22) Filed: Jan. 24, 2018

(65) Prior Publication Data

US 2018/0211509 A1 Jul. 26, 2018

Related U.S. Application Data

(60) Provisional application No. 62/450,825, filed on Jan. 26, 2017.

(51) Int. Cl.
*G08B 21/24* (2006.01)
*G08B 3/10* (2006.01)
(Continued)

(52) U.S. Cl.
CPC ............ *G08B 21/24* (2013.01); *A61J 7/0454* (2015.05); *A61J 7/0481* (2013.01); *G08B 3/10* (2013.01);
(Continued)

(58) Field of Classification Search
CPC . G08B 21/24; G08B 5/36; G08B 3/10; G08B 21/0446; G16H 20/10; G16H 40/67;
(Continued)

(56) References Cited

U.S. PATENT DOCUMENTS 6,075,755 A * 6/2000 Zarchan ................ A61J 7/0481
368/10
7,454,002 B1 11/2008 Gardner et al.
(Continued)

OTHER PUBLICATIONS

Ramaci, Jonathan E.; Invitation to Pay Additional Fees for PCT Application No. PCT/US2018/015011, filed Jan. 24, 2018, dated Mar. 8, 2018, 2 pgs.
(Continued)

*Primary Examiner* — Adnan Aziz
(74) *Attorney, Agent, or Firm* — Gregory Finch; Jana Meier; Finch Paolino, LLC

(57) ABSTRACT

A notification system includes a database network, the database network configured to store a medication schedule of a patient; a voice translation service in communication with the database network; and a notification device comprising a processor configured to wirelessly communicate with at least one of database network and the voice translation service, the processor contained in a housing, the housing configured for attachment to the patient, a portion of the housing comprising a display panel; and a memory in communication with the processor, wherein the memory stores executable instructions for causing the processor to provide a visual reminder, at the display panel, of a medication event in the patient's medication schedule, transmit to the voice translation service a voice signal corresponding to an utterance of the patient; and receive from the voice translation service a verbal response to the utterance.

20 Claims, 41 Drawing Sheets

(51) Int. Cl.
*G08B 5/36* (2006.01)
*A61J 7/04* (2006.01)
*G16H 20/10* (2018.01)
*G16H 40/67* (2018.01)
*G16H 80/00* (2018.01)
*G08B 21/04* (2006.01)

(52) U.S. Cl.
CPC .............. *G08B 5/36* (2013.01); *G16H 20/10* (2018.01); *G16H 40/67* (2018.01); *A61J 2200/30* (2013.01); *A61J 2205/70* (2013.01); *G08B 21/0446* (2013.01); *G16H 80/00* (2018.01)

(58) Field of Classification Search
CPC ....... G16H 80/00; A61J 7/0454; A61J 7/0481; A61J 2205/70; A61J 2200/30
See application file for complete search history.

(56) References Cited

U.S. PATENT DOCUMENTS

| | | | |
|---|---|---|---|
| 9,717,101 B1* | 7/2017 | Burnham | H04W 4/021 |
| 2005/0148890 A1 | 7/2005 | Hastings | |
| 2008/0238666 A1 | 10/2008 | Loncar | |
| 2008/0266118 A1* | 10/2008 | Pierson | A61B 5/0205 340/573.6 |
| 2009/0048868 A1 | 2/2009 | Portnoy et al. | |
| 2009/0187121 A1* | 7/2009 | Evans | A61B 5/1101 600/595 |
| 2009/0259728 A1* | 10/2009 | Berisford | G06Q 50/22 709/206 |
| 2009/0322513 A1* | 12/2009 | Hwang | A61B 5/02055 340/539.12 |
| 2011/0093296 A1* | 4/2011 | Klink | G16H 10/65 705/3 |
| 2013/0169431 A1* | 7/2013 | Alhuwaishel | A61J 7/0481 340/539.11 |
| 2013/0310658 A1* | 11/2013 | Ricks | A61B 5/1118 600/301 |
| 2014/0075431 A1 | 3/2014 | Kumar et al. | |
| 2014/0266787 A1* | 9/2014 | Tran | A61B 5/0022 340/870.07 |
| 2014/0372147 A1* | 12/2014 | White | G16H 40/20 705/3 |
| 2014/0375246 A1* | 12/2014 | Boysen, III | H02J 5/005 320/101 |
| 2014/0378786 A1* | 12/2014 | Hong | A61B 5/4866 600/301 |
| 2014/0379910 A1 | 12/2014 | Saxena | |
| 2015/0137972 A1* | 5/2015 | Nepo | G08B 25/016 340/539.13 |
| 2015/0269824 A1* | 9/2015 | Zhang | G08B 21/0438 340/539.12 |
| 2015/0269827 A1* | 9/2015 | Hopkins | H04W 4/90 340/539.12 |
| 2015/0317455 A1 | 11/2015 | Lehmann et al. | |
| 2016/0019360 A1* | 1/2016 | Pahwa | G06F 19/3418 705/3 |
| 2016/0042623 A1 | 2/2016 | Riley et al. | |
| 2016/0133160 A1* | 5/2016 | Packer | G16H 40/67 600/509 |
| 2016/0140308 A1 | 5/2016 | Ramsdell et al. | |
| 2016/0161985 A1 | 6/2016 | Zhang | |
| 2016/0328529 A1 | 11/2016 | Kalb et al. | |
| 2016/0342767 A1 | 11/2016 | Narasimhan et al. | |
| 2017/0213050 A1 | 7/2017 | Ramaci | |
| 2017/0308897 A1 | 10/2017 | Ramaci | |
| 2017/0344755 A9 | 11/2017 | Ramaci | |
| 2018/0325470 A1* | 11/2018 | Fountaine | H04W 4/90 |
| 2019/0147721 A1* | 5/2019 | Avitan | G08B 21/043 340/573.1 |

OTHER PUBLICATIONS

AARP, Inc.—American Association of Retired Persons; "2016 Health Innovation Frontiers", Copyright 2016, 23 pgs.
census.gov—United States Census Bureau; "An Aging World: 2015", Issued Mar. 2016, 175 pgs.
forbes.com; Article entitled: "Beyond Digital and What Many CMOs Should Be Considering Putting Into Their 2018 Strategic Plan", Nov. 1, 2017, 3 pgs.
nih.gov—National Institutes of Health; "World's older population grows dramatically", Mar. 28, 2016, 3 pgs.
Inernational search report, International application No. PCT/US18/15011. dated May 21, 2018. ISA/US, Alexandria, VA.

* cited by examiner

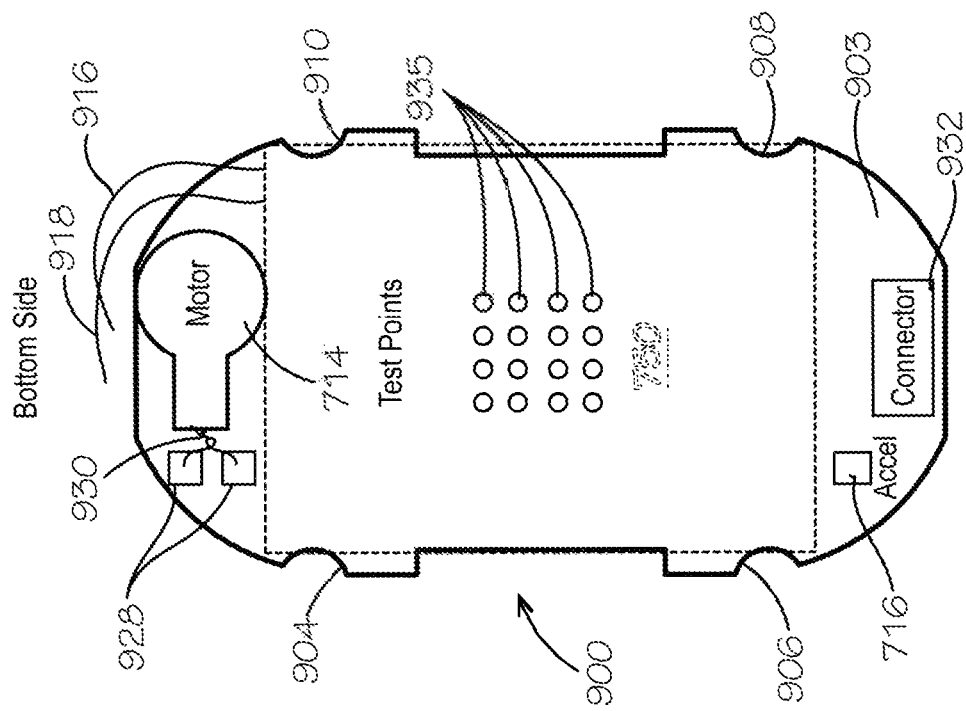
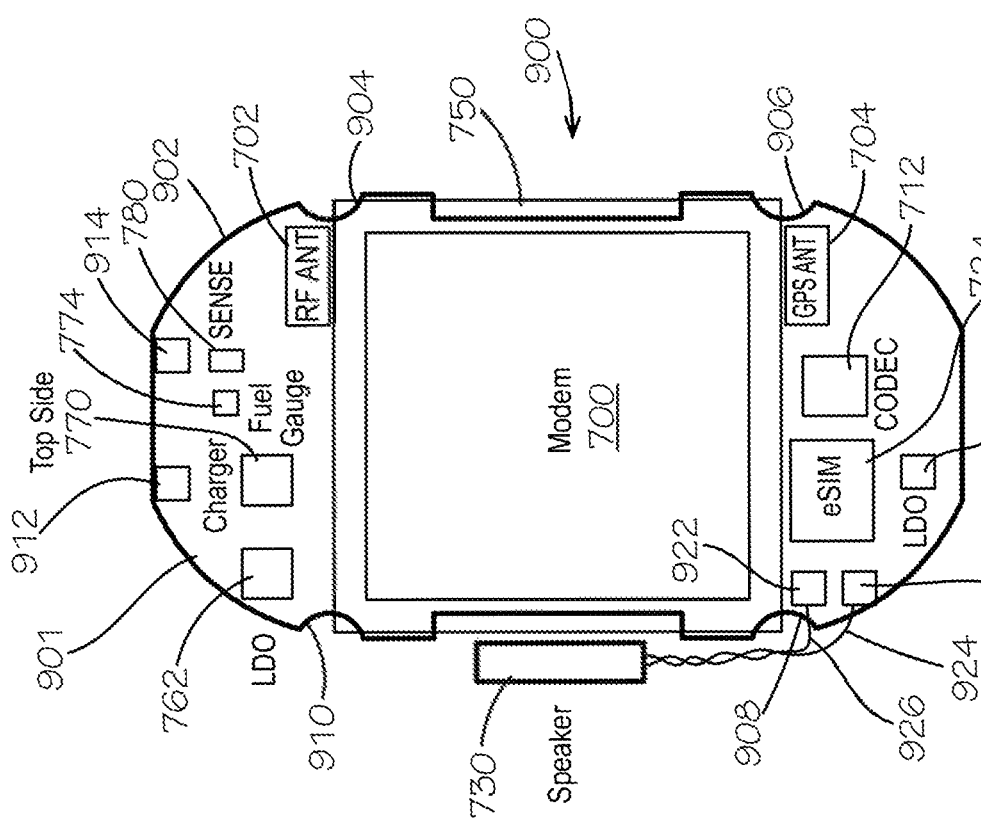
FIG. 9B
FIG. 9A

FIG. 14A  FIG. 14B

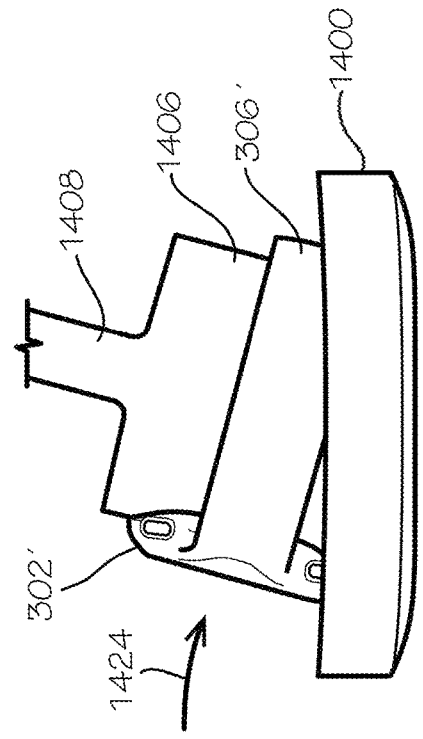
FIG. 15A
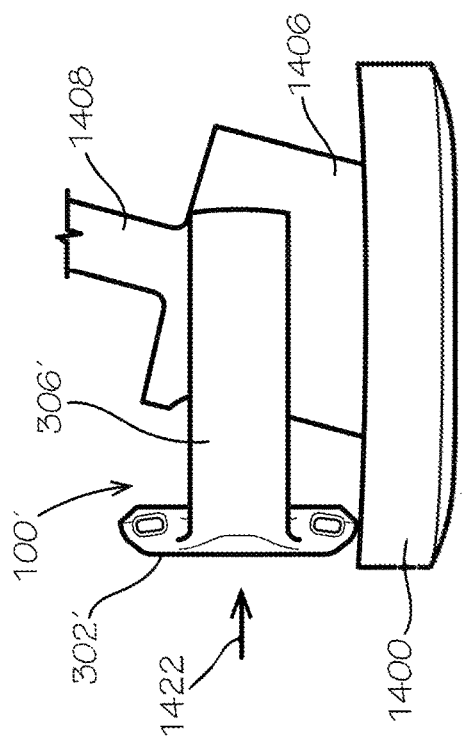
FIG. 15C
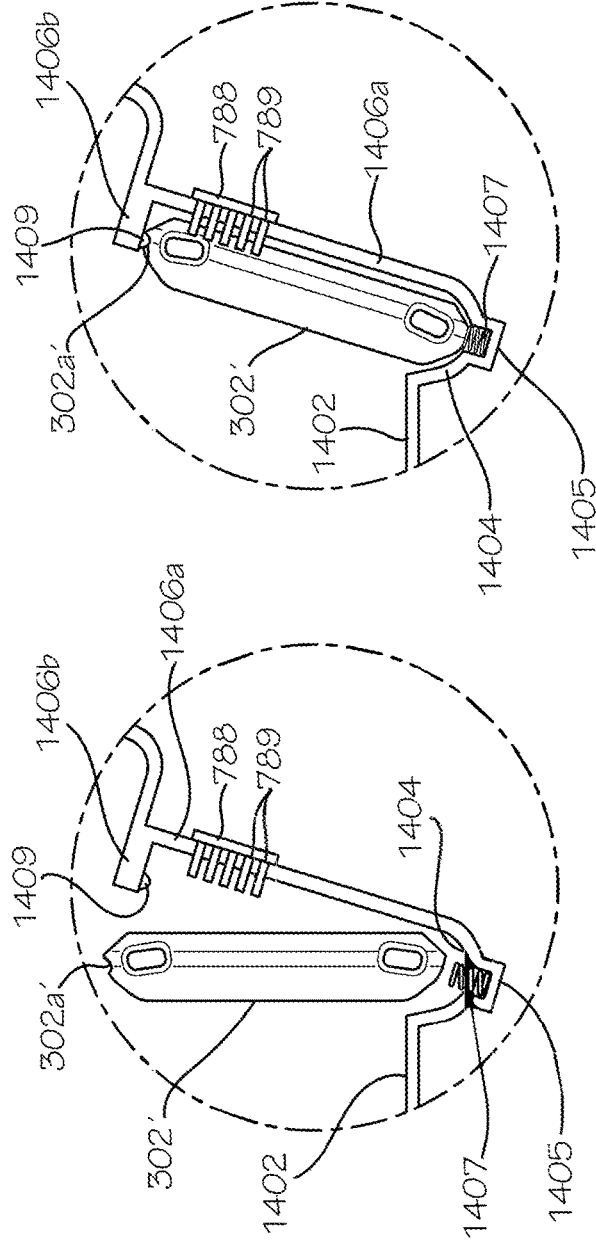
FIG. 15B
FIG. 15D

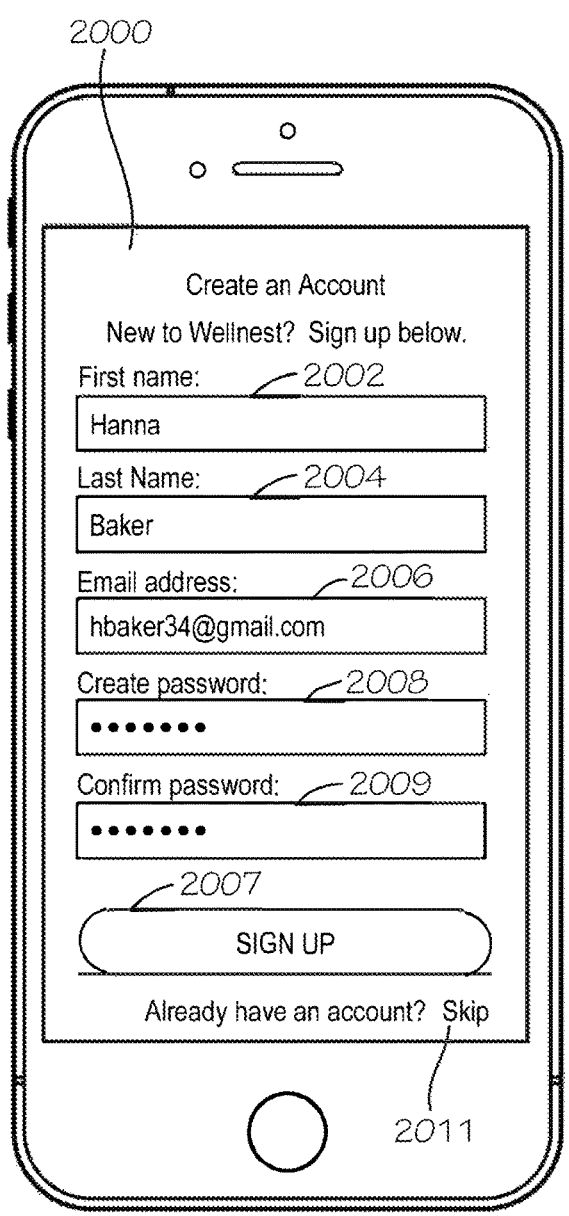
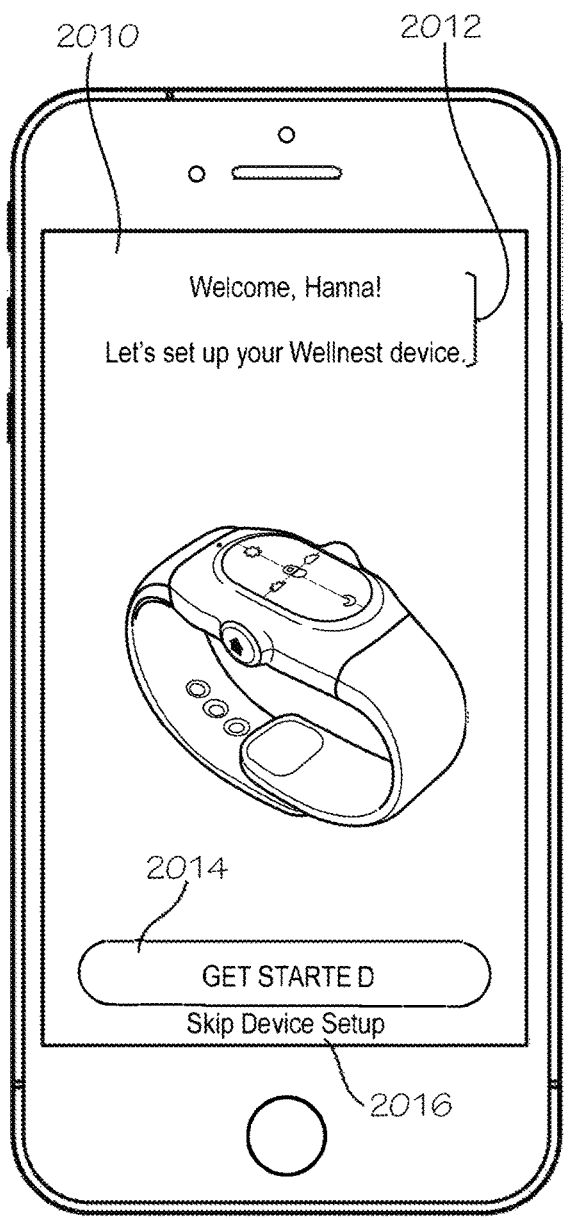
FIG. 20A  FIG. 20B

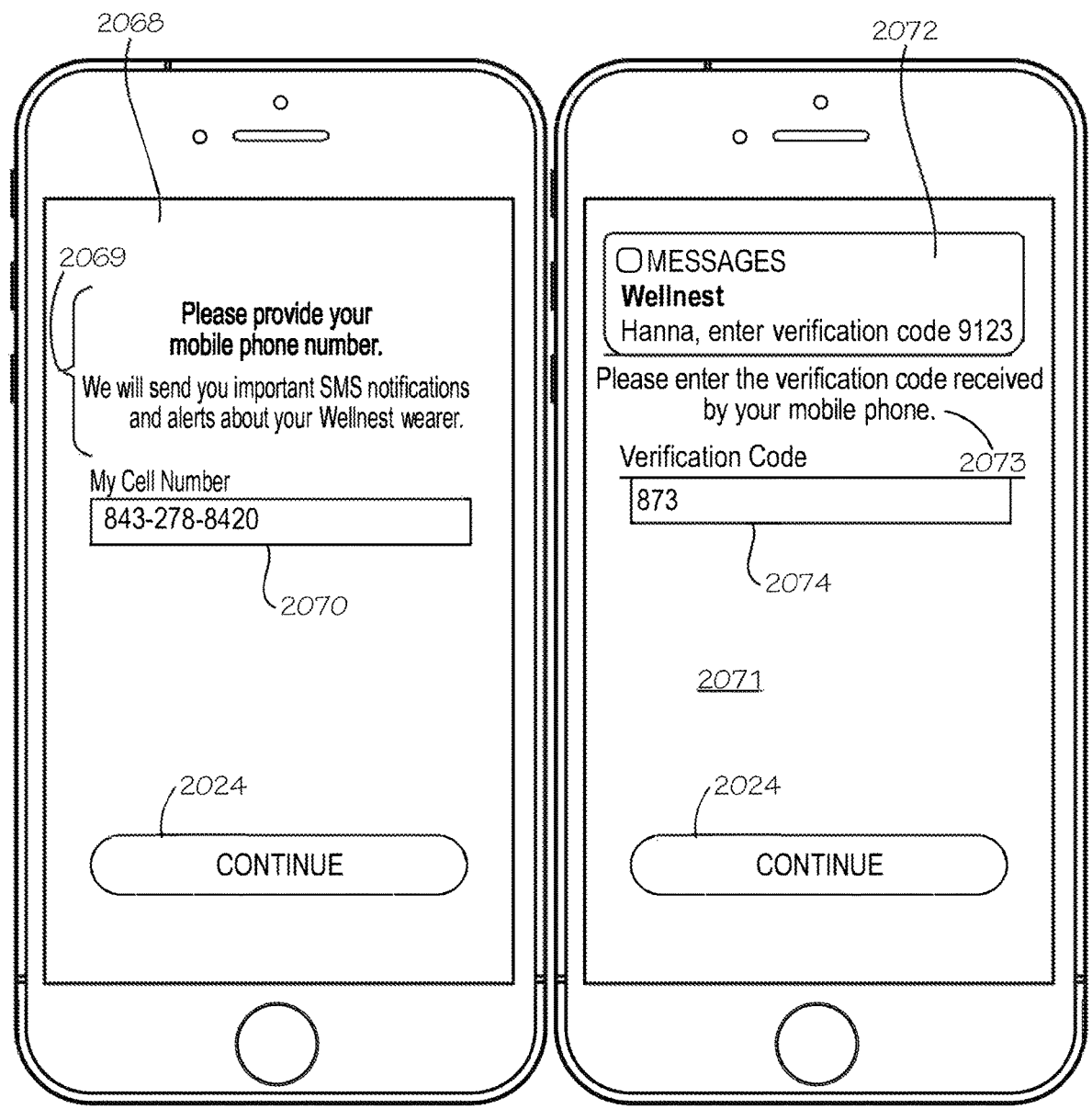
FIG. 20M  FIG. 20N

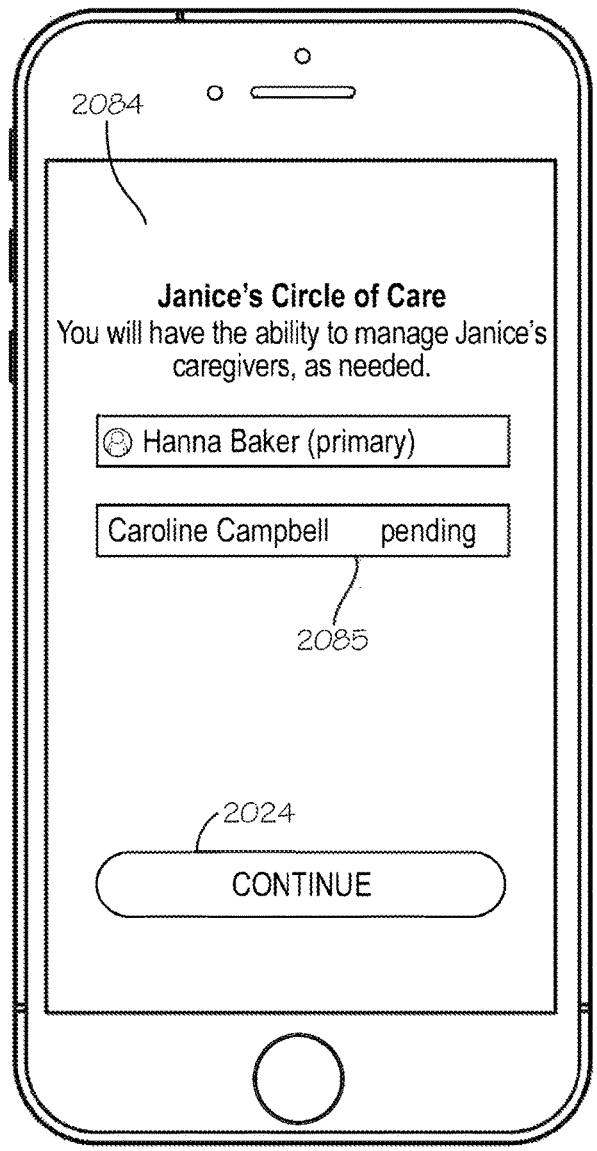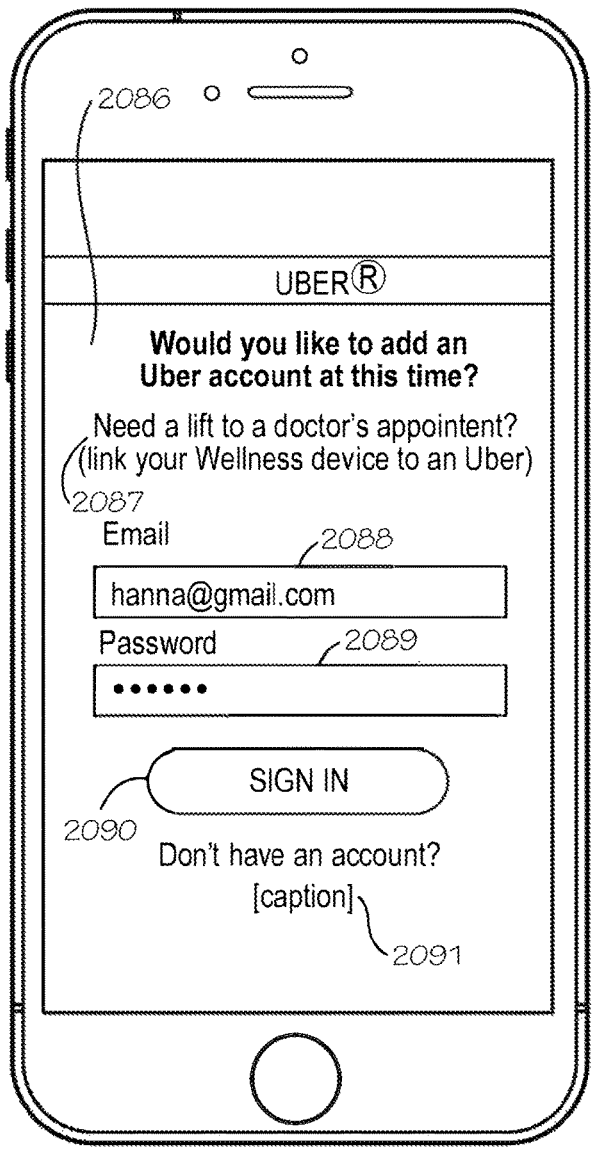
FIG. 20Q  FIG. 20R

WEARABLE INTERACTIVE NOTIFICATION DEVICE AND INTERACTIVE NOTIFICATION SYSTEM

CROSS-REFERENCE TO RELATED APPLICATION

This application claims the benefit of U.S. Provisional Patent Application Ser. No. 62/450,825, filed Jan. 26, 2017, the disclosure of which is hereby incorporated by reference herein in its entirety.

TECHNICAL FIELD

This disclosure relates to wearable interactive notification devices. More specifically, this disclosure relates to computing devices, methods, application software, automated voice recognition response devices, natural language understanding-processing methods, and communication channels for medicine reminders, location determination, and emergency notifications.

BACKGROUND

The world is undergoing significant growth in the percentage of its population aged 65 and older. For example, according to 2017 statistics published by the U.S. Census Bureau, U.S. "[r]esidents age 65 and over grew from 35.0 million in 2000, to 49.2 million in 2016, accounting for 12.4 percent and 15.2 percent of the total population, respectively." U.S. Census Bureau, *The Nation's Older Population Is Still Growing, Census Bureau Reports* (Jun. 22, 2017), https://www.census.gov/newsroom/press-releases/2017/cb17-100.html. A report published in March 2016 indicated that "the next 10 years will witness an increase of about 236 million people aged 65 and older throughout the world. Thereafter, from 2025 to 2050, the older population is projected to almost double to 1.6 billion globally, whereas the total population will grow by just 34 percent over the same period." He, Wan, Goodkind, Daniel, and Kowal, Paul: *An Aging World:* 2015: *International Population Reports*, U.S. Census Bureau and National Institutes of Health, at p. 1 (March 2016), https://www.census.gov/content/dam/Census/library/publications/2016/demo/p95-16-1.pdf.

According to a publication titled "2016 Health Innovation Frontiers," published by the American Association of Retired Persons ("AARP"), consumers aged 50 and older "[a]re managing moderate health problems with a light medication schedule," or "[a]re managing severe chronic conditions with a complex medication schedule." AARP, 2016 *Health Innovation Frontiers*, at p. 9 (2016), https://www.aarp.org/content/dam/aarp/home-and-family/personal-technology/2016/05/2016-Health-Innovation-Frontiers-Infographics-AARP.pdf. That publication mentions that traditional approaches include "[d]aily/weekly pillboxes, Post-It® reminders, and other fixes," as well as "medication therapy management." Id. That publication lists drawbacks with such approaches, namely that they are inconvenient, ineffective, "[n]o records for verification," "[h]igh reliance on call centers," and [h]igh costs with minimal benefits." Id.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

Applicant has perceived a need for a device and system that not only overcomes the drawbacks associated with aforementioned medication management methods, but that also provides for notifications to persons other than the patient during perceived emergency situations, and that presents even greater simplicity of use when compared to conventional reminder methods. Overcoming these drawbacks, and other benefits, are attendant to the wearable interactive notification device disclosed herein.

In an aspect of the present disclosure, a notification device comprises at least one processor contained in a housing, the housing configured for attachment to a user, a portion of the housing comprising a display panel, and a memory in communication with the at least one processor, the memory storing executable instructions for causing the at least one processor to provide a visual reminder, at the display panel, of a medication event in a medication schedule applicable to the user.

In another aspect of the present disclosure, a docking station comprises a docking station processor, an interface in communication with the docking station processor, the interface configured to engage an interactive notification device separate from the docking station, to receive data from the interactive notification device, and to supply current to a battery charger in the interactive notification device; and a display in communication with the interface and with the docking station processor, the display configured to show text indicating at least one changed state detected by the interactive notification device, the display further configured to assume an on state while the interactive notification device is engaged by the interface, and to assume an off state when the interactive notification device is disengaged from the interface.

In yet another aspect of the present disclosure, a wireless notification system comprises at least one database server, the at least one database server configured to store a medication schedule of a patient; at least one voice translation service in communication with the at least one database server; and a notification device comprising at least one processor configured to wirelessly communicate with at least one of the at least one database server and the at least one voice translation service, the at least one processor contained in a housing, the housing configured for attachment to the patient, a portion of the housing comprising a display panel; and a memory in communication with the at least one processor, wherein the memory stores executable instructions for causing the at least one processor to provide a visual reminder, at the display panel, of a medication event in the patient's medication schedule, transmit to the at least one voice translation service a voice signal corresponding to an utterance of the patient; and receive from the at least one voice translation service a verbal response to the utterance.

In yet another aspect of the present disclosure, a method of communicating an event concerning a patient to at least one other person, comprising the steps of building a list of at least one name, each name in the list identifying a person who has assented to become a member of a care group for the patient; storing, in a database within a database server, a cell phone number of each care group member; storing, in the database, patient identification data, the patent identification data comprising at least a name of the patient and a street address of the patient; storing, in the database, patient medication information, the patient medication information comprising at least, for each medication prescribed to the patient, a name of the medication, a dosage of the medication, a prescribed frequency for taking the medication, and at least one time of day for taking the medication; causing an interactive notification device designated for possession by the patient to issue a medication reminder, the medication reminder comprising at least one of a visual reminder on a display of the device, a verbal reminder broadcast through a speaker of the device, and a vibration reminder caused by activation of a vibration motor in the device, the medication reminder issuing to the patient upon an arrival of each time of day at which the patient is scheduled to take a medication according to the patient medication information; subsequent to initiation of the medication reminder to the patient, allowing a medication event period to elapse during which time the patient is provided with the opportunity to take scheduled medication and send a success signal indicating that the patient consumed the scheduled medication; and responsive to an elapse of the medication event period without receipt by the database of a success signal, causing the database server to send a text message to an entered cell phone number of each care group member, the text message indicating that the patient did not consume the scheduled medication during the medication event period.

Various implementations described in the present disclosure can comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations can be realized and obtained by means of the systems, methods, features particularly pointed out in the appended claims. These and other features will become more fully apparent from the following description and appended claims, or can be learned by the practice of such exemplary implementations as set forth hereinafter.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

FIGS. 9A and 9B are top and bottom views, respectively, of a printed circuit board for a wearable interactive notification device housing constructed according to an aspect of the present disclosure, showing placement of various hardware components.

FIGS. 14A-14C are front perspective, rear perspective, and side views, respectively, illustrating the docking of a wearable interactive notification device on a docking station constructed according to aspects of the present disclosure.

FIGS. 15A and 15B are side views of a wearable interactive notification device in a partially-docked position, with FIG. 15B isolating the wristband frame of a wearable interactive notification device in relation to a docking station interface and a retaining mechanism in the docking station of FIGS. 14A-14C.

FIGS. 15C and 15D are side views of the wearable interactive notification device of FIGS. 15C and 15D in a fully-docked position, with FIG. 15D isolating the wristband frame of the wearable interactive notification device in relation to the same docking station interface and retaining mechanism of FIGS. 15A and 15B.

DETAILED DESCRIPTION

Figure 1:
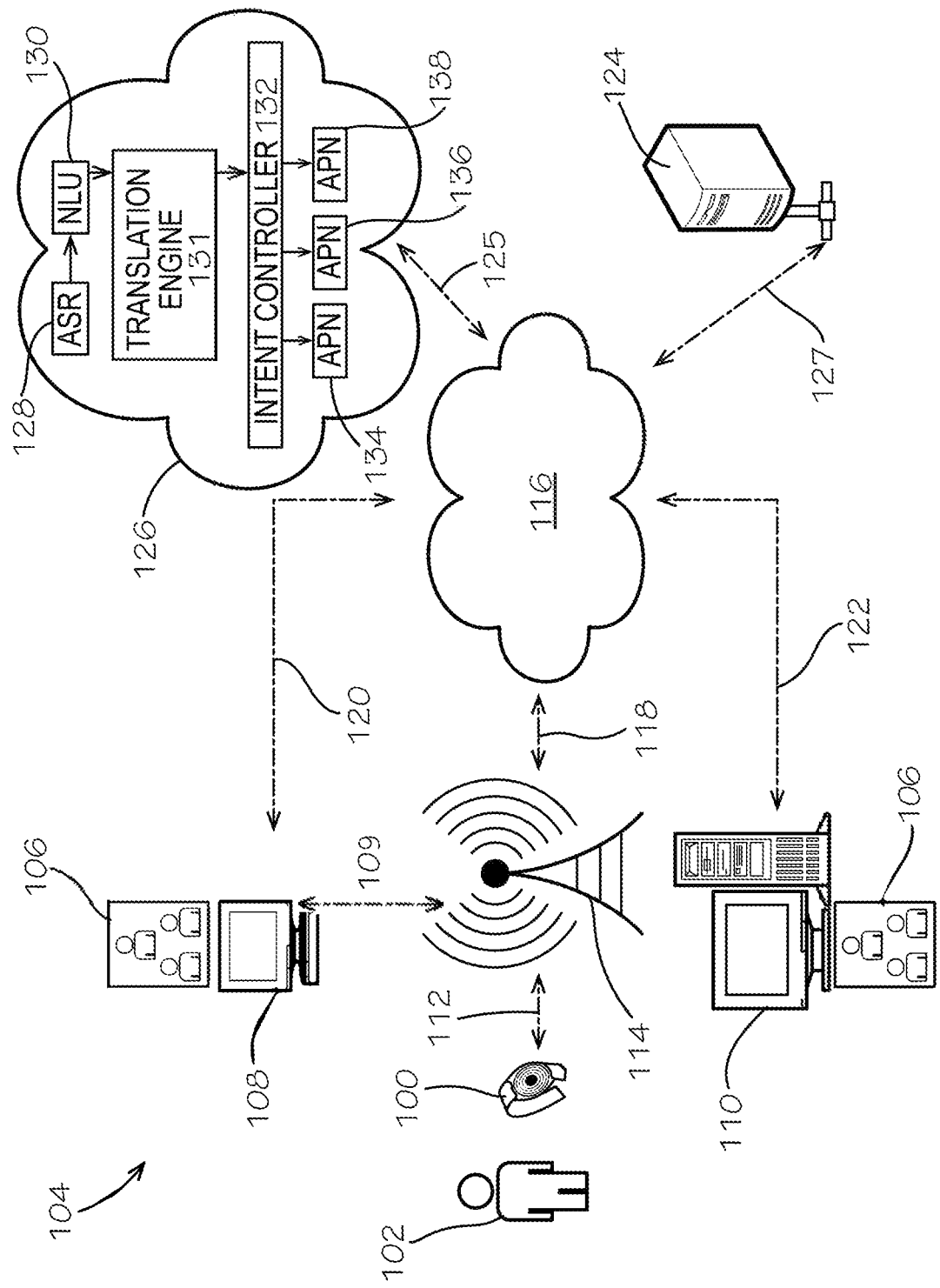
FIG. 1 is a block diagram depicting a wearable interactive notification device of a patient, the wearable interactive notification device operating in an exemplary interactive notification system according to aspects of the present disclosure.

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to a quantity of one of a particular element can comprise two or more such elements unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or substantially," it will be understood that the particular value forms another aspect. It will be further understood that the endpoints of each of the ranges are significant both in relation to the other endpoint, and independently of the other endpoint.

For purposes of the present disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list.

To simplify the description of various elements disclosed herein, the conventions of "top," "bottom," "side," "upper," "lower," "horizontal," and/or "vertical" may be referenced. Unless stated otherwise, "top" describes that side of the system or component that is facing upward and "bottom" is that side of the system or component that is opposite or distal the top of the system or component and is facing downward. Unless stated otherwise, "side" describes that an end or direction of the system or component facing in horizontal direction. "Horizontal" or "horizontal orientation" describes that which is in a plane aligned with the horizon. "Vertical" or "vertical orientation" describes that which is in a plane that is angled at 90 degrees to the horizontal.

Overview of Interactive Notification System

FIG. 1 is a block diagram depicting an exemplary interactive notification system 104 that includes a wearable interactive notification device 100 of a patient 102 In various aspects of the present disclosure, "wearable" means that the interactive notification device 100 can be temporarily attached to the body of a human being such that the human being can move (by either walking or undergoing motion with the assistance of a wheelchair or scooter) with the device 100 attached, without the interactive notification device 100 impeding the motion of the human being. In various aspects of the present disclosure, "wearable" more particularly means that the interactive notification device 100 can be temporarily attached to an appendage of a human being, such as an upper arm, without the aforementioned impeding of motion. In still other aspects of the present disclosure, "wearable" even more particularly means that the interactive notification device 100 can be temporarily attached to a human being's wrist, without the aforementioned impeding of motion, such that a display is visible to the human being upon a downward glance toward the wrist on which the interactive notification device 100 is worn. Although the specific embodiments are discussed later herein with reference to the wearable interactive notification device 100 temporarily attached about a wrist of the patient 102, such an example of a temporary attachment to the patient 102 is for illustrative purposes only and is not meant to be limiting. The interactive notification system 104 is configured to permit the patient 102 to wirelessly interact with a care group 106 comprising one or more of a healthcare provider (such as a physician or a nurse), a family member (i.e., a relative of the patient 102), a caretaker (i.e., someone, other than a healthcare provider or family member, who provides services promoting the well-being of the patient 102), and the like. As used herein, "user" is intended to refer to any individual who may legally access the interactive notification system 104, to include the patient 102, one or more members of the patient's 102's care group 106, and the like. A user can access the interactive notification system 104 using a portable computing device 108 (which can be, for example, a cell phone, a tablet, or a laptop computer) or a stationary computing device 110 (which can be, for example, a desktop computer residing at a facility of the patient's healthcare provider). The wearable interactive notification device 100 communicates with other elements of the interactive notification system 104 via a communication link 112 to at least one cellular communication network 114 which, in turn, communicates with a cloud 116 (described below) via a communication link 118. Thus, the wearable interactive notification device 100 can access the cloud 116 via the communication links 112 and 118.

As explained with regard to cloud computing generally in U.S. Patent Application Publication No. 2014/0379910 to Saxena et al., cloud 116 can include "a collection of hardware and software that forms a shared pool of configurable computing resources (e.g., networks, servers, storage, applications, services, etc.), which can be suitably provisioned to provide on-demand self-service, network access, resource pooling, elasticity and measured service, among other features." Cloud 116 may be deployed as a private cloud (e.g., infrastructure operated by a single enterprise/organization), community cloud (e.g., infrastructure shared by several organizations to support a specific community that has shared concerns), public cloud (e.g., infrastructure made available to the general public, such as the Internet), or a suitable combination of two or more disparate types of clouds. In this description, "cloud computing" is defined as a model for enabling on-demand network access to a shared pool of configurable computing resources (e.g., networks, servers, storage, applications, and services). As stated in U.S. Patent Application Publication No. 2014/0075431 to Kumar et al: "Generally, a cloud computing model enables some of those responsibilities which previously may have been provided by an organization's own information technology department, to instead be delivered as service layers within a cloud environment, for use by consumers (either within or external to the organization, according to the cloud's public/private nature)." As further explained in the aforementioned Kumar et al. patent application, a cloud computing model can take the form of various service models such as, for example, Software as a Service ("SaaS"), "in which consumers use software applications that are running upon a cloud infrastructure, while a SaaS provider manages or controls the underlying cloud infrastructure and applications," and Platform as a Service ("PaaS"), "in which consumers can use software programming languages and development tools supported by a PaaS provider to develop, deploy, and otherwise control their own applications, while the PaaS provider manages or controls other aspects of the cloud environment (i.e., everything below the run-time execution environment)." The definition of "cloud computing" is not limited to any of the other numerous advantages that can be obtained from such models when properly deployed.

Still referring to FIG. 1, the portable computing device 108 and the stationary computing device 110 can communicate with the cloud 116 via respective communication links 120 and 122, and portable computing device 108 can additionally communicate with the cellular communication network 114 via a communication link 109. Additionally, a database server 124 and a voice recognition service 126 can communicate with the cloud 116 via respective communication links 127 and 125. The database server 124 is shown in FIG. 1 in exemplary form as a single server, but it should be understood that two or more networked servers can together comprise a database network, and can be cloud-based, to achieve the same functions ascribed herein to the database server 124. Voice recognition service 126 is shown as comprising a cloud computing environment as described above with regard to cloud 116, but can instead be a single server having a configuration such as that of the database server 124. Voice recognition service 126 provides conversational interactions, utilizing automated speech recognition-response (ASR), natural language processing, predictive algorithms, and the like, to perform functions, interact with a user, fulfill user requests, and the like. A representative cloud-based voice control service can be implemented through a SaaS model or the like. One example of a voice recognition service is Alexa® Voice Services ("AVS"), available from Amazon.com, Inc. (Seattle, Wash.), though other available voice recognition services could be used. Such a service provides access to one or more remote servers containing hardware and software to operate in conjunction with a voice-controlled speech device (such as wearable interactive notification device 100), application, or the like.

In a current implementation, the voice recognition service 126 can provide an ASR function (component) 128, a natural language understanding (NLU) function (component) 130, an intent router/controller 132, and one or more applications (APN) 134, 136, 138 providing comments back to a voice-controlled speech interface device, application, or the like. The ASR function 128 can recognize human speech in an audio signal transmitted by a voice-controlled speech interface device received from a built-in microphone. The NLU function 130 can determine a user intent based on user speech that is recognized by the ASR components 128. The voice recognition service 126 can also include speech generation functionality that synthesizes speech audio. The voice recognition service 126 can also provide a dialog management component configured to coordinate speech dialogs or interactions with the user in conjunction with the speech services. Speech dialogs may be used to determine the user intents using speech prompts. One or more applications 134, 136, 138 can serve as a command interpreter that determines functions or commands corresponding to intents expressed by user speech. In certain instances, commands may correspond to functions that are to be performed by the voice-controlled speech interface device and the command interpreter may in those cases provide device commands or instructions to the voice-controlled speech interface device for implementing such functions. The command interpreter can implement "built-in" capabilities that are used in conjunction with the wearable interactive notification device 100. The voice recognition service 126 may be configured to use a library of installable applications including one or more software applications 134, 136, 138 or skill applications. The voice recognition service 126 can include network-based services (such as Amazon Lambda™) that enable the voice recognition service 126 to obtain information, and access additional databases, applications, or services on behalf of a user. A dialog management component (not shown) is configured to coordinate dialogs or interactions with the user based on speech as recognized by the ASR component 128 and or understood by the NLU component 130. The voice recognition service 126 can also have a text-to-speech component (also called a "translation engine") configured to translate text into a voice signal, and to translate a voice signal into text, responsive to the dialog management component to generate speech for playback on the wearable interactive notification device 100. These components can function based on models or rules, which may include acoustic models, specific grammar, lexicons, phrases, responses, and the like created through various training techniques.

Again referring to the voice recognition service 126 exemplified in FIG. 1, the dialog management component may utilize dialog models that specify logic for conducting dialogs with users. A dialog comprises an alternating sequence of natural language statements or utterances by the user and system generated speech or textual responses. The dialog models embody logic for creating responses based on received user statements to prompt the user for more detailed information of the intents or to obtain other information from the user. An application selection component or intent controller 132 identifies, selects, and/or invokes installed device applications and/or installed server applications in response to user intents identified by the NLU component 130. In response to a determined user intent, the intent controller 132 can identify one of the installed applications 134, 136, 138 capable of servicing the user intent. The application can be called or invoked to satisfy the user intent or to conduct further dialog with the user to further refine the user intent. Each of the installed applications can have an intent specification that defines the serviceable intent. The voice recognition service 126 uses the intent specifications to detect user utterances, expressions, or intents that correspond to the applications 134, 136, 138. An application intent specification may include NLU models for use by the NLU component 130. In addition, one or more installed applications may contain specified dialog models to create and coordinate speech interactions with the user. The dialog models may be used by the dialog management component in conjunction with the dialog models to create and coordinate dialogs with the user and to determine user intent either before or during operation of the installed applications. The NLU component 130 and the dialog management component may be configured to use the intent specifications of the applications 134 either to conduct dialogs, to identify expressed intents of users, identify and use the intent specifications of installed applications, in conjunction with the NLU models and dialog modes, to determine when a user has expressed an intent that can be serviced by the application, and to conduct on or more dialogs with the user. As an example, in response to a user utterance, the voice recognition service 126 can refer to the intent specifications of multiple applications 134, 136, 138, including both device applications and server applications, to identify a user intent. The voice recognition service 126 can then invoke a corresponding application from among applications such as at 134, 136, 138. Upon invocation, any of the applications 134, 136, 138 can receive an indication of the determined intent and may conduct or coordinate further dialogs with the user to elicit further intent details. Upon determining sufficient details regarding the user intent, the invoked application may perform its designed functionality in fulfillment of the intent. It is to be understood that while the foregoing elements are included in implementations of Amazon's AVS at the time of writing of this disclosure, that AVS and other voice recognition services may evolve to include other or additional voice recognition elements, and that the foregoing description of voice recognition service 126 should not be construed as confining the types of voice recognition services that can be implemented in the interactive notification system 104.

The communication links shown in FIG. 1 represent a network or networks that may comprise hardware components and computers interconnected by communications channels that enable sharing of resources and information. The interactive notification system 104 may comprise one or more of a wired, wireless, fiber optic, or remote connection via a telecommunication link, an infrared link, a radio frequency link, a cellular link, a Bluetooth® link, or any other suitable connectors or systems that provide fiber optic uses optical communication and wireless uses electro-magnetic communication. The network may comprise intermediate proxies, routers, switches, load balancers, and the like. The paths followed by the network between the elements of the interactive notification system 104 as depicted in FIG. 1 represent the logical communication links between those elements, not necessarily the physical paths or links between and among those elements.

It will be appreciated that the configuration of the interactive notification system 104 shown in FIG. 1 and described above is merely one configuration, and additional devices and/or alternative configurations may be conceived by one skilled in the art. As such, the network topology shown in FIG. 1 and the network configurations described should not be construed as limiting but, instead, as merely exemplary.

Figure 2:
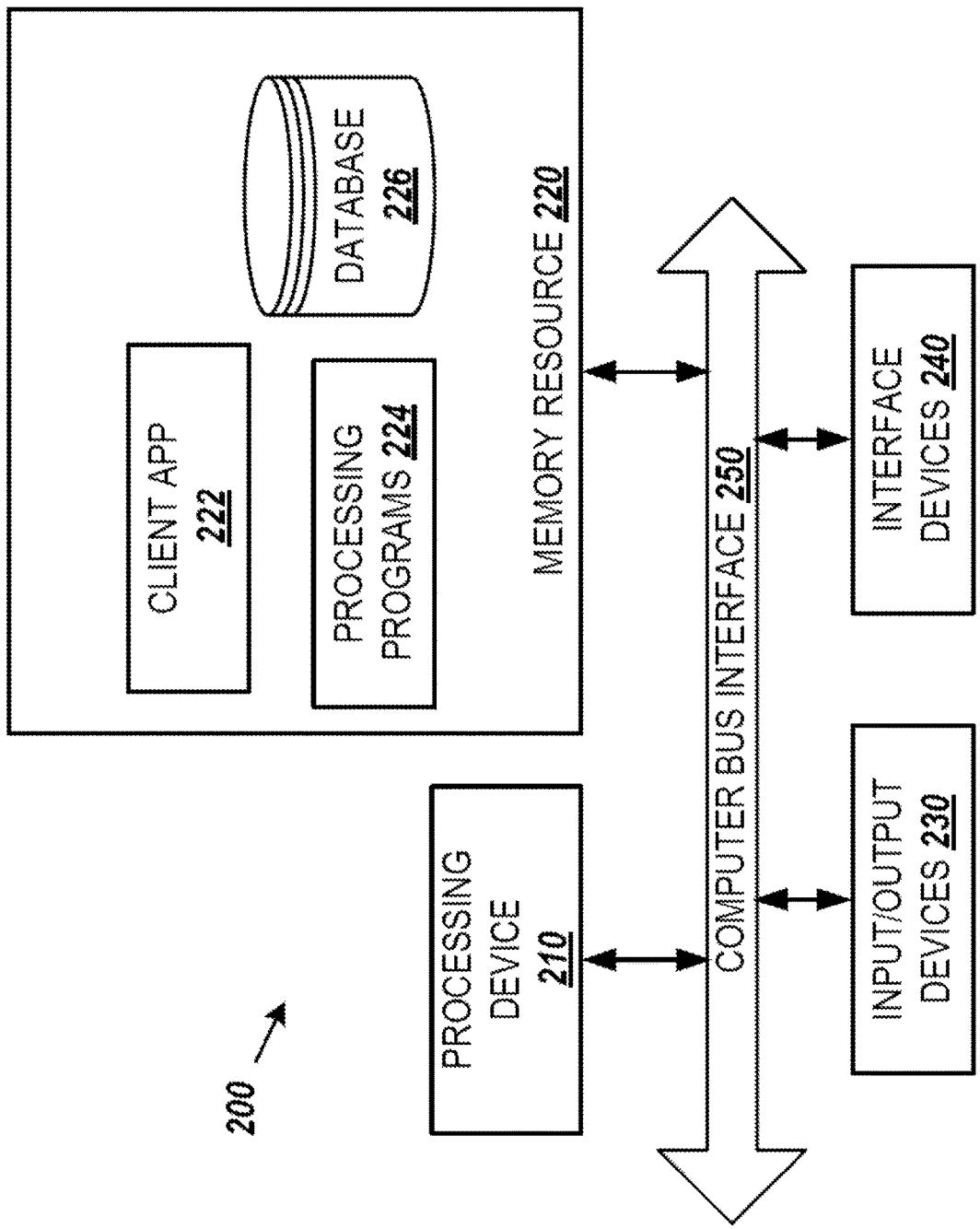
FIG. 2 is a block diagram illustrating a computer architecture for computing devices, other than the wearable interactive notification device described herein, as part of the interactive notification system, according to aspects of the present disclosure.

FIG. 2 is a block diagram illustrating an embodiment of a computer system 200 utilized in elements of the interactive notification system 104 other than the wearable interactive notification device 100, according to various implementations of the present disclosure. The computer system 200 may represent a user device 108 and/or 110, the database server 124 shown in FIG. 1, or another computer system comprising the systems described herein or for performing the methods described herein. As shown in this embodiment, the computer system 200 includes a processing device 210 and a memory resource 220. The memory resource 220 can include one or more client apps 222 for allowing elements in system 104 other than device 100 to communicate with other such elements of the interactive notification system 104. For example, client app 222 in a mobile user device 108 can comprise software permitting that device 108 to communicate with the cellular network 114 over communication link 109, and a client app 222 in the database server 124 can enable the database server 124 to communicate with the voice recognition service 126 (FIG. 1) according to aspects of the present disclosure. The memory resource 220 can also store a device program 224 that includes suitable instructions for processing the communications exchanged between elements in the interactive notification system 104 other than the wearable interactive notification device 100. Memory resource 220 can also store a database 226 and/or the like. The computer system 200 further includes input/output devices 230 and interface devices 240. The components of the computer system 200 are interconnected and may communicate with each other via a computer bus interface 250 or other suitable communication devices.

In some embodiments, each component of the computer system 200 as shown may include multiple components on multiple computer systems of a network. For example, the computer system 200 may comprise servers, such as application servers, file servers, database servers, web servers, etc., for performing various functions described herein. The servers of the computer system 200 may for example be physically separate computer servers or virtual servers in a VMware ESXi 4.0 virtual environment, among other implementations.

The processing device 210 may be one or more general-purpose or specific-purpose processors, microcontrollers, or microprocessors for controlling the operations and functions of the database server 124. In some implementations, the processing device 210 may include a plurality of processors, computers, servers, or other processing elements for performing different functions within the computer system 200.

The memory resource 220 can include one or more internally fixed storage units, removable storage units, and/or remotely accessible storage units, each including a tangible storage medium. The various storage units can include any combination of volatile memory and non-volatile memory. For example, volatile memory may comprise random access memory (RAM), dynamic RAM (DRAM), etc. Non-volatile memory may comprise read only memory (ROM), electrically erasable programmable ROM (EEPROM), flash memory, etc. The storage units may be configured to store any combination of information, data, instructions, software code, etc. The client app 222, the processing programs 224, the database 226, and/or the like may be stored in one or more memory resources 220 and run on the same or different computer systems and/or servers.

In addition to the memory resource 220, the computer system 200 can include other computer-readable media storing information, data, instructions, software code, etc. It will be appreciated by those skilled in the art that computer-readable media can be any available media that may be accessed by the computer system 200, including computer-readable storage media and communications media. Communications media includes transitory signals. Computer-readable storage media includes volatile and non-volatile, removable and non-removable storage media implemented in any method or technology for the non-transitory storage of information. For example, computer-readable storage media includes, but is not limited to, RAM, ROM, erasable programmable ROM ("EPROM"), electrically-erasable programmable ROM ("EEPROM"), FLASH memory or other solid-state memory technology, compact disc ROM ("CD-ROM"), digital versatile disk ("DVD"), high definition DVD ("HD-DVD"), BLU-RAY or other optical storage, magnetic cassettes, magnetic tape, magnetic disk storage or other magnetic storage devices and the like. According to some embodiments, the computer system 200 may include computer-readable media storing computer-executable instructions that cause the computer system 200 to perform aspects of the methods described herein in regard to FIGS. 21A and 21B, as well as FIGS. 24 and 25.

The input/output devices 230 may include various input mechanisms and output mechanisms. For example, input mechanisms may include various data entry devices, such as keyboards, keypads, buttons, switches, touch pads, touch screens, cursor control devices, computer mice, stylus-receptive components, voice-activated mechanisms, microphones, cameras, infrared sensors, or other data entry devices. Output mechanisms may include various data output devices, such as computer monitors, display screens, touch screens, audio output devices, speakers, alarms, notification devices, lights, light emitting diodes, liquid crystal displays, printers, or other data output devices. The input/output devices 230 may also include interaction devices configured to receive input and provide output, such as dongles, touch screen devices, and other input/output devices, to enable input and/or output communication.

The interface devices 240 can include various devices for interfacing the computer system 200 with one or more types of servers, computer systems and communication systems, such as a network interface adaptor as is known in the art. The interface devices 240 may include devices for communicating between the database server 124 and the user devices 108, 110 and/or the voice recognition service 126 over the cellular communication network 114 and/or cloud 116 (FIG. 1), for example. In some examples, the interface devices 240 may include a network interface adapter or other hardware or software interface elements known in the art.

The client app 222 can comprise a user application for facilitating the communication between database server 124 and the voice recognition service 126. In some embodiments, the client app 222 can interface with the voice translation service 126 over the cloud 116 (FIG. 1). The client app 222 may further represent a web-based application executing on the database server 124 or other web server and delivered to a web browser executing on the user devices 108, 110 over the communication network(s)/cloud(s) 114, 116. The client app 222 may be implemented in hardware, software, or any combination of the two on the database server 124, and/or other computing systems in the interactive notification system 104.

Wearable Interactive Notification Device Overview

Figure 3B:
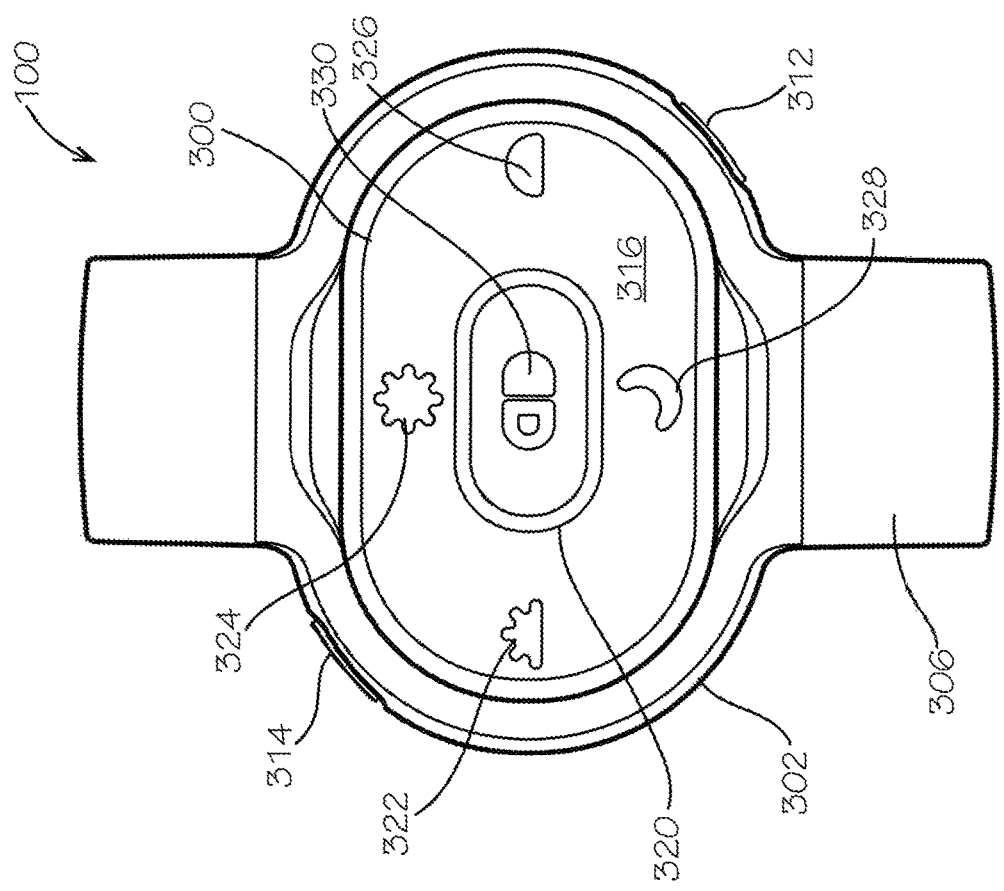
FIG. 3B is a top view of the wearable interactive notification device illustrated in FIG. 3A.
Figure 3A:
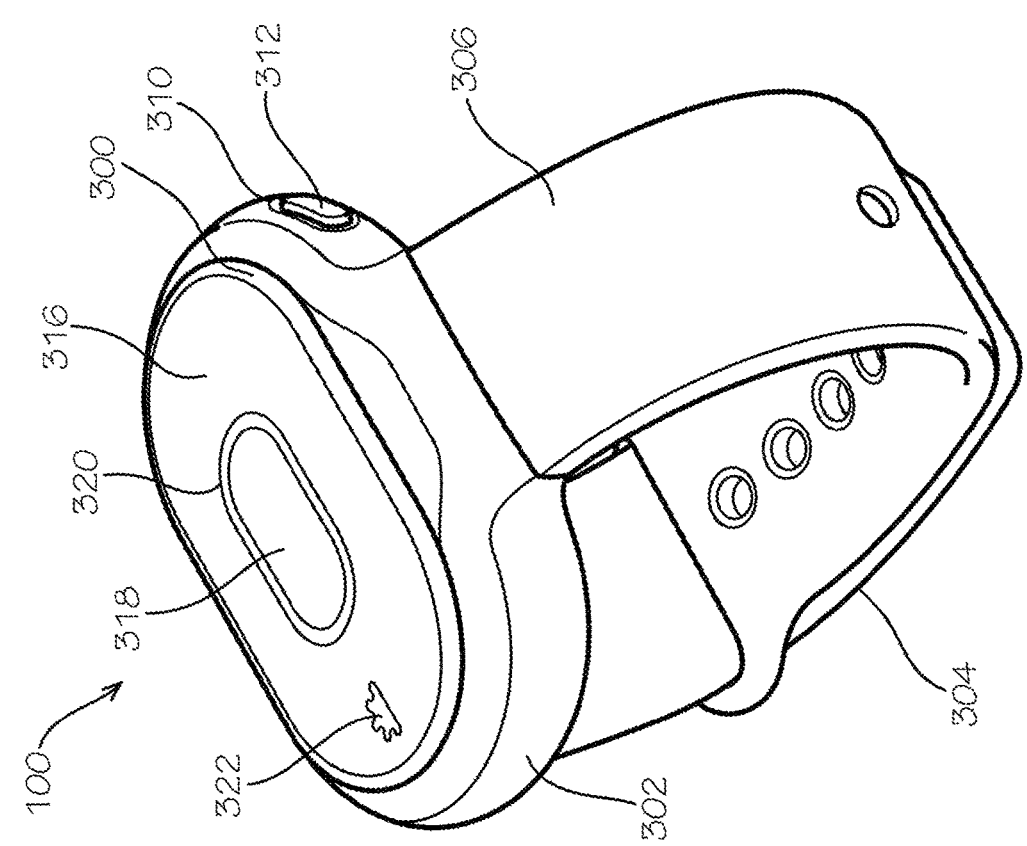
FIG. 3A is a perspective view of a wearable interactive notification device constructed according to an aspect of the present disclosure.

FIGS. 3A and 3B illustrate a wearable interactive notification device 100 constructed according to an aspect of the present disclosure. Wearable interactive notification device 100 comprises a housing 300 received in a wristband frame 302 of wristband 304. Housing 300 contains a printed circuit board and flexible members on which hardware elements are mounted (see FIGS. 10A and 10B). In some implementations, the housing 300 can be removable from the wristband frame 302. A wristband strap 306 is joined to sides of the wristband frame 302 by any suitable means. An aperture 310 can be formed into the wristband frame 302 to accommodate a first side button 312. An identically-constructed second side button 314 can be provided in another aperture formed in the wristband frame 302 opposite the aperture 310, as exemplified in FIG. 3B. Side buttons 312, 314 (also referred to herein as auxiliary buttons), are described in detail herein with regard to FIG. 10A. When a user presses the side buttons 312,314 simultaneously, the wearable interactive notification device 100 sends an emergency alert to the database server 124 (FIG. 1), in a manner to be described in detail with regard to FIG. 7A. The housing includes a display panel 316 with a central portion 318, about which a backlit oval-shaped light-emitting diode (LED) ring 320 may be positioned. The LED ring 320 can be illuminated in the manner discussed herein with regard to FIG. 8B, though that discussed manner of illumination is not intended to be limiting. The display panel 316 is constructed of material rigid enough to maintain a flat profile when not pressed, yet sufficiently flexible such that a user can actuate a primary upper button (FIG. 10A) disposed directly beneath central portion 318 by pressing downwardly on that central portion 318. As discussed herein with regard to FIG. 7A, actuating the primary upper button 710 can, during a medication event, open a communication channel between the wearable interactive notification device 100 and the voice recognition service 126 (FIG. 1). If pressed outside a medication event, the upper button can cause the sending of the same emergency alert as that generated by pressing the two side buttons 312,314, as discussed above. The display panel 316 can also display one or more LED-backlit icons, such as morning icon 322, afternoon icon 324, evening icon 326, and night icon 328. These icons can be illuminated in the manner discussed herein with regard to FIG. 8A, though that discussed manner of illumination is not meant to be limiting. Finally, as shown in FIG. 3B, the display panel 316 can also display a medication icon 330, which can be pill-shaped as shown, at the central portion 318.

Figure 4:
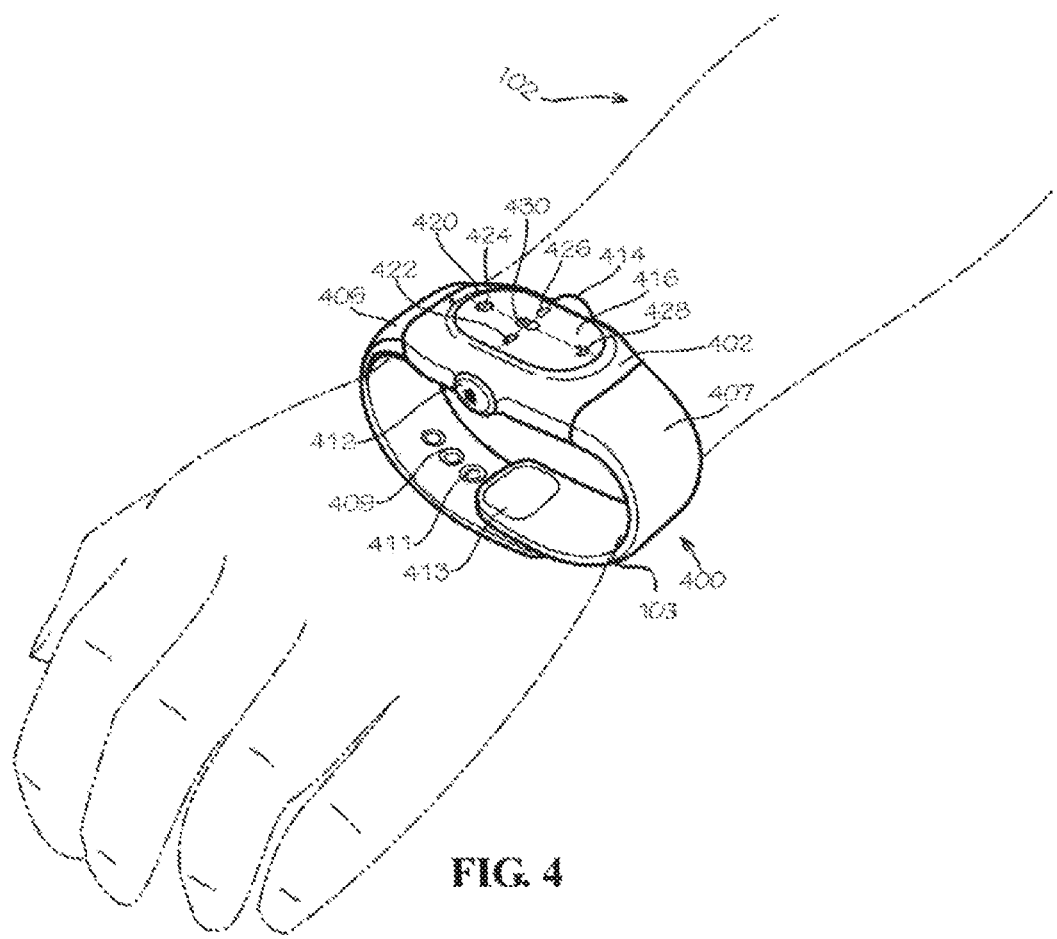
FIG. 4 is a perspective view of a wearable interactive notification device constructed according to another aspect of the present disclosure.
Figure 5:
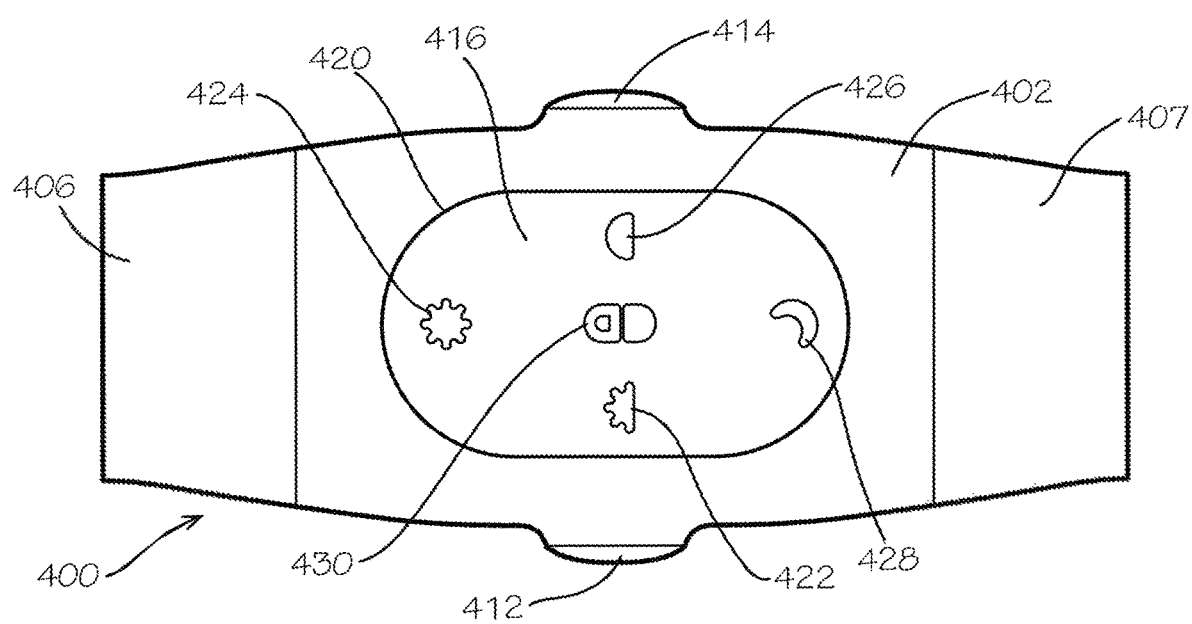
FIG. 5 is a top view of the wearable interactive notification device illustrated in FIG. 4.
Figure 6:
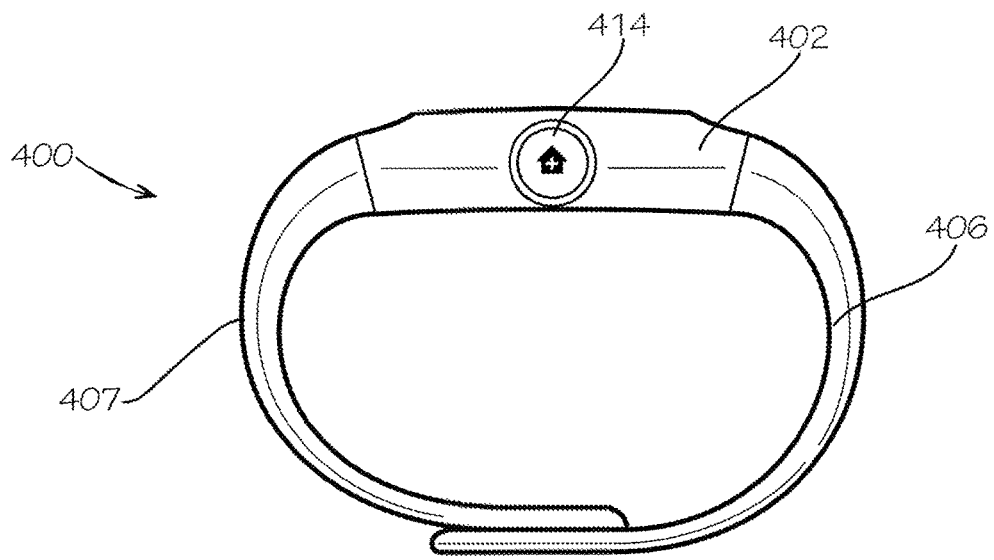
FIG. 6 is a side view of the wearable interactive notification device illustrated in FIG. 4.

FIGS. 4, 5, and 6 are, respectively, perspective, top, and side views of a wearable interactive notification device 400 constructed according to another aspect of the present disclosure. Wearable interactive notification device 400, shown being worn on a wrist 103 of a patient 102, includes a housing portion 402 that, like housing 300 (FIGS. 3A and 3B), contains a printed circuit board on which various hardware elements are mounted. A first wristband strap segment 406 is joined to one side of the housing portion 402 by any suitable means, and the first wristband strap segment 406 may have a plurality of apertures 409 formed therein to expose magnetizable areas 411, formed by embedding a strip of magnetizable material within the first wristband strap segment 406. A second wristband strap segment 407 can be joined to an opposed side of the housing portion, also by any suitable means. The second wristband strap segment can be provided with a pad 413 bearing a magnetic peg (not shown) that will be attracted to any of the magnetizable areas 411, thus providing a means of custom-fitting the wearable interactive notification device 400 to a wrist of a wearer. The housing portion 402 can accommodate a first side button 412 and an opposed second side button 414, with side buttons 412,414 having the same purpose and functions as those disclosed for side buttons 312,314 (FIGS. 3A and 3B). The housing portion 402 includes a display panel 416 with a central portion (located at medication icon 430), about which a backlit oval-shaped light-emitting diode (LED) ring 420 may be positioned. The LED ring 420 can be illuminated in the manner discussed herein with regard to FIG. 8B, though that discussed manner of illumination is not intended to be limiting. The display panel 416 is constructed of material rigid enough to maintain a flat profile when not pressed, yet sufficiently flexible such that a user can actuate an upper (also called primary herein) button (FIG. 10A) disposed directly beneath the medication icon 430 by pressing downwardly on that central portion of the display panel 416. That upper button would be actuated for the same purposes as discussed above with regard to FIGS. 3A and 3B. The display panel 416 can also display one or more LED-backlit icons, such as morning icon 422, afternoon icon 424, evening icon 426, and night icon 428. These icons can be illuminated in the manner discussed herein with regard to FIG. 8A, though that discussed manner of illumination is not meant to be limiting. Finally, the display panel 416 can also display the medication icon 430, which can be pill-shaped as shown. The medication icon 430 would be illuminated in same manner, and for the same purpose, as medication icon 330 of FIGS. 3A and 3B.

Wearable Interactive Notification Device Hardware

Figure 7A:
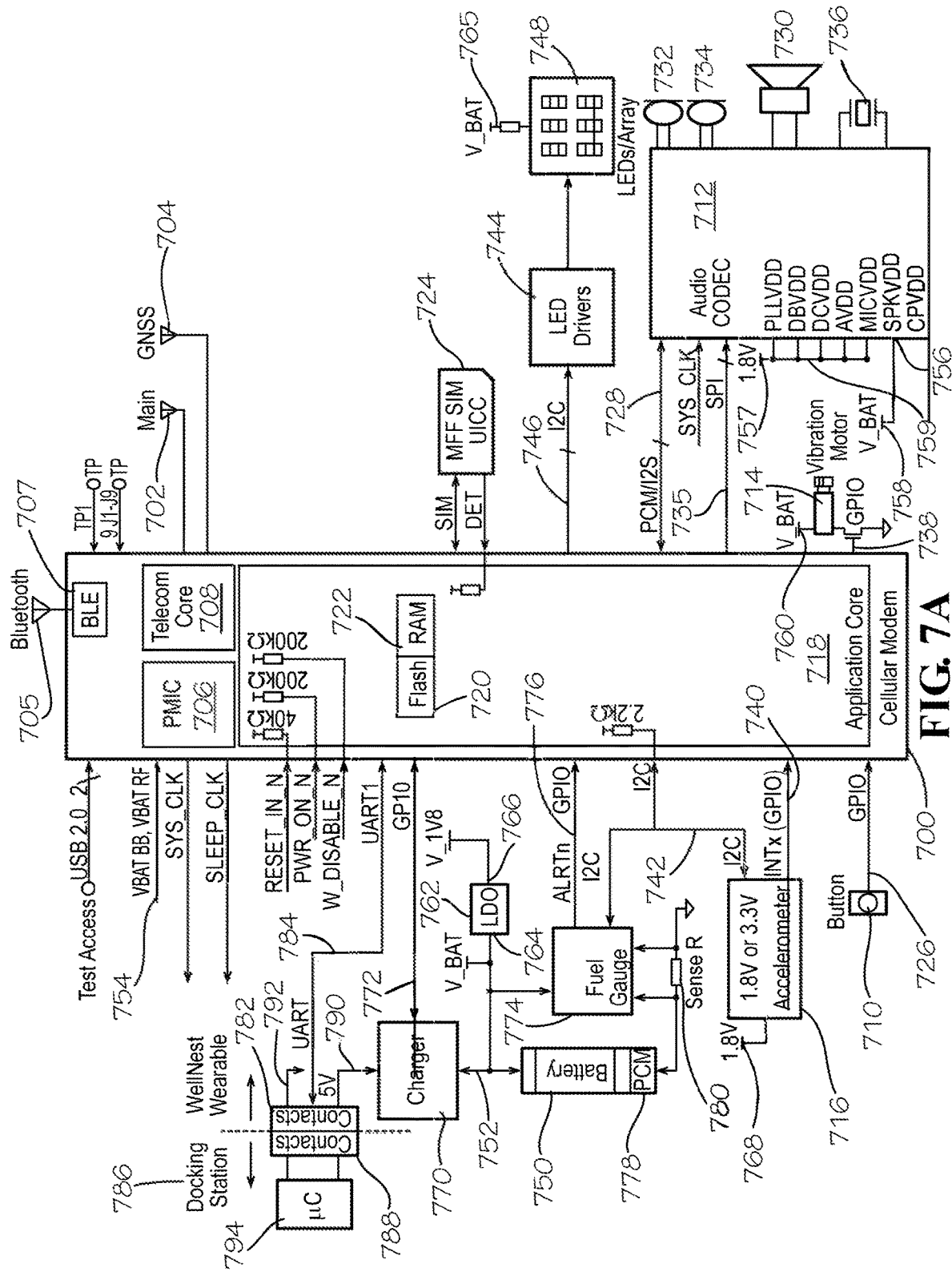
FIG. 7A is a schematic block diagram of exemplary interconnected hardware components of a wearable interactive notification device according to an aspect of the present disclosure.

FIG. 7A is a schematic block diagram of exemplary interconnected hardware components of the wearable interactive notification device 100 (hereinafter "the device 100"). A cellular modem 700 is configured to wirelessly communicate over communication link 112, cellular network 114, and cloud 116 with the database server 124 (FIG. 1) via a main, radio frequency ("RF") antenna 702 in communication with the cellular modem 700 via an RF module (not shown). In an implementation, RF main antenna 702 complies with both 3G and 4G Long-Term Evolution (LTE) wireless communication standards. A Global Navigation Satellite System (GNSS) antenna 704, also in communication with the cellular modem 700 via a GPS module (not shown), allows the cellular modem 700 to communicate with one or more satellite navigation systems, such as Global Positioning System (GPS) for the United States, Galileo for Europe, GLONASS for Russia, and BeiDou for China. In various implementations, the cellular modem 700 can support all of the foregoing satellite navigation systems. The device 100 can also include a Bluetooth® antenna 705 in communication with a Bluetooth® module, such as a Bluetooth® Low Energy ("BLE") module 707. Though BLE module 707 is shown for ease of illustration in FIG. 7A as being inside the boundaries defining the cellular modem 700, it should be understood that the BLE module 707 can be a chip separate from the cellular modem 700. The Bluetooth® antenna 705 would allow the device 100 to, at a lower power than that used for connecting with remote wireless devices, communicate with other Bluetooth®-enabled peripheral devices in the vicinity of the device 100. In various implementations, cellular modem 700 can be commercially available under Model No. WP7603-1, manufactured by Sierra Wireless of Richmond, British Columbia, Canada. Under a present implementation, such a cellular modem 700 includes a power management integrated circuit (PMIC) 706, which controls the flow and direction of electrical power in the cellular modem 700. Such a cellular modem 700 also presently includes a core chipset manufactured by Qualcomm, Inc. (San Diego, Calif.) under Model No. MDM9207, which contains a microprocessor (referred to herein as "processor") 708.

The processor 708 preferably performs several functions, including managing the cellular modem 700, managing power in the device 100, supporting the voice control services described above (such as AVS), detecting buttons such as primary upper button 710, managing audio communications both directly or indirectly through an audio coder-decoder (CODEC) 712, driving a vibration motor 714, and managing an accelerometer 716. It shall be understood that the present disclosure is not limited to the onboard processor shown in FIG. 7A, and that other implementations can use a processor separate from the cellular modem 700. As used herein, for a processor to "communicate with the modem" means that the processor can be either part of the modem, or separate from the modem, so long as data is communicated between the processor and the modem. Also, the foregoing terms "directly" and "indirectly" reflect that the device 100 implements two different audio functions: (i) standard management of cellular phone calls done solely by the cellular modem 700; and (ii) managing, through the Audio Manager 1212 (FIG. 12), the processing of voice-based commands from the patient 102 and the responses thereto received from the voice recognition service 126.

Also as shown in block form in FIG. 7A, the cellular modem 700 includes an application core 718 having a flash memory 720 and Random-Access Memory (RAM) 722. The RAM 722 is volatile memory and thus only temporarily stores data as needed during operation of the device 100. Flash memory 720 can store not only the software applications described in detail with regard to FIG. 12, it also can store voice messages, as further discussed in detail herein. The flash memory 720 can also store executable instructions for causing the processor 708 to receive a reminder notification based upon a predetermined patient medication schedule associated with the patient 102 (FIG. 1), the predetermined patient medication schedule stored in database 226 (see FIG. 2) of the database server 124, the predetermined medication schedule including at least a name of each medication to be taken by the patient 102, the dosage of each such medication, and each time of day during which the patient 102 must take each medication (see FIG. 22), and to automatically execute at least one action in response to receipt of the reminder notification.

As shown in FIG. 7A, a Subscriber Identity Module (SIM) card 724 communicates with the cellular modem 700 to manage network allocation and authentication, and functions as a switchboard for security and access control in wirelessly connecting to the database server 124 (FIG. 1). In various implementations, the SIM card 724 can be an "MFF"-type SIM card, which can operate between −40° and 212° F., and features corrosion-resistant contacts soldered into the circuit board, making it much more robust than plug-in SIMs. Furthermore, integration into electronics provides protection from theft.

Still referring to FIG. 7A, primary upper button 710 communicates with the cellular modem 700 via an interface, such as a General-Purpose Input/Output (GPIO) interface 726. In various implementations, primary upper button 710 can be a momentary "on" switch, the changes of state of which can be detected by the Button Event Handler described below with regard to FIG. 12. The primary upper button 710 is configured to, responsive to pressing the primary upper button 710 for a short duration comprising a range from a predetermined number of milliseconds to five seconds and during a medication event timeframe (which in some implementations can range from 15 minutes to 30 minutes), generate a first interrupt signal configured to cause the cellular modem 700 to transmit a first communication to the database server 124 (FIG. 1), the first communication confirming that the patient 102 has taken a medication that the predetermined medication schedule designated for consumption by the patient 102 at a time of receipt of the reminder notification. Responsive to pressing the primary upper button 710 for the short duration outside of a medication event timeframe, the primary upper button 710 generates a second interrupt signal, the second interrupt signal opening a data communication channel to the database server 124 for allowing the patient 102 to make a request to the database server 124 over the data communication channel. Responsive to pressing the primary upper button 710 for a long duration (greater than five seconds) the primary upper button 710 generates a third interrupt signal that causes the cellular modem 700 to send an emergency signal to the database server 124. Due to the GPS module communicating with the GNSS antenna 704, a contemporaneous geographic location of the device 100 can be included in the emergency notification. The database server 124 can then forward the emergency notification to each user in the care group 106 (FIG. 1) for whom a cell phone number and/or e-mail address has been stored in the database server 124. Each such person in the care group 106 can then respond to the notification at the geographic location pinpointed in the notification. The third interrupt signal can be further configured to cause the cellular modem 700 to place an Enhanced 9-1-1 (E911) emergency call, which provides emergency responders with information as to the location of a caller. In addition, referring to FIG. 8B, the emergency condition can cause a red LED to illuminate an emergency icon 804 on the device 100.

Again referring to FIG. 7A, the audio CODEC 712 can communicate with the cellular modem 700 via both an Inter-integrated circuit Sound (I2S) interface 728 and an SPI interface 735. The I2S interface 728 provides two-way communication of audio signals between the cellular modem 700 and the audio CODEC 712, while the SPI interface 735 communicates control signals from the processor 708 to the audio CODEC 712, such as signals to temporarily and selectively disable peripheral devices communicating with the audio CODEC 712. An exemplary audio CODEC for performing functions according to aspects of the present disclosure can be Model No. WM8962B, commercially available from Cirrus Logic, Inc. (Austin, Tex.). The audio CODEC 712 can decode pulse-code modulated (PCM) digital audio signals from the modem 700 to analog signals, and can also encode (convert) analog signals from connected microphones 732, 734 to digital (PCM) signals. Microphones 732,734 can be analog microphones. Two microphones improve audio quality over a single microphone, but any other suitable number of microphones could be used. The device 100 can further include an oscillator 736 communicating with the audio CODEC 712. The oscillator 736 provides a clock function for the internal circuitry of the audio CODEC 172 and can operate at a frequency of, for example, 24 MHz.

A reminder notification for the patient 102 (FIG. 1) can comprise an encoded voice signal that can take the form of either a streamed encoded voice signal received from the database server 124 (FIG. 1) or a stored encoded voice signal located in the flash memory 720. Recorded verbal reminder notifications are used for all routine, recurring reminders to the patient 102. For example, if the patient's 102's medication schedule calls for any morning medications, then at 8 a.m. every morning, the device 100 can play a locally-stored recorded statement saying: "Good morning. It's time to take your morning medications." Such messages are preferably stored, and played from, the flash memory 720 instead of from the database server 124, which ideally serves only a backup role for the playing of such routine messages. Playing locally-stored messages saves the battery power that would otherwise be consumed by an attempt of the cellular modem to wirelessly communicate with the database server 124. If the encoded voice signal is streamed from the database server 124 (FIG. 1), the processor 708 routes it to the audio CODEC 712, and if the encoded voice signal is stored in the flash memory 720, the processor 708 retrieves the stored encoded voice signal from the flash memory 720 before routing it to the audio CODEC 712. The audio CODEC 712 is configured to decode each received encoded voice signal to produce a decoded voice signal and to then send each decoded voice signal to the speaker 730.

The audio CODEC 712 is also configured to encode (convert, into digital form) voice commands from the patient 102 (FIG. 1). The microphones 732,734 are configured to receive a voice command from the patient 102, convert the voice command to a voice signal, and to send the voice signal to the audio CODEC 712. The audio CODEC 712 encodes the voice signal to produce an encoded voice signal, and transmits the encoded voice signal to the cellular modem 700 via the I2S interface 728. The processor 708 then transmits the encoded voice signal to the voice recognition service 126 (FIG. 1), which through its translation engine translates the encoded voice signal into a text communication. The voice recognition service 126 sends that text communication as a query to the database server 124, to poll the database 226 (FIGS. 2 and 22) in the database server 124. For instance, if the user verbally utters the question "Do I have any new messages?" into the microphones 732,734, the processor 708 transmits the encoded voice signal resulting from that utterance to the voice recognition service 126, that transmission is preceded by a header that contains a number uniquely identifying the particular wearable notification device 100 of the patient 102. For example, since the device 100 is a cellular device, the unique identification number can be the IMEI (International Mobile Equipment Identity) number of the device 100. The voice recognition service 126 translates the payload portion of the communication from the device 100 into text, which the voice recognition service 126 interprets as a command to poll a message table of the database 226 in the database server 124, in the form of, for example, "Select a message from the message table, wherein user ID=XYZ [unique ID digits]." The database server 124 complies with the command by sending the requested information (such as stored text messages received from people within the care group 106 of FIG. 1) to the voice recognition service 126, in text form. The voice recognition service 126 then converts the information from the text form into a response signal that carries a verbal response to the patient's 102's question.

Figure 11:
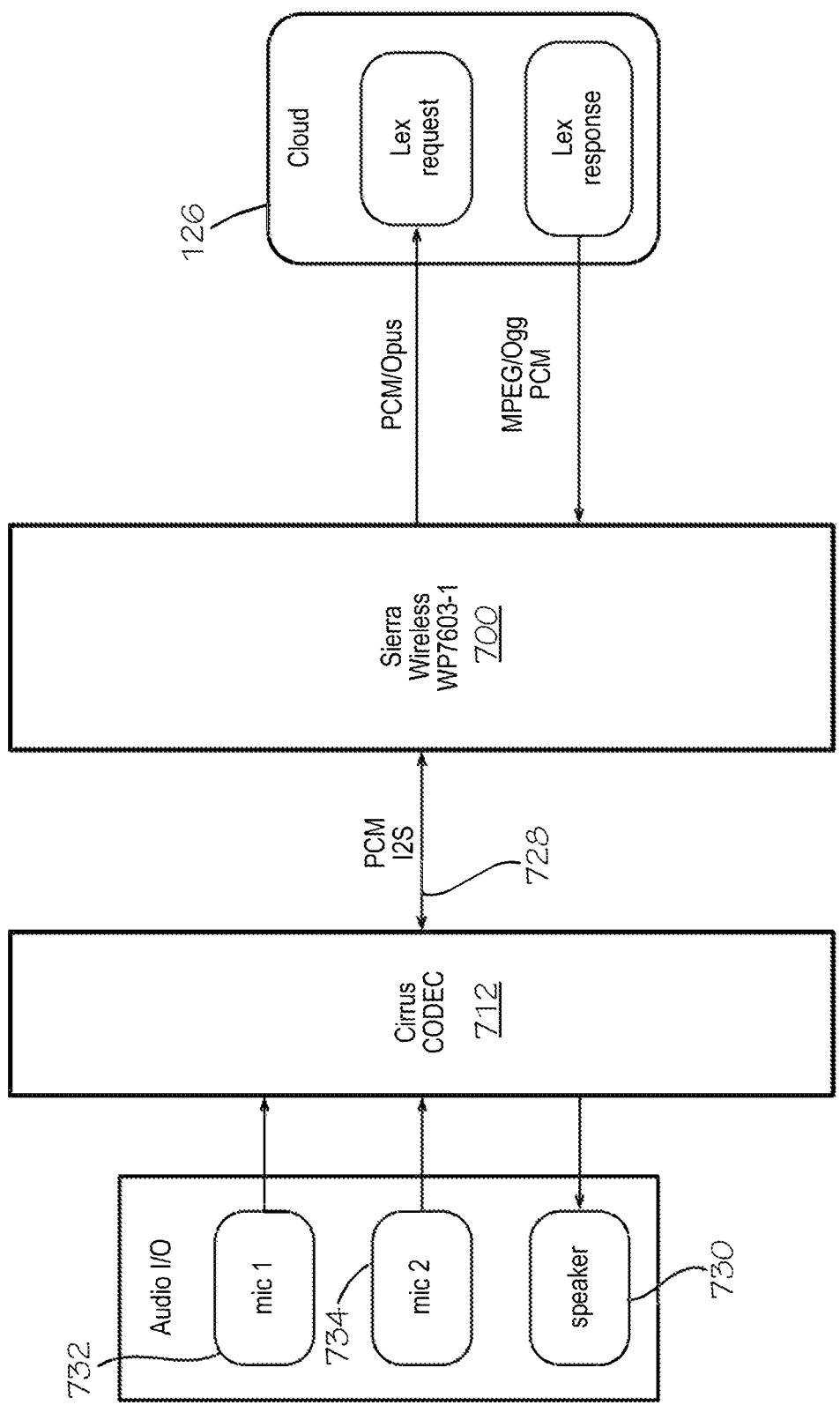
FIG. 11 is a simplified block diagram illustrating some components used in the exchange of verbal commands and verbal responses to the verbal commands, the components located in a wearable communication device or a voice recognition service, according to aspects of the present disclosure.

Still referring to FIG. 7A, the cellular modem 700, via the RF main antenna 702, receives the response signal from the voice recognition service 126 in a format appropriate for the software platform used in the device 100. Examples of supported formats for the Legato® platform, discussed below with regard to FIG. 12, comprise MPEG files, OGG, or a PCM Hypertext Transfer Protocol (HTTP) stream. Upon receipt of the response signal by the cellular modem 700, the processor 708 routes the response signal to the audio CODEC 712, which decodes the response signal to produce a decoded response signal and then sends the decoded response signal to the speaker 730, thereby allowing the patient 102 to hear the response to his/her vocal command. A simplified block diagram illustrating some components used in the exchange of verbal commands and verbal responses to the verbal commands is shown in FIG. 11. FIG. 13B provides another example of a response by the interactive notification system 104 to a vocal command from a patient 102. There, the command begins with an invocation phrase (such as "Wellnest," the name of Applicant's device) followed by a question such as "What are my morning meds again," to which the device 100 can verbally reply by stating, for example: "Your morning medications include 1 Detrol® 2 mg tablet and 1 Lipitor® 20 mg tablet. If you need assistance identifying these, just ask."

FIG. 7A shows the vibration motor 714 communicating with cellular modem 700 via a GPIO interface 738. The processor 708 turns the vibration motor 714 on and off at scheduled times, as determined by directives from the database server 124, a directive instructing the wearable device 100 to take a given action. A reminder notification from the database server 124 can comprise a vibration directive, causing the device 100 to respond by turning the vibration motor 714 on from an off state, or turning the vibration motor 714 off from an on state. Thus, vibration alone can remind the patient 102 to take a given medication. In various implementations, the processor may synchronize activation of the vibration motor 714 so that it coincides with blinking light-emitting diodes (LEDs, described below) on from an off state. Alternatively, the processor 708 may turn the vibration motor 714 on from an off state, and keep it in an on state for a predetermined duration, such as forty seconds, before returning the vibration motor 714 to an off state. Vibration motor 714 can comprise, in various implementations of the present disclosure, a coin-shaped vibration motor, such as that available from Precision Microdrives (London, United Kingdom) under Part No. 304-015, although other suitable motors can be used in other implementations.

Still referring to FIG. 7A, the accelerometer 716 can communicate with the cellular modem 700 via a GPIO interface 740 and also via an Inter-Integrated Circuit (I2C) Bus 742. The accelerometer 716 can be configured to detect, among other things, a free-fall condition of the patient 102, and responsive to detection of the patient free-fall condition, send a first interrupt signal to the processor 708. In particular, the accelerometer 716 can include a free-fall detection algorithm incorporated into its internal design. Using the GPIO interface 740, the accelerometer 716 can be configured to send an interrupt signal to the processor 708 upon detection of a free-fall condition. The flash memory 720 stores executable instructions for causing the processor 708 to, responsive to receipt of that interrupt signal, cause the cellular modem 700 to send a fall event communication to the database server 124. Furthermore, in various implementations, the accelerometer 716 can be configured to wake up the device 100 via the GPIO interface 740 upon detection of a free-fall condition. As such, the processor 708 can remain in a low-power state until the accelerometer 716 sends the interrupt signal. In various implementations the accelerometer 716 is contained within the housing of the device 100 (such as housing 300 in FIGS. 3A and 3B), and the accelerometer 716 is further configured to send another interrupt signal to the processor 708 responsive to a single tap of the housing 300 by the patient 102. Responsive to receipt of that interrupt signal, the processor 708 can send a communication to the database server 124 that the patient 102 has taken a scheduled medication. In some implementations of the notification device 100, the accelerometer 716 is optionally further configured to count a number of steps taken by the patient 102. Responsive to either a user request or engagement of the device 100 with a docking station 786 (further described below with regard to FIGS. 14-18), software polls the accelerometer 716 to send, via the I2C bus 742, step count data indicating a counted number of steps to at least one of the database server 124 and the docking station 786.

Figure 8B:
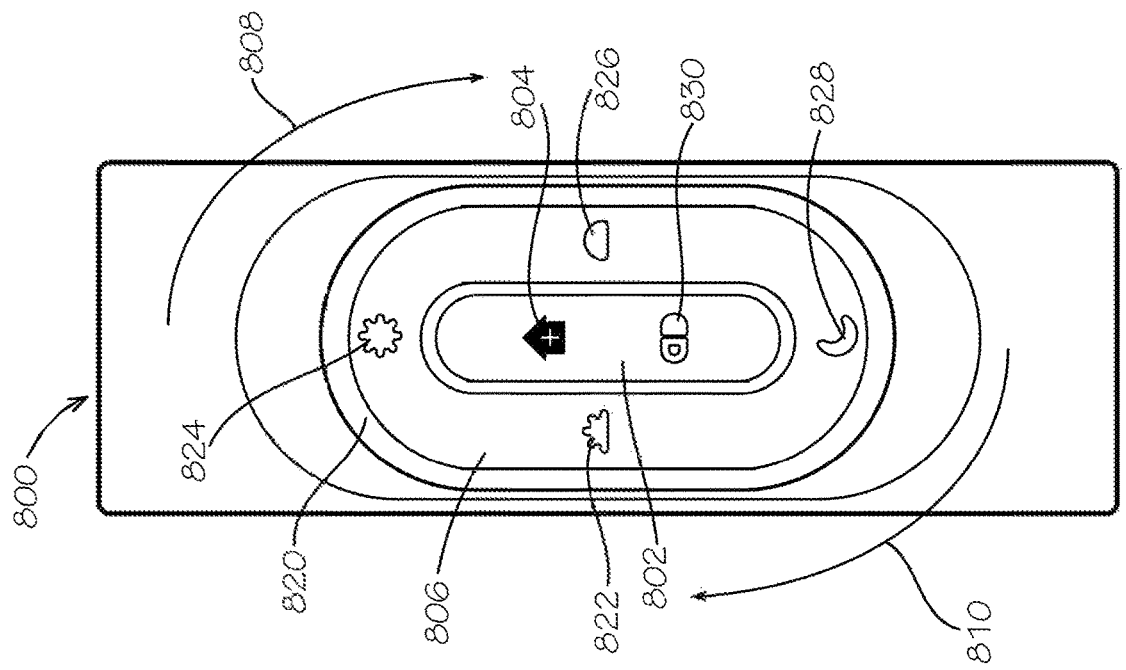
FIGS. 8A and 8B are top views of a housing of a wearable interactive notification device constructed according to another aspect of the present disclosure, illustrating illuminable icons on the housing, as well as an illuminating ring.
Figure 8A:
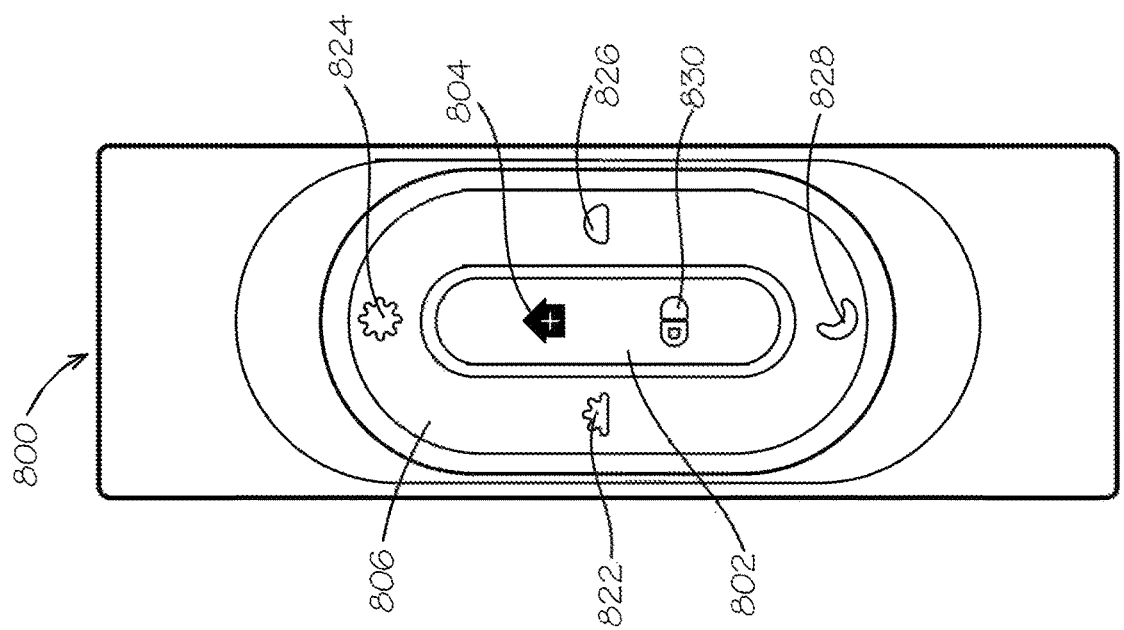

Referring FIGS. 7A, 8A, and 8B, the device 100 is further provided with an LED driver group 744, each LED driver in the group 744 communicating with an interface such as an I2C bus 746 connected to the cellular modem 700, and each LED driver in the group 744 can be configured to have a different bus address. In various implementations, each LED driver in the LED driver group 744 can be commercially available as Model No. SX1509B, available from Semtech Corporation (Camarillo, Calif.). The LED driver group 744 also communicates with an LED array 748, which can be comprised of a plurality of red, green, and blue ("RGB") LEDs. The LED driver group 744 may be comprised of three LED drivers: one driver controlling the red LEDs, one driver controlling the green LEDs, and one driver controlling the blue LEDs. The LEDs in the LED array 748 may be used to illuminate various icons located on a display panel of the housing (such as housing 300 in FIGS. 3A and 3B). For example, FIG. 8A shows a wearable interactive notification device 800 having a central panel 802 displaying an assistance icon 804 and a medication icon 830, and an annular panel 806 surrounding the central panel 802, the annular panel 806 displaying a morning icon 822, an afternoon icon 824, an evening icon 826, and a night icon 828. The assistance icon 804 can be backlit in red with an RGB LED to indicate an emergency condition. The remaining icons can likewise be backlit with RGB LEDs. Additionally, FIG. 8B illustrates that an illuminating ring 820 can be positioned around the perimeter of the annular panel 806. Illuminating ring 820 can be backlit with a predetermined number of LEDs; for example, in an implementation, the illuminating ring can be backlit with eight LEDs. Thus, in the implementation exemplified, the wearable interactive notification device 800 employs six RGB LEDs (one for each of the foregoing six icons), and eight RGB LEDs for the illuminating ring 820, for a total of (6×3)+(8×3)=42 LED control signals. As shown by arrows 808,810, the ring LEDs may illuminate in a sequence to give the appearance of a comparatively brighter light rotating around the ring 820 in the example clockwise direction indicated. In such implementations, a reminder notification can comprise an LED directive from the database server 124, and in response to the LED directive, an LED driver in the LED driver group 744 changes a state of the RGB LED backlighting the medication icon 830. The change of the state of that LED can comprise turning on the LED from an off state, turning off the LED from an on state, blinking, pulsing, fading out from an on state, or fading in from an off state. An LED directive from the database server 124 can also cause the ring LEDs to illuminate in sequence as described above. Notifications can combine the actions involving verbal statements, vibration, and LEDs, as illustrated by Table 1 below.

TABLE 1

Examples of Combined User Interface Actions

| EVENT | VIBRATOR ACTION | LED ACTION | VOICE PROMPT |
|---|---|---|---|
| Medication reminder (morning/afternoon/evening/night) | | | |
| First attempt | 3 pulses | The appropriate Time-of-Day LED will flash 3 times with an aqua color. It will then stay on until the next attempt.<br>The light ring will turn on with an aqua color and pulse white the audio clip is playing. It will turn off after the audio clip has finished playing. | "This is your morning/afternoon/evening/night med reminder." |
| Subsequent attempts | 3 pulses | The appropriate Time-of-Day LED will flash 3 times with an aqua color. It will then stay on until the next attempt.<br>The light ring will turn on with an aqua color and pulse while the audio clip is playing. It will turn off after the audio clip has finished playing. | "Don't forget to take your morning/afternoon/evening/night meditations." |
| Reminder not acknowledged | 3 pulses | The appropriate Time-of-Day LED will turn on with a red color. It will then stay on until the start of the next day.<br>The light ring will turn on with an aqua color and pulse while the audio clip is playing. It will turn off after the audio clip has finished playing.<br>The light ring will turn on with a red color. It will turn off after 3 seconds. | "Looks like you've missed your morning/afternoon/evening/night meds." |
| Reminder acknowledged | none | The appropriate Time-of-Day LED will turn on with a green color. It will then stay on until the start of the next day.<br>The light ring will turn on with a green color. It will turn off after 3 seconds. | None |
| Emergency condition | | | |
| Short Button press | 3 pulses | The light ring will turn on with a red color. It will turn off after 3 seconds.<br>The light ring will turn on with an aqua color and pulse while the audio clip is playing. It will turn off after the audio clip has finished playing. | "I sense you may need help I'm going to call emergency services in 10.9.8.7.6.5.4.3.2.1." |
| Fall detected | 3 pulses | The light ring will turn on with a red color. It will turn off after 3 seconds.<br>The light ring will turn on with an aqua color and pulse while the audio clip is playing. It will turn off after the audio clip has finished playing. | "I sense you may have fallen. I'm going to call emergency services in 10.9.8.7.6.5.4.3.2.1." |
| Emergency cancel | none | The light ring will turn on with an aqua color and pulse while the audio clip is playing. It will turn off after the audio clip has finished playing. | "Emergency cancelled." |
| Server Connections | | | |
| User request (short button press outside of reminder window) | none | The light ring will turn on with an aqua color and pulse while the audio clip is playing. It will turn off after the audio clip has finished playing. | "Connecting to server" |
| Airplane Mode | | | |
| Entry (long button press) | 3 pulses | The light ring will turn on with an aqua color and pulse while the audio clip is playing. It will turn off after the audio clip has finished playing.<br>A single LED in the light ring (8 o'clock position) will turn on with a white color and pulse at a very slow rate. It will turn off once airplane mode is exited. | "Entering airplane mode." |
| Exit (long button press) | none | The light ring will turn on with an aqua color and pulse while the audio clip is playing. It will turn off after the audio clip has finished playing. | "Exiting airplane mode." |
| Warnings | | | |
| Low battery | 3 pulses | A single LED in the light ring (12 o'clock position) will turn on with a red color and pulse at a very slow rate. It will turn off once the device is placed on the docking station/charger. | "Low battery detected" |

Again referring to FIG. 7A, the wearable interactive notification device 100 (again abbreviated herein as "the device 100") can also include a battery 750 having an electrical connection (such as by a wire or by a via in a printed circuit board) to the cellular modem 700, as shown by the "V_BAT" output 752 and the "VBAT_BB, VBAT_RF" input 754 to the cellular modem 700. The battery 750 can similarly supply power to the speaker input pin "SPKVDD" 756 of the audio CODEC 712 at input 758 and to the vibration motor 714 at input 760. In various implementations, the battery 750 can be configured to support at least four days of standby operation and 24 hours of normal use, and can have a capacity of 250 mAh. A Low Drop Out (LDO) regulator 762 regulates output voltage from the battery 750 to provide a lower voltage to certain peripheral devices in the device 100 than that supplied by the battery 750, and to provide a thermal shutdown and current limit to protect those peripheral devices. For instance, in the example of FIG. 7A, the LDO regulator 762 receives the electrical connection 752 from the battery 750 at an LDO input 764, which can receive a battery voltage of, for example, 3.3 V, and outputs at 766 a reduced voltage (which can be 1.8 V in some implementations, although this voltage is not limiting), which is provided at input 757 to simultaneously power a plurality of audio CODEC inputs (other than the "SPKVDD" 756 pin discussed above), and to power the accelerometer 716 at input 768. The audio CODEC 712 thus comprises a plurality of inputs sharing a common connection to a voltage bus 759 at a first voltage (here, the 1.8 V), and a speaker input 756 connected to a power source at a second voltage (here, the 3.3V). The processor 708 is configured to selectively disable at least one of the ports associated with the speaker 730 and the microphones 732, 734, responsive to a determination that the device 100 is in an idle state. Such selective disabling preserves battery power when the device 100 is inactive. A battery charger 770 electrically communicates with the battery 750 and communicates with the cellular modem 700 via an interface such as a GPIO interface 772. Additionally, a fuel gauge 774 can communicate with the cellular modem 700 (and thus with the processor 708) via the I2C bus 742. Fuel gauge 774 also electrically communicates with both terminals of the battery 750. The fuel gauge 774 is configured to monitor a state of charge of the battery 750 and to send an ALERT interrupt signal, via the GPIO interface 776, to the processor 708 when a charge on the battery 750 falls below a predetermined threshold. In some implementations, the fuel gauge 774 can be further configured to cause the cellular modem 700 to send a battery state message to at least one of the database server 124 and a person other than the user, such as another member of care group 106. In further implementations, the fuel gauge 774 can be further configured to cause the processor 708 to, responsive to initiation of charging the battery 750 following the sending of the battery state message, cause the cellular modem 700 to send a battery charging acknowledgement message to at least one of the database server 124 and a person other than the user, such as another member of care group 106. The flash memory 720 stores executable instructions for causing the processor 708 to, responsive to receipt of the ALERT interrupt signal from the fuel gauge 774, retrieve an encoded voice signal stored in the flash memory 720, the stored voice signal corresponding to a verbal alert to for the patient 102 to charge the battery 750, and route that stored encoded voice signal to the audio CODEC 712, which then decodes the voice signal and sends the decoded signal to the speaker 730, which broadcasts the verbal alert to the patient 102. FIG. 7A shows that the battery 750 is provided with a protection circuit module (PCM) 778, which can be part of a battery module, and which is configured to prevent the battery 750 from overcharging or over-discharging. Also shown in communication with the fuel gauge 774 is a current sense resistor 780, which is configured to monitor electrical current through the fuel gauge and to translate that amount of current into a measurable voltage.

Still referring to FIG. 7A, the device 100 is shown including a data output interface 782 communicating with the cellular modem 700 via an interface that can be a Universal Asynchronous Receiver/Transmitter (UART) 784, which is configured to transmit data between the processor 708 and the docking station 786. The data output interface 782 can be a series of apertures, or receptacles, that receive a corresponding number of pins from a data input interface 788 of the docking station 786, described herein with reference to FIG. 16. The terms "input" and "output" used with regard to interfaces 782 and 788 reflects that in various implementations of the present disclosure, there is no requirement for the docking station 786 to return any data to the device 100, but some type of simple acknowledgement message can be included in the protocol. The device 100 detects that it has been docked by sensing a voltage supply input 790 (such as a 5V supply) from the docking station 786 to the battery charger 770. Once docked, the device 100 communicates with the docking station 786 over the UART interface 784. The device 100 passes information from the database server 124 (FIG. 1) to the docking station 786 for display. This information can comprise localized strings that can represent a predetermined number of lines (such as four lines, for example) of text to be displayed on the docking display screen. In some implementations, the lines of text can comprise the expressions: "You have X new messages" (with X denoting a number of messages stored since a prior docking of the device 100); "Just ask, Wellnest, play my messages"; "Earned reward points"; and "Weekly medication adherence." The data transmitted over the UART interface 784 can also include integer values indicating a number of reward points earned by the patient 102 and medication compliance percentage. Reward points can be based on tracking a number of occurrences of medication schedule adherence. In various implementations, there is no requirement for the docking station 786 to return any data to the wearable notification device 100, but some type of simple acknowledgement message can be included in the protocol. A message will only be sent to the docking station 786 when the value for any of the foregoing quoted data items changes since the last time the device 100 was docked. Also, as symbolically represented by arrow 792, once the device 100 is docked in the docking station 786, the interface 782 sends a signal to the processor 708 that the device 100 is in a charged state (now on AC power). This causes the cellular modem 700 to connect to a network such as cloud 116 (FIG. 1) and determine whether it needs to perform any firmware update. Since the cellular modem 700 will only perform firmware updates when such AC power is detected, battery power is not consumed by performing any firmware updates. Finally, FIG. 7A schematically shows a microprocessor 794 of the docking station 786, the microprocessor 794 discussed in further detail below with regard to FIG. 16.

Figure 7B:
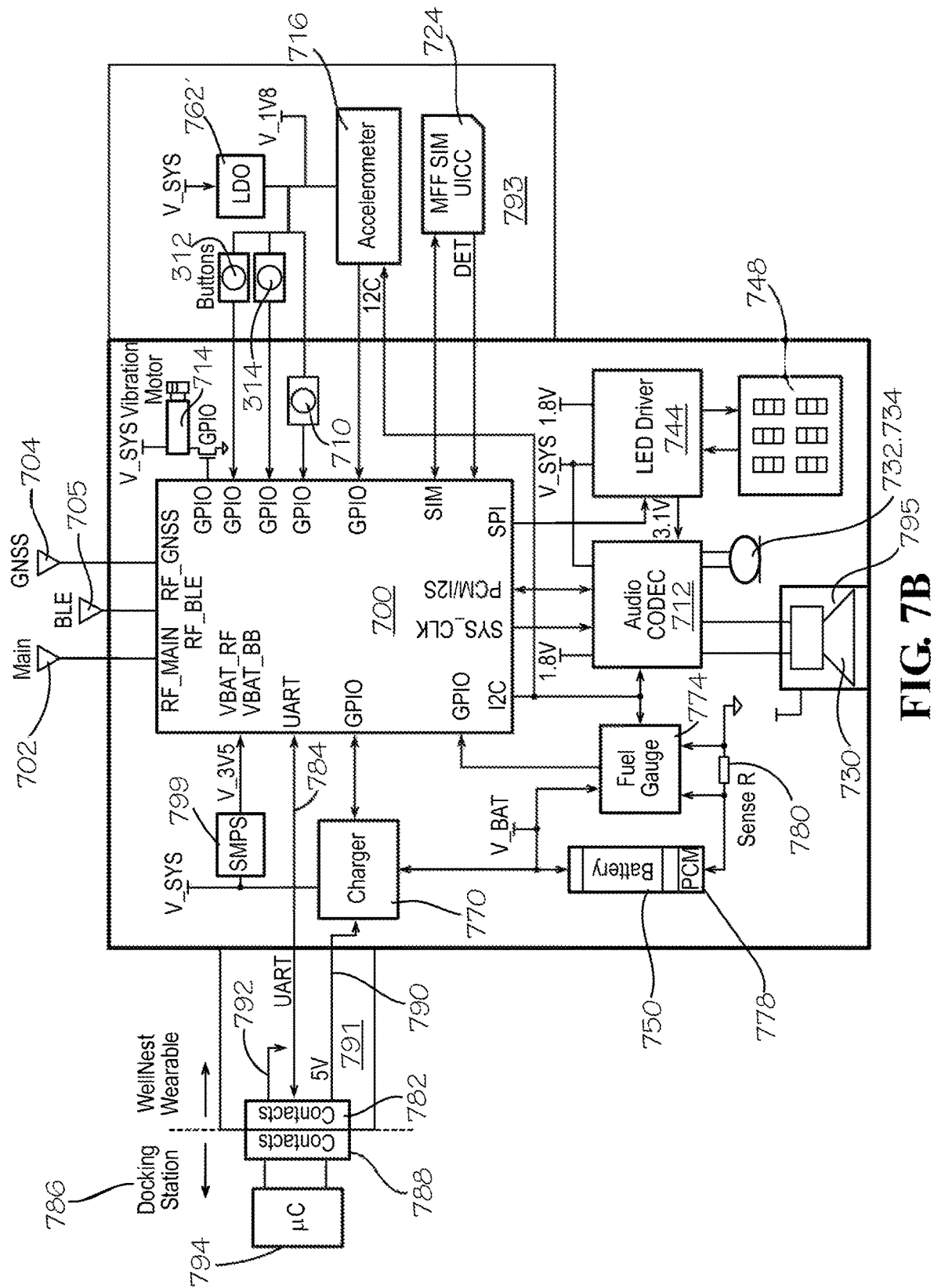
FIG. 7B is a schematic block diagram of exemplary interconnected hardware components of a wearable interactive notification device according to another aspect of the present disclosure.

FIG. 7B is a schematic block diagram of exemplary interconnected hardware components of a wearable interactive notification device according to another aspect of the present disclosure. This figure shows many of the same components illustrated in FIG. 7A, but shows some of those components mounted on flexible areas 791, 793, 795 to minimize space taken up by hardware elements within the confines of a housing for a wearable interactive notification device such as device 100. FIG. 7B additionally shows the two side buttons 312,314 discussed above with regard to FIGS. 3A and 3B. Also newly-shown in FIG. 7B is a switched-mode power supply (SMPS) 799. The function of the SMPS 799 is to reduce the AC-powered voltage of 5V present during docking to a reduced voltage more appropriate for the cellular modem. For instance, with the particular Sierra Wireless modem exemplified above, an input voltage of 3.5V is recommended. Therefore, the SMPS 799 can reduce the AC-powered 5V to the more appropriate 3.5V.

FIGS. 9A and 9B are top and bottom views, respectively, of a printed circuit board (PCB) 900 for a wearable interactive notification device constructed according to an aspect of the present disclosure, showing placement of various hardware components, the reference numbering of which corresponds to components discussed above with regard to FIGS. 7A and 7B.

Referring to FIG. 9A, top surface 901 of the PCB 900 supports, among other elements herein mentioned, the main RF antenna 702 and the GNSS antenna 704. To minimize interference of signal reception by these antennas 702,704, the outer edge 902 of the PCB 900 is shaped to define keep-out indentations 904,906,908,910. Top surface 901 supports battery contacts 912,914 that correspond with, and respectively contact when assembled, power and ground wires 916,918 from the battery 750 (FIG. 9B). Top surface 901 similarly supports speaker contacts 920,922 that correspond with, and respectively contact when assembled, power and ground wires 924,926 from the speaker 730. The remaining elements supported by top surface 901 include the LDO regulator 762, the charger 912, the fuel gauge 774, the current sense resistor 780, the audio CODEC 712, another LDO regulator 762', and the SIM card 724.

Referring to FIG. 9B, the bottom surface 903 of the PCB 900 supports a pair of motor contacts 928, each contact in the pair 928 being contacted by one of a ground and power wire in the pair of motor power wires 930 connected to the vibration motor 714. Bottom surface 903 of the PCB 900 also supports the accelerometer 716. Finally, a connector region 932 is formed into the bottom surface 903 to define a region for an electrical connection to the battery 750.

Figure 10A:
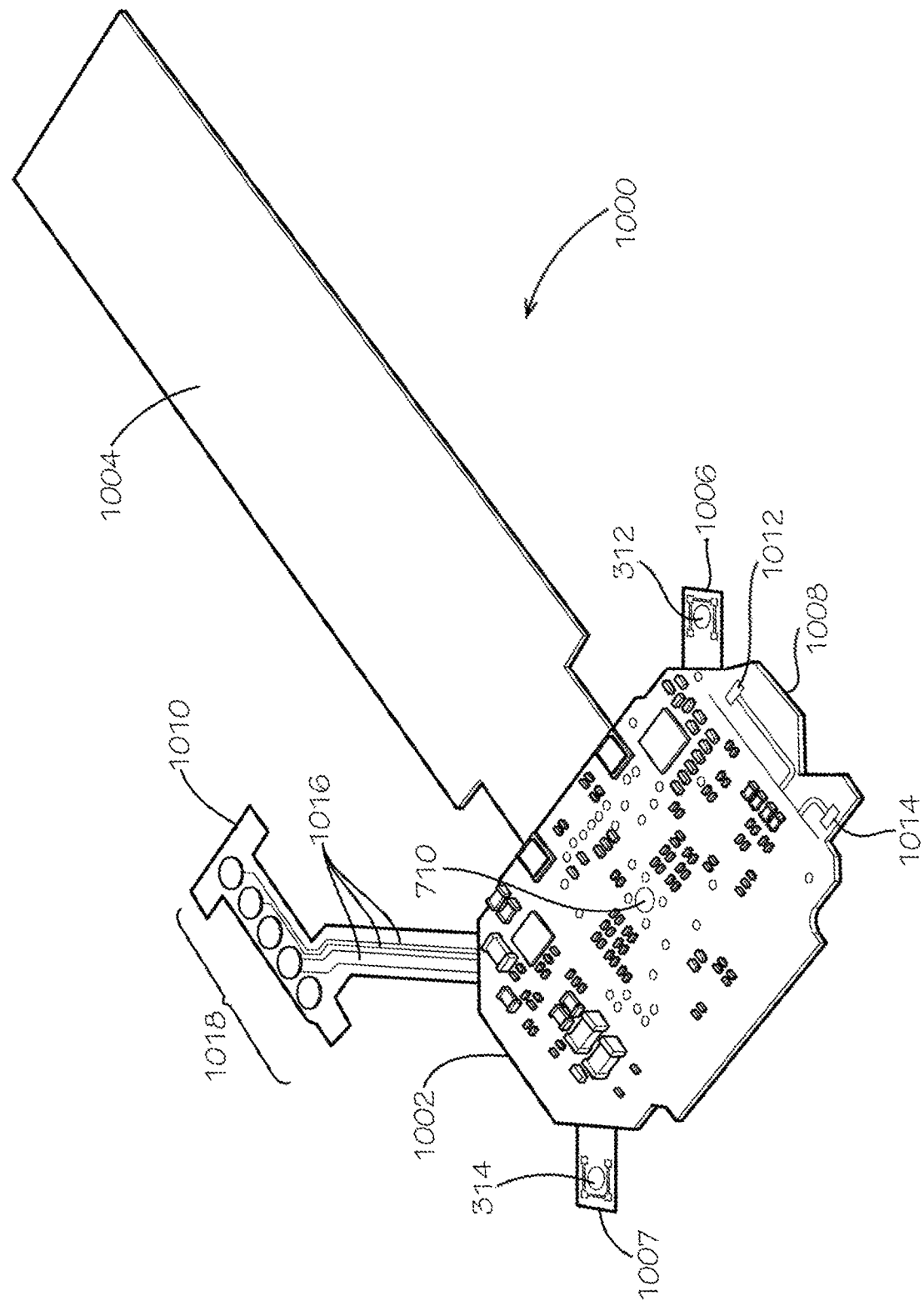
FIGS. 10A and 10B are perspective and bottom views, respectively, of a printed circuit board and ground plane extension element of a wearable interactive notification device constructed according to another aspect of the present disclosure.
Figure 10B:
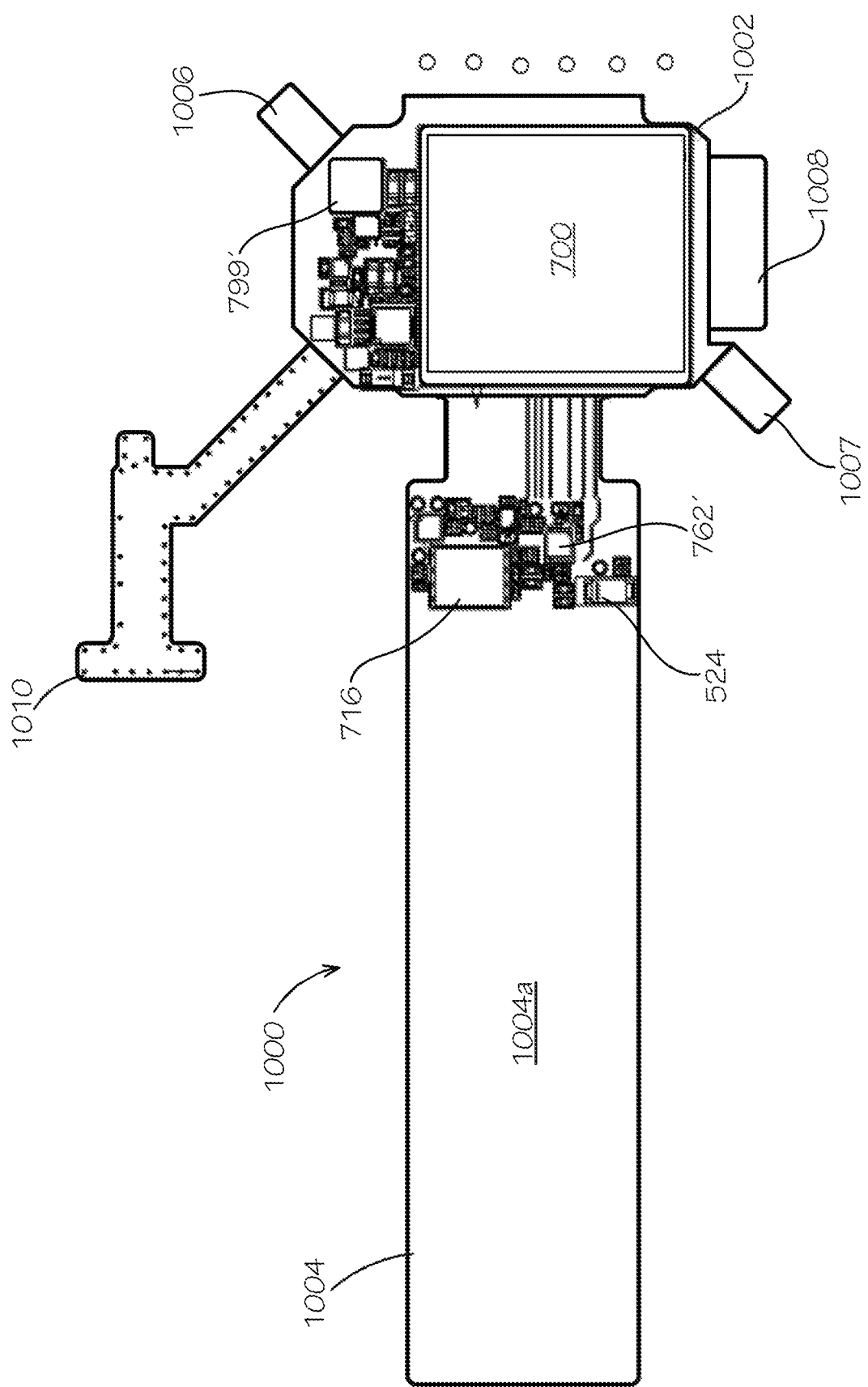

FIGS. 10A and 10B are perspective and bottom views, respectively, of a printed circuit board and ground plane extension element of the device 100 in accordance with another embodiment of the present disclosure. Like FIG. 7B, FIGS. 10A and 10B illustrate flexible members supporting certain hardware components, but the configuration of such members in 10A and 10B differ from the FIG. 7B flexible areas. FIGS. 10A and 10B disclose a circuit assembly 1000 comprising a printed circuit board (PCB) 1002, on which are mounted a plurality of hardware components, including but not limited to the primary upper button 710 located substantially centrally on the PCB 1002, together with a plurality of flexible members 1004,1006,1008,1010 joined to respective edges of the PCB 1002 by any suitable means. Flexible members 1006,1008,1010 can each be constructed of a flexible material such as a polyimide. Flexible member 1004 is a ground plane extension for the main RF antenna 702 and the GNSS antenna 704 (FIG. 7A; see also FIG. 9A for antenna placements). Ground plane extension 1004 comprises a conductor and in some implementations can be constructed of any conductive material, including but not limited to copper, aluminum, brass, and steel. In other implementations, ground plane extension 1004 can comprise a combination of a conductive layer and a dielectric layer.

The conductive layer in such implementations can be comprised of the aforementioned conductive materials. The ground plane extension 1004 is encapsulated in the wristband strap 306 (FIGS. 3A and 3B) of the device 100. The strap 306 can be injection molded to create a flexible strap with two halves. The extension 1004 can be sandwiched or inserted between the two halves and then either snap (press) fit into the halves or glued into place with an adhesive. Flexible member 1006 supports the first side button 312, while flexible member 1007 supports the second side button 314. Flexible member 1008 supports two test points 1012, 1014 for the speaker 730 (FIG. 7A), one for a negative input of the speaker 730, and another for a positive input of the speaker 730. Test points 1012,1014 are supported by the flexible member 1008 so that they can be bent to a side of the device 100 to have close proximity to the inputs of the speaker 730. Flexible member 1010 supports elongated vias 1016 that electrically interconnect PCB 1002 to a series of five electrical contact pads 1018. Referring to the bottom view of FIG. 10B, the ground plane extension 1004 has a bottom surface 1004*a*. The underside of PCB 1002 supports an inductor 799' of the SMPS 799 (FIG. 7B). Also, the underside of the PCB 1002 can support the cellular modem 700.

A brief mention of the simplified diagram of FIG. 11 was made in the above discussion of FIG. 7A. The numbering of components in FIG. 11 refers back to FIG. 7A. The reference to the term "Lex" at "Cloud"/voice recognition service 126 merely illustrates an example of a voice-enabled platform in the voice recognition service, and is not meant to be limiting.

It will be appreciated that the structure and/or functionality of the device 100 may be different than that illustrated in FIGS. 7A-11 and described herein. For example, the cellular modem 700 and other components and circuitry of the device 100 can be integrated within a common integrated circuit package or distributed among multiple integrated circuit packages. Similarly, the illustrated connection pathways are provided for purposes of illustration and not of limitation, and some components and/or interconnections may be omitted for purposes of clarity. It will be further appreciated that the device 100 may not include all of the components shown in FIGS. 7A-11, may include other components that are not explicitly shown in FIGS. 7A-11 or may utilize an architecture completely different than that shown in FIGS. 7A-11.

Wearable Interactive Notification Device Software

Figure 12:
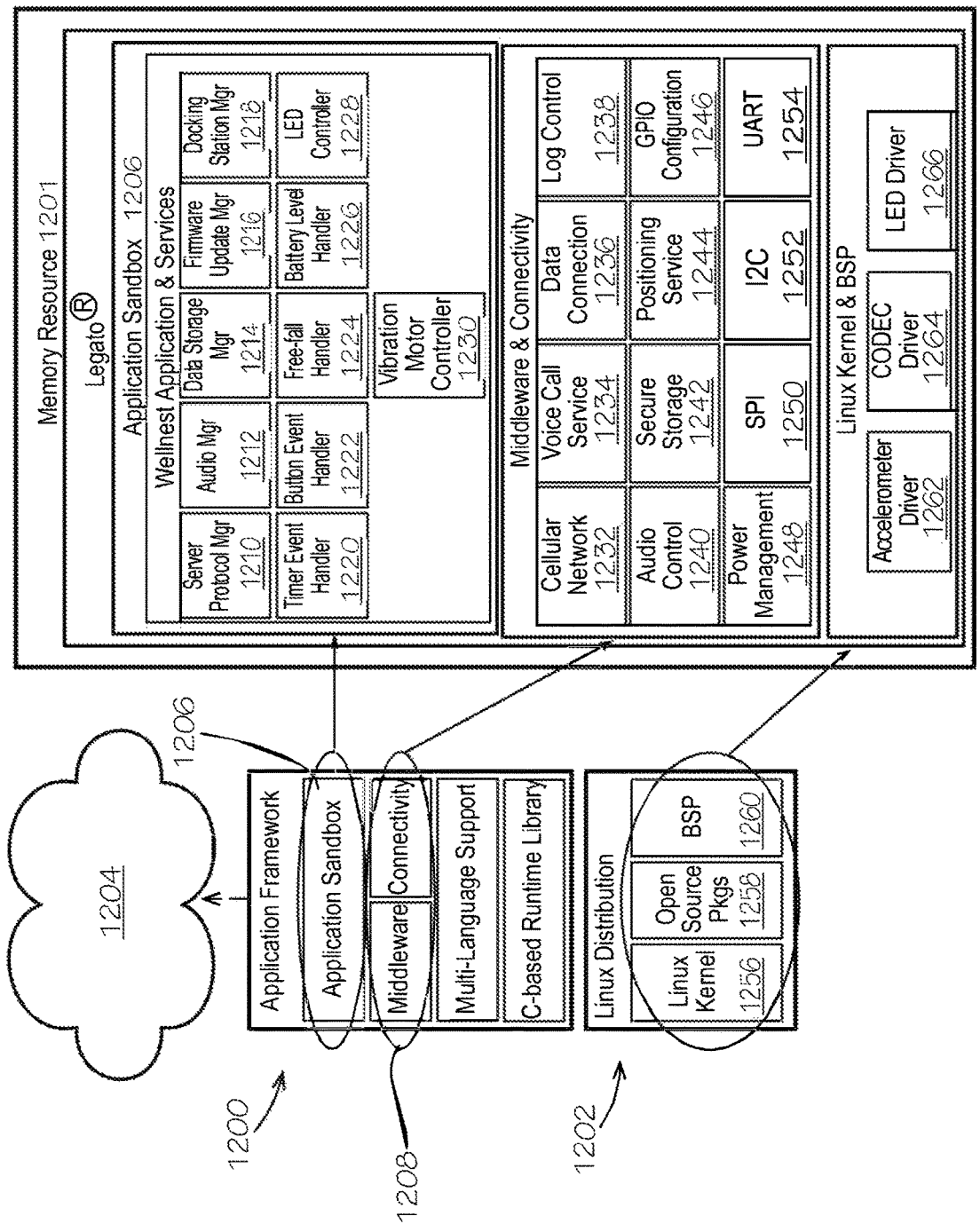
FIG. 12 illustrates an example of a memory resource storing a plurality of custom applications and pre-tested application components, each application and component containing processor-executable instructions to operate a wearable interactive notification device according to aspects of the present disclosure.

FIG. 12 illustrates an example of a memory resource 1201 storing a plurality of custom applications and pre-tested application components, each application and component containing processor-executable instructions to operate the wearable interactive notification device 100 ("the device 100") according to aspects of the present disclosure. In the example shown in FIG. 12, the memory resource 1201 shall be understood to diagrammatically represent a combination of the flash memory 720 and RAM 722 in the cellular modem 700 (FIG. 7A), such that a given module in the memory resource 1201 may contain data and instructions stored in the flash memory 720, in the RAM 722, in a Cloud Platform 1204 (described in the following paragraph), or a combination of the foregoing. However, the memory resource 1201 is not limited to the example of FIG. 12, and in various other implementations can comprise any electronic, magnetic, optical, or other physical storage device that stores executable instructions. Thus, the memory resource 1201 may be, for example, solely RAM, electrically-erasable programmable read-only memory (EEPROM), a storage drive, an optical disk, and any other suitable type of volatile or non-volatile memory that stores instructions to cause a programmable processor (i.e., processing resource) to perform the techniques described herein. The memory resource 1201 may also store other software components necessary for the operation of the device 100 in accordance with the embodiments described herein. The database server 124 (FIG. 1), the processor 708 (FIG. 7A), a computer, or another suitable computing resource may store data on the memory resource 1201 by transforming the physical state of the physical storage units to reflect the information being stored. The specific transformation of physical state may depend on various factors, in different implementations of this description. Examples of such factors may include, but are not limited to, the technology used to implement the physical storage units, whether the memory resource 1201 is characterized as primary or secondary storage, or the like. For example, the processor 708 may store information to the memory resource 1201 by issuing instructions through one or more controllers to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The processor 708 may further read information from the memory resource 1201 by detecting the physical states or characteristics of one or more particular locations within the physical storage units. The computer-executable instructions transform the device 100 by specifying how the processor 708 transitions between states, as described above. According to some embodiments, memory resource 1201 stores computer-executable instructions that, when executed by the processor 708, perform portions of the method discussed herein with regard to FIGS. 21A and 21B. In further embodiments, the processor 708 may have access to other computer-readable storage media in addition to or as an alternative to the memory resource 1201.

In aspects of the present disclosure implementing the Sierra Wireless cellular modem discussed above with regard to FIG. 7A, the cellular modem 700 is pre-loaded with an embedded platform (i.e., hardware, an operating system, and programs that use an instruction set for the processor 708) marketed by Sierra Wireless under the trademark Legato® and built on a fully-tested LINUX distribution (i.e., a LINUX operating system made from a software collection and based upon a LINUX kernel, the core of the LINUX operating system). Referring to FIG. 12, the Legato® platform includes an Application Framework 1200 and a LINUX Distribution 1202. The Application Framework 1200 comprises common software routines that provide a foundation for building and maintaining wireless M2M (machine-to-machine) applications. These routines are made available in Sierra Wireless' AirVantage® M2M Cloud Platform 1204, a Platform as a Service (PaaS, generally discussed above with regards to FIG. 1). The Application Framework 1200 is also configured to provide access to other cloud and network services, such as voice calls, Short Message Service (SMS), data, and radio controls. The Application Framework 1200 includes an "application sandbox" 1206 that provides a secure environment to run and control the multiple applications exemplified at 1210-1230. Application Framework 1200 also includes middleware and connectivity components made available through Legato® (again, via the AirVantage® M2M Cloud Platform 1204), such components generally represented at 1208 and identified more particularly at 1232-1254. As shown in FIG. 12, examples of such components used for the device 100 include a Cellular Network component 1232, a Voice Call Service component 1234, a Data Connection component 1236, a Log Control component 1238, an Audio Control component 1240, a Secure Storage component 1242, a Positioning Service component 1244, a GPIO Configuration component 1246, a Power Management component 1248, and interface components SPI 1250, I2C 1252, and UART 1254. The inclusion of these components decreases the required development time, since they have already been tested and are simply being reused. The LINUX Distribution 1202 is customizable and includes the kernel 1256, which is hosted by the Linux Foundation and maintained by the embedded systems industry. Kernel 1256 is optimized for M2M applications, with common M2M features already integrated. The LINUX Distribution 1202 also includes Open Source Packages 1258 that have been validated by the Linux Foundation's "Yocto Project," examples of such packages including Busybox, OpenSSL, DHCP, PPP, and OpenSSH. The Board Support Package (BSP) 1260 includes support for hardware interfaces and power management. In various implementations of the present disclosure, the LINUX kernel 1256 and BSP 1260 can be updated (customized) with customer drivers to control peripherals, such the accelerometer driver 1262, the audio CODEC driver 1264, and the LED driver 1266.

Referring again to FIG. 12, the various custom applications contained in the Application Sandbox 1206 are now briefly described.

Server Protocol Manager 1210 manages the data contents received from and sent to the database server 124 (FIG. 1). When receiving messages, the Server Protocol Manager 1210 parses the protocol formatted data and, with the Legato® platform, determines the execution path based on the contents of the data. When sending messages, the Server Protocol Manager 1210 makes use of available utilities to format the data into the protocol-specific format.

The Audio Manager 1212 is the application layer manager of the audio processing and files. It will retrieve saved audio files when ready to be played and process them through the Legato® infrastructure to the audio CODEC 712 for playback. The Audio Manager 1212 will also receive the audio files received from the audio CODEC 712 when recording a vocal command from the patient 102.

The Data Storage Manager 1214 manages the storage of data into the flash memory 720 (FIG. 7A). This includes data directives from the database server 124 (FIG. 1) that will be stored for later use, including audio files, docking station data, LED sequences, motor vibration sequences, and configuration settings such as battery alert levels.

The Firmware Update Manager 1216 manages the Over-the-Air firmware update process. This process includes requesting the image from a server, verification of the image, and sending the data to the NonVolatile Handler 1708 (FIG. 17) for storage.

The Docking Station Manager 1218 manages all the data and interfacing to the docking station 786 from the application layer. In some implementations, the Docking Station Manager 1218 can use the Legato® Middleware and Connectivity components 1208 as needed as well as the UART driver 1254 to send data to the docking station 786 and receive acknowledgements.

The Timer Event Handler 1220 receives timer events, triggering application layer processing. This can be used to trigger the daily medication reminders. These timer events can be the main processing trigger outside of user-initiated events.

The Button Event Handler 1222 will receive an interrupt from a GPIO driver when the state of the primary upper button 710 changes. The Button Event Handler 1222 can be responsible for distinguishing a short button press from a long button press, both types described above with regard to FIG. 7A. Based on this determination, the Button Event Handler 1222 can trigger one of the three buttons press processing steps also described above with regard to FIG. 7A.

The Free-Fall Handler 1224 is used to configure the accelerometer 716 with the free-fall detection configuration. The accelerometer 716 will generate an interrupt when free-fall is detected, and this handler will trigger the free-fall processing loop at the application layer.

The Battery Level Handler 1226 is used to configure the fuel gauge 774 (FIG. 7A) with the battery alert level configuration. This configuration is intended to come from the database server 124 (FIG. 1). A GPIO interrupt through the Legato® infrastructure can be sent to the Battery Level Handler 1226 and trigger the low battery processing loop at the application layer.

The LED Controller 1228 provides application layer control of the LED array 748 (FIG. 7A). Based on the configuration received from the database server 124 and control from the application, the LED Controller 1228 determines how to illuminate certain LEDs, for how long, and to what degree. This can be used principally for the ring LED (such as at 820 of FIG. 8B), as the other LEDs are simply GPIO-driven and can be done directly from the application.

The Application Sandbox 1206 can also include a Vibration Motor Controller 1230.

The Vibration Motor Controller 1230 can provide application layer control of the vibration motor 714 (FIG. 7A), if complex patterns are needed. Otherwise, the application itself can use the GPIO driver directly to simply turn the vibration motor 714 on and off at scheduled times.

Examples of Verbal Dialog with the Wearable Interactive Notification Device

FIGS. 13A-13E illustrate examples of verbal dialogs between a patient 102 and the patient's wearable interactive notification device 1300 (hereinafter "the device 1300") according to aspects of the present disclosure.

Figure 13A:
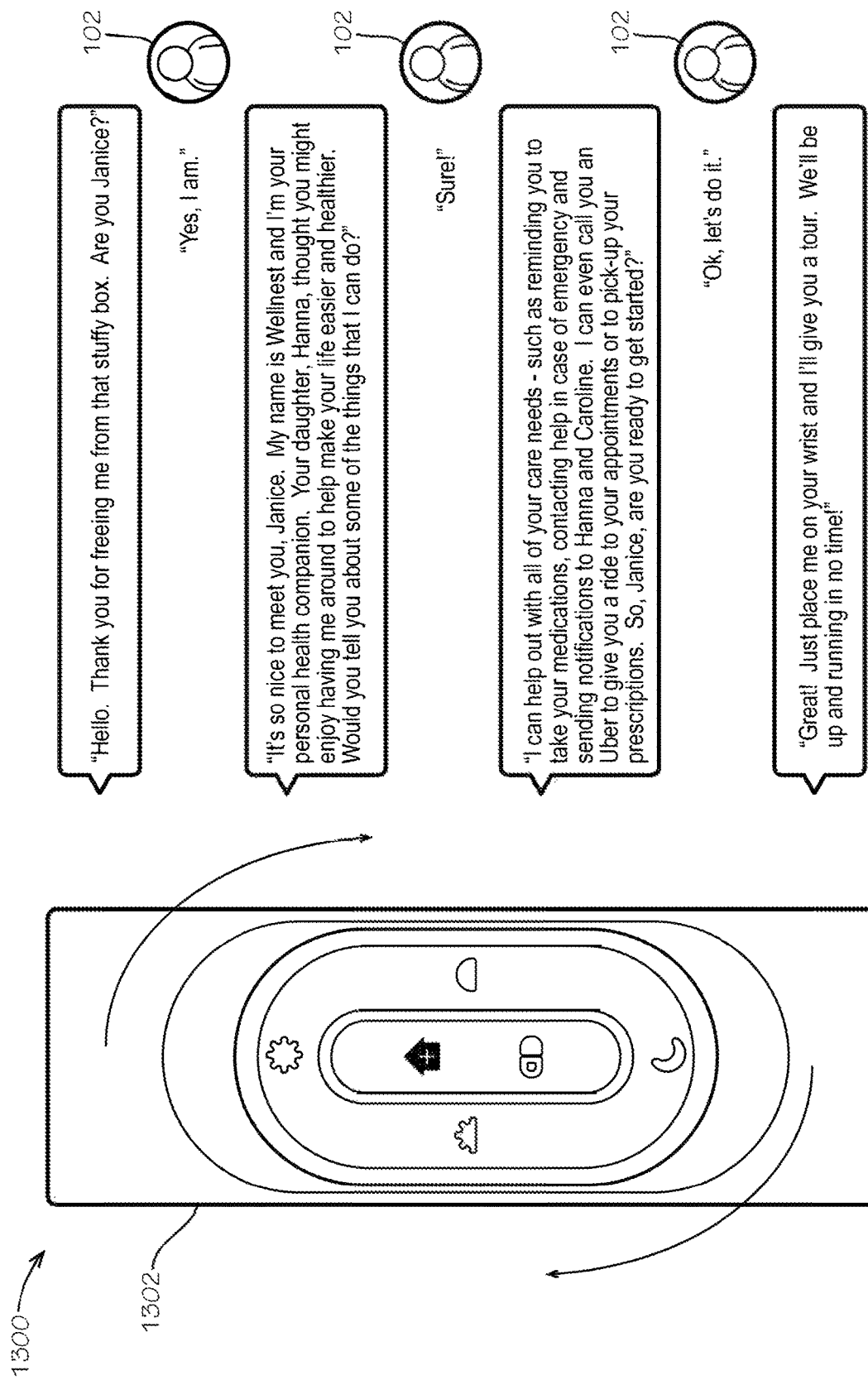
FIGS. 13A-13E illustrate examples of verbal dialogs between a patient and the patient's wearable interactive notification device according to aspects of the present disclosure.
Figure 13B:
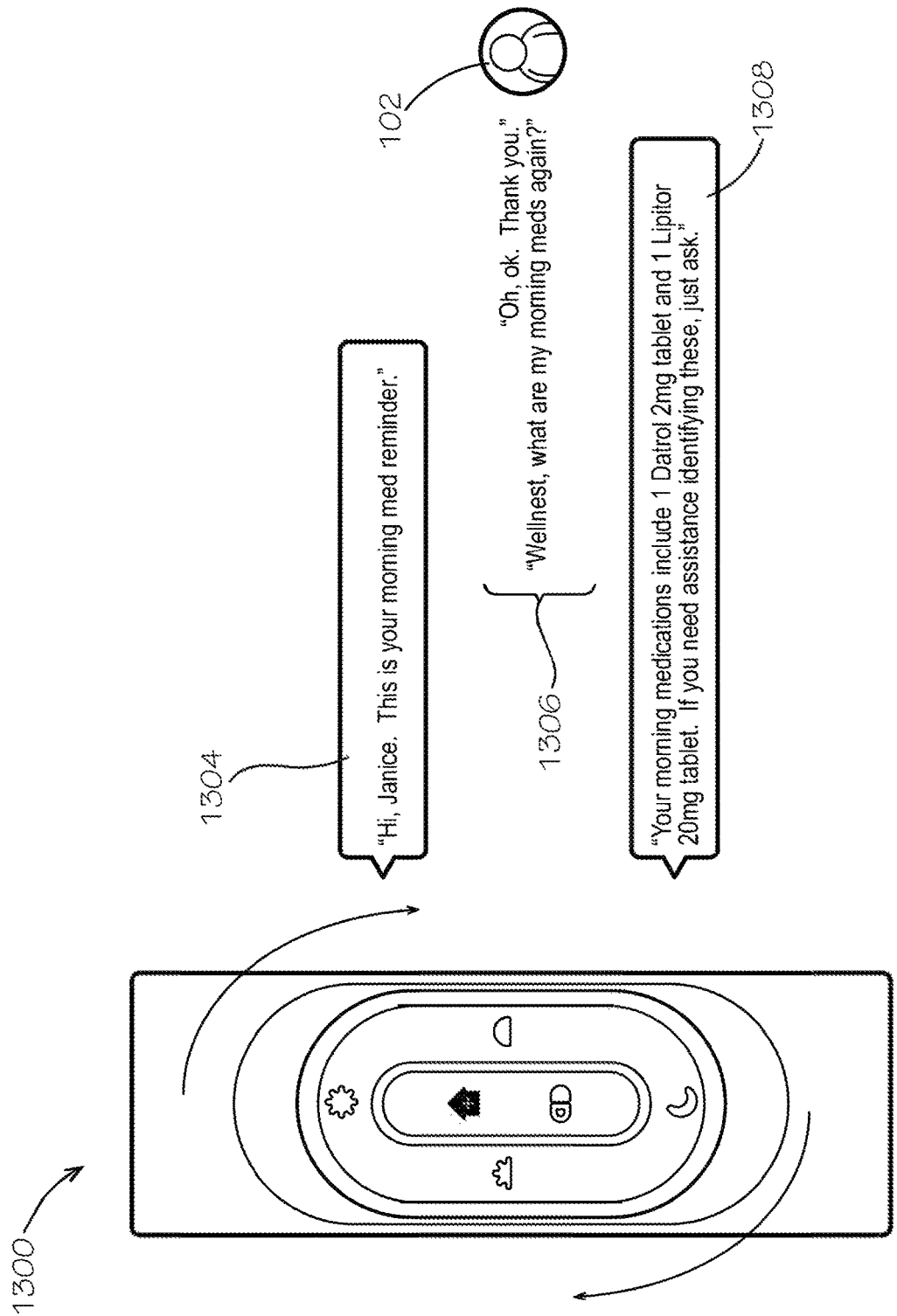

FIG. 13A exemplifies the very first dialog that can occur after the patient 102 (referred to as Janice in the illustrated exemplary dialog) wakes the device 1300 by, for example, giving a single tap to the housing 1302 of the device 1300, the single tap detected by the accelerometer 716, as discussed above with regarding to FIG. 7A. This activation occurs after an individual member of the patient 102's care group 106 (referred to as Hanna in the illustrated exemplary dialog) has set up an account for the patient 102's device 1300 in the manner to be discussed herein with regard to FIGS. 20A-20T. In the dialog shown, the device 1300 introduces the patient 102 to some of the functions that can be performed by the device 1300.

FIG. 13B illustrates a verbal reminder notification for the patient 102 to take a prescribed medication at a time known by the database server 124 in the interactive notification system 104 (FIG. 1) through the aforementioned account set-up procedure. As shown in FIG. 13B, the reminder notification can comprise a routine, recurring statement 1304 used for morning reminders. Then when asked at 1306 what the morning medications are, the device 1300 issues a vocal reply 1308 identifying each morning medication along with corresponding dosages.

Figure 13C:
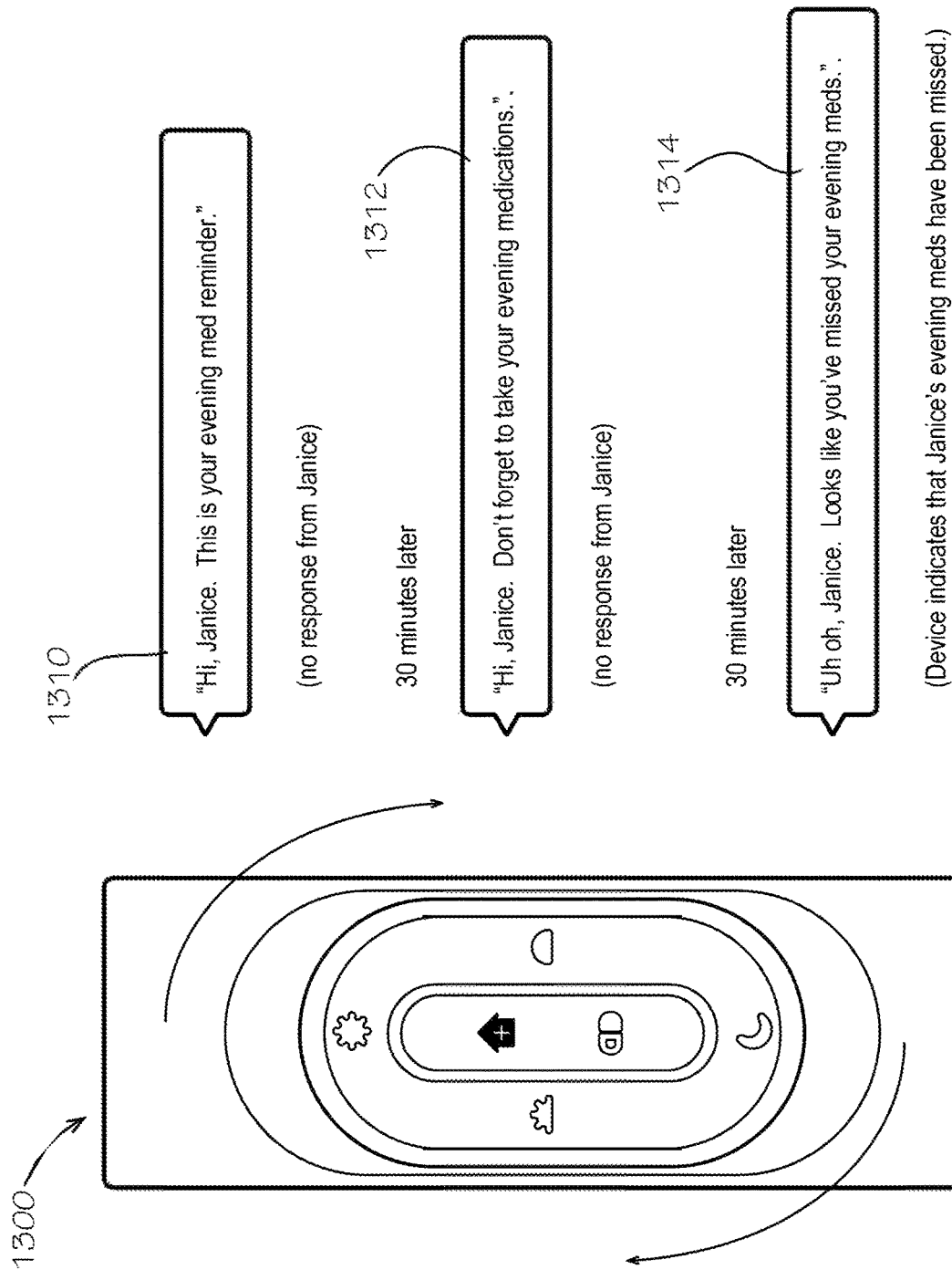

The dialog of FIG. 13C exemplifies another dialog starting with a medicine reminder notification 1310, this time involving an evening medication, but showing what happens upon the failure of the patient 102 to vocalize a responsive utterance to the initial notification. Upon expiration of a predetermined period (for example, thirty minutes in FIG. 13C) without a verbal utterance from the patient 102 or without the press of the primary upper button 710 (FIG. 7A) to confirm the taking of the medication, the device 1300 is shown issuing a second verbal reminder 1312 about the evening medication. Upon expiration of another predetermined period (for example, another thirty minutes in FIG. 13C), the device 1300 broadcasts a verbal statement 1314 indicating that it is apparent that the patient 102 has forgotten to take the scheduled dosage of evening medications.

Figure 13D:
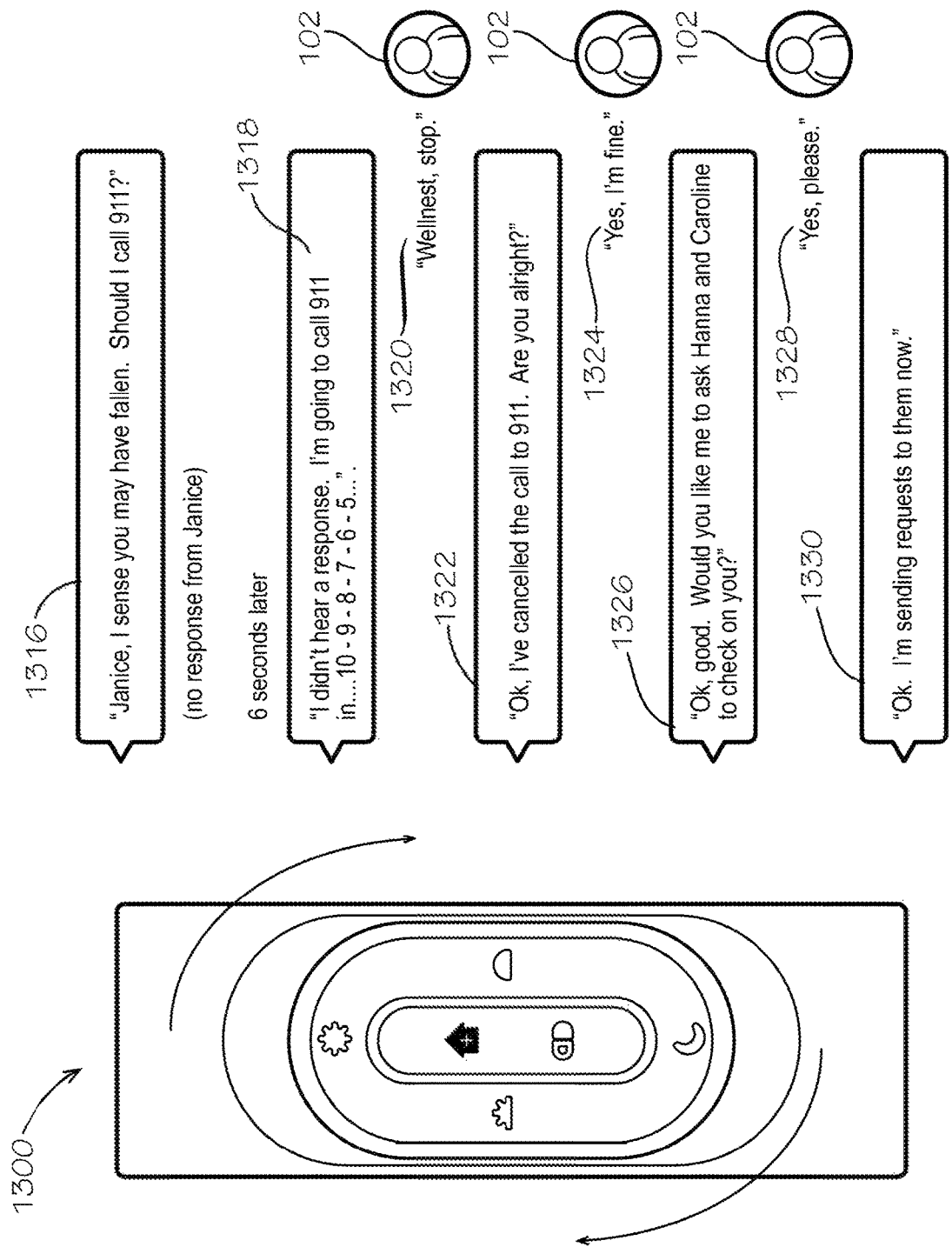

The dialog of FIG. 13D can occur upon detection by the accelerometer 716 (FIG. 7A) of an apparent free-fall condition. Upon such detection, the device 1300 issues a verbal communication 1316 first indicating that a free-fall condition was sensed and then asking whether the device 1300 should place an E911 emergency call. Upon expiration of a short period (such six seconds in the example of FIG. 13D) without a verbal response from the patient 102, the device 1300 issues another verbal communication 1318 indicating that no response from the patient 102 was heard, and that the device 1300 will place an E911 emergency call at the end of a countdown, such as the 10-second countdown initiated in FIG. 13D. The device 1300 then recites the countdown. In the example shown, the patient 102 at 1320, before the countdown expires, gives a command for the device 1300 to stop the countdown. The device 1300 then issues a verbal communication 1322 confirming cancellation of the E911 call and asking the patient 102 whether she is alright. Upon an affirmative reply 1324 from the patient 102, the device 1300 asks a question 1326 as to whether it should ask members of the care group 106 (FIG. 1) to check on the patient 102. Responsive to another affirmative reply 1328 from the patient 102, the device 1300 issues a statement 1330 indicating that it is sending a request to members of the care group 106 to check on the patient 102.

Figure 13E:
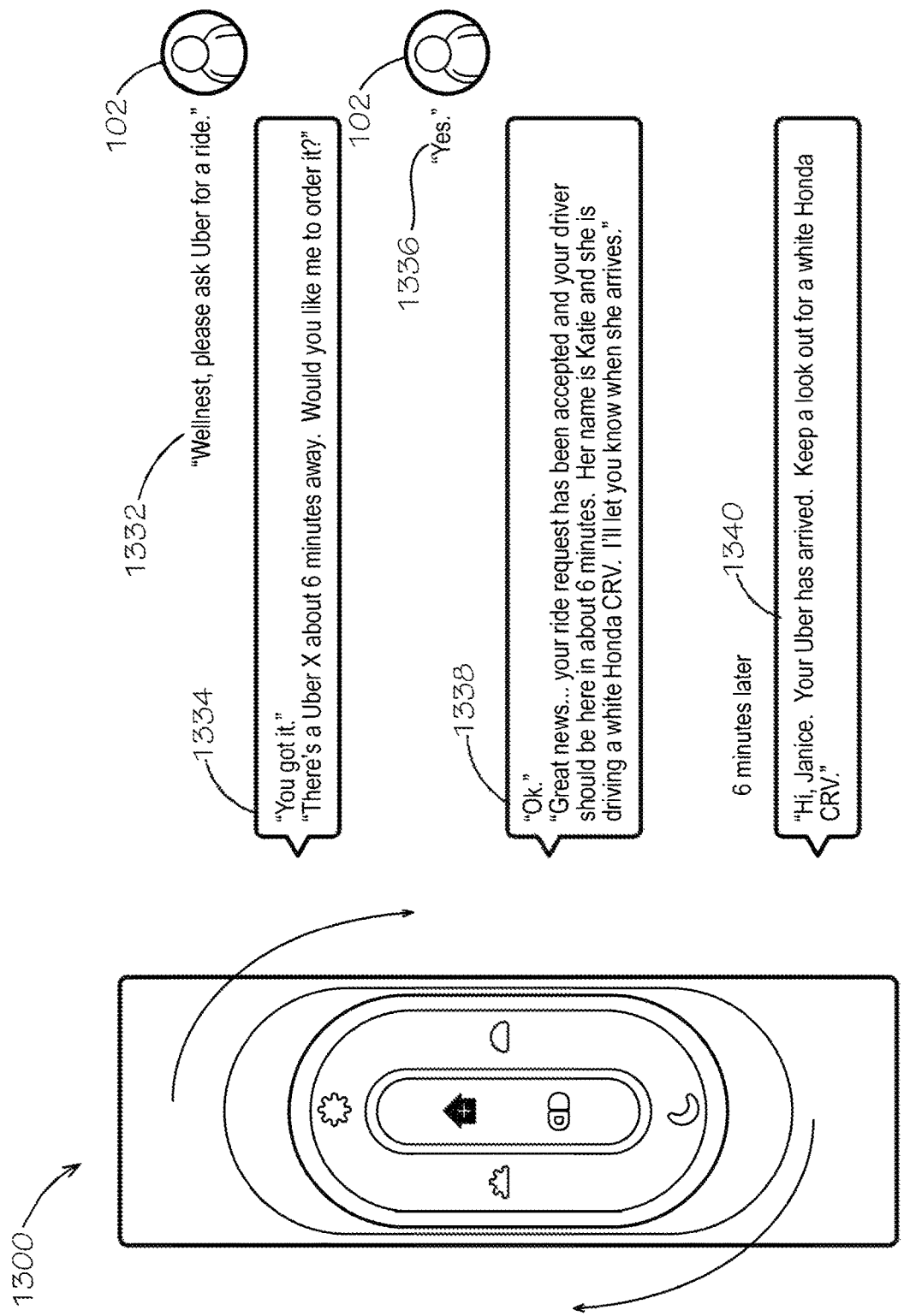

The dialog of FIG. 13E illustrates the ability of the device 1300 to request a ride from a taxi service, such as Uber®, made available Uber Technologies, Inc. of San Francisco, Calif. In such implementations, device 1300 can be configured with a voice translation skill, or a skill for another voice translation service, that allows the voice translation service 126 (such as AVS) to communicate with an Uber® application. The request is designed to have the patient 102 driven to the office of his/her doctor. In the present disclosure, only Uber® is discussed for exemplary purposes since it implements an application, downloadable on both smartphones and desktop and laptop computers, making use of GPS technology. However, it is to be understood that other taxi services with similar capabilities can also be used in other implementations of the present disclosure. As will be described herein with regard to FIGS. 20R and 20S, an Uber® account, whether preexisting or created during the set-up process, can be linked to the device 1300 by a member of the care group 106 as part of the account set-up process if that member grants the requested permission. Once so linked, the device 1300, with the Uber application pre-installed in it, is able to access the Uber® account of that care group 106 member when launching the Uber® application to request a ride from Uber®. In FIG. 13E, the patient 102 initiates the ride-requesting process at 1332 by addressing the device 1300 (here, using Applicant's trademark "Wellnest") and asking the device 1300 to request a ride from Uber®. The device 1300 replies with a confirmatory statement 1334 and proceeds to request the ride by launching the Uber® application. Once its application is launched, Uber® can detect the contemporaneous geographic location of the wearable interactive notification device 100 due to the GPS capabilities provided by the GNSS antenna 704 (FIG. 7A). Uber® sends an SMS communication to the device 1300 informing the communication recipient of how far the driver is from the device 1300. The cellular modem 700 relays this text to the database server 124, which then sends it to the voice recognition service 126, where the text is recognized by the voice control service. The voice recognition service 126 sends to the database server 124 a signal corresponding to a verbal reading of the SMS message. The database server 124 forwards the signal to the wearable interactive notification device 100, where the signal is decoded by the audio CODEC 712 and then broadcast by the speaker 730 of the device 1300 in the manner described above with regard to FIG. 7A. At this point, the device 1300, at 1334, verbally informs the patient 102 of the contemporaneous distance to the nearest Uber® driver, and asks the patient 102 whether he/she would like the device 1300 to order the ride. Upon an affirmative response 1336 from the patient 102, the device 1300 places the order for the ride. If Uber® accepts the order, Uber® sends to the device 1300 an SMS message providing details of the driver, his/her name, and the type of car he/she drives. This SMS message is processed in the same manner as the first SMS message described above, and the device 1300 verbally broadcasts the information contained in the SMS message at 1338. Finally, when the ride has arrived at the location of the patient 102, Uber® sends a final SMS message, which is then relayed verbally at 1340 to the patient 102 in the same manner as the preceding SMS messages from Uber®.

Docking Station Overview and Hardware

Figure 14C:
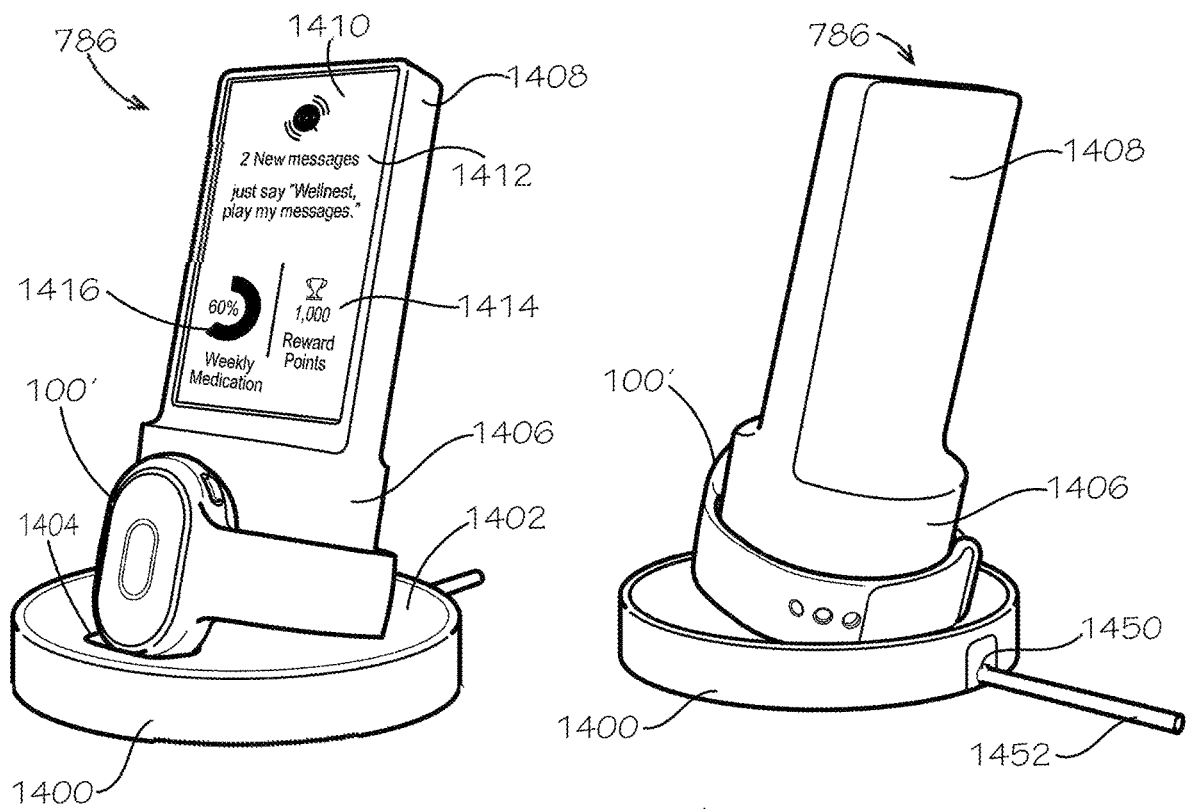
Figure 14C:
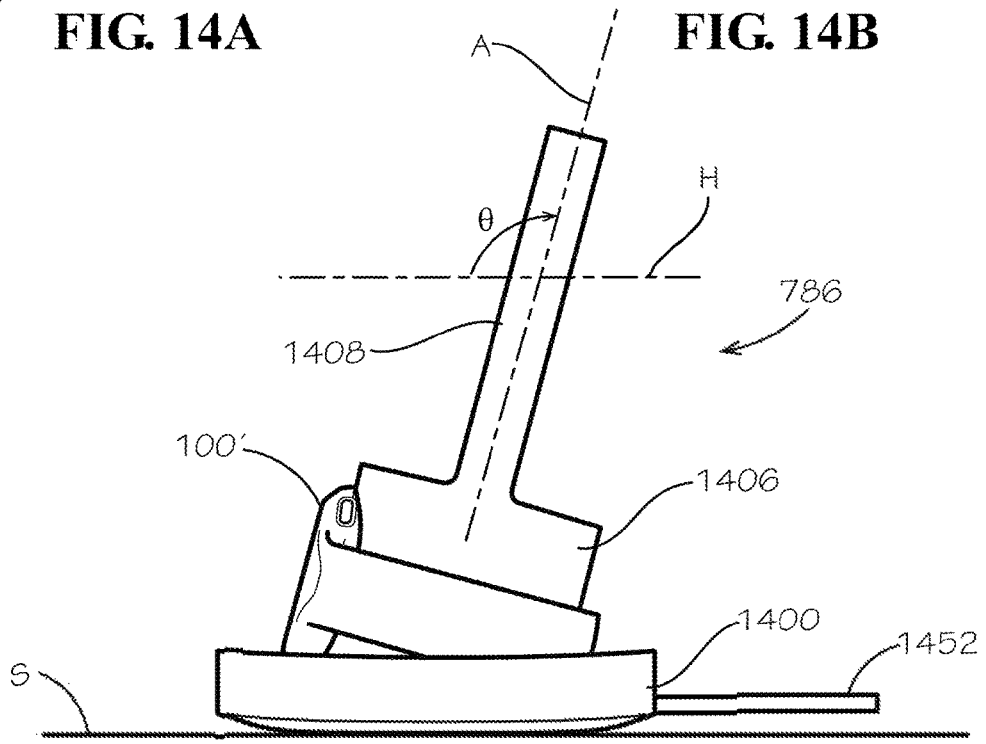

FIGS. 14A, 14B, and 14C are front perspective, rear perspective, and side views, respectively, illustrating the docking of a wearable interactive notification device 100' on the docking station 786. Docking station 786 includes a base 1400 having an upper surface 1402 defining a recess 1404 therein. When the wearable interactive notification device 100' is fully docked as shown in FIG. 14A, for instance, a portion of the wearable interactive notification device 100' is received in the recess 1404. Docking station 786 further includes a pedestal portion 1406 extending upwardly from the base 1400 such that its profile axis of symmetry A (FIG. 14C) makes an obtuse angle θ with an imaginary horizontal line H, and thus with the surface S on which the docking station 786 rests. A frame portion 1408 extends upwardly from the pedestal portion 1406 at the same angle θ with an imaginary horizontal line H, and thus frame portion 1408 and pedestal portion 1406 share the same profile axis of symmetry A. Frame portion 1408 and pedestal portion 1406 are shown as being formed of a single piece but they may also be formed as separate pieces. A display 1410 is received in, and supported by, the frame portion 1408. The display 1410 can be an "electronic ink" (black graphics and/or text against a while background) as shown, although other types of displays may be used. The display 1410 is shown in FIG. 14A reciting a caption 1412 reciting a number of new messages received by the wearable interactive notification device 100' but not played by the user, new earned reward points 1414, and medication compliance percentage 1416.

FIGS. 15A and 15B are side views of the wearable interactive notification device 100' in a partially-docked position, with FIG. 15B isolating the wristband frame 302' in relation to a docking station interface (the data input interface) 788 and a retaining mechanism in the docking station 786. To begin to accomplish docking, the segments comprising wristband 306' are separated from another and the wearable interactive notification device 100' is moved backwards, in the direction of arrow 1422, toward the pedestal portion 1406 of the docking station 786. A retaining groove 1405 extends downwardly from the recess 1404 defined by the upper surface 1402 of the base 1400. A spring member 1407 can be received in, and fixed to, the retaining groove 1405. As best seen in FIG. 15B, the pedestal portion 1406 has a wall 1406a and an overhang 1406b extending forwardly from the wall 1406a. A detent 1409 extends downwardly from the overhang 1406b and is configured to have a shape complementary to a circumferential groove 302a' formed into the wristband frame 302'. The data input interface 788 comprises a plurality of pins 789 extending through the wall 1406a. In the implementation herein exemplified, the data input interface has five pins 789, the five pins corresponding to the five contact pads 1018 (FIG. 10A) on the flexible member 1010 attached to the PCB 1002 of the wearable interactive notification device 100'. Referring again to FIG. 15B, when the wristband frame 302' is in the partially-docked position shown, a bottom portion of the wristband frame 302' is received in the recess 1404, but the detent 1409 does not yet engage the circumferential groove 302a', and the pins 789 do not yet contact any portion of the wristband frame 302' or the contact pads contained therein.

FIGS. 15C and 15D are side views of the wearable interactive notification device 100' in a fully-docked position, with FIG. 15D isolating the wristband frame 302' in relation to docking station interface 788 and retaining mechanism of FIGS. 15A and 15B. Referring to 15C, the wearable interactive notification device 100' has been moved further backwards, in the direction of arrow 1424, such that it now fully engages the pedestal portion 1406 of the docking station 786. In particular, as shown in FIG. 15D, the wristband frame 302' contacts the wall 1406a, and the pins 789 of the docking station interface 788 protrude through corresponding apertures in the wristband frame 302' to contact corresponding contact pads 1018 (FIG. 10A). Additionally, the detent 1409 is now received in the circumferential groove 302a', and the wristband frame 302' is biased to maintain that engagement due to the action of the spring member 1407, which contacts a power portion of the wristband frame 302' to bias it upwardly toward the detent 1409. Such a retaining mechanism helps to ensure that in a docked state, the respective interfaces of the wearable interactive notification device 100' and the docking station 786 are fully engaged with one another.

Figure 16:
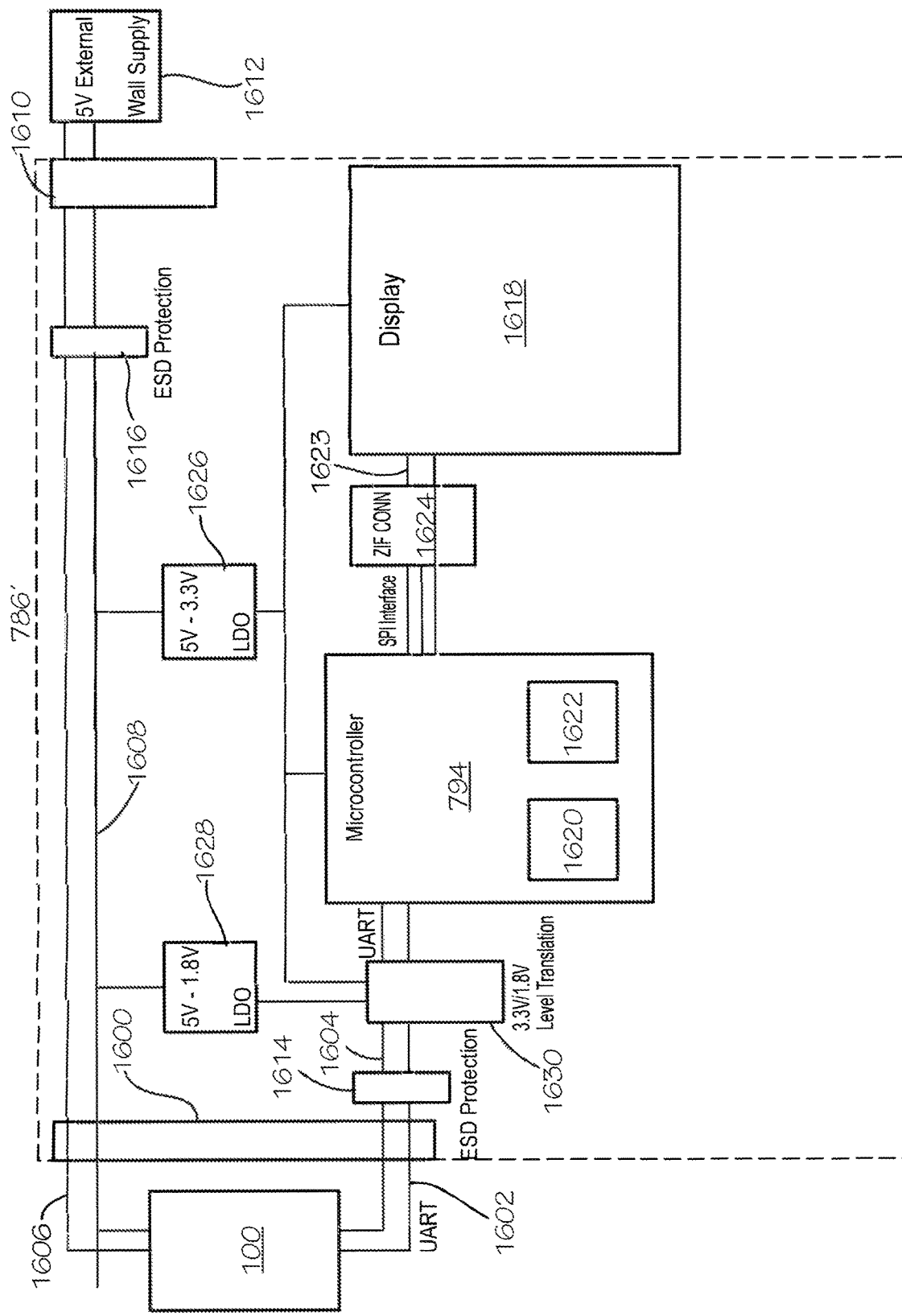
FIG. 16 is a schematic block diagram of exemplary interconnected hardware components of a docking station for a wearable interactive notification device according to an aspect of the present disclosure.

FIG. 16 is a schematic block diagram of exemplary interconnected hardware components of a docking station 786' according to another aspect of the present disclosure. A data input interface (docking station interface) 1600 is shown in FIG. 16 communicating with the wearable interactive notification device 100 to schematically represent the docked state illustrated in perspective in FIGS. 14A-14C. However, in FIG. 16, to illustrate another embodiment, data input interface 1600 comprises a 4-pin connector instead of the five pins illustrated in FIGS. 15B and 15D: two pins for respective data communication lines/interfaces 1602, 1604, one for a power line 1606, and one for a ground line 1608.

It is to be understood that in a five-pin arrangement, a pin for docketing detection, with a corresponding line, would be added to the four aforementioned pins. Opposite the data input interface 1600, the power line 1606 and the ground line 1608 connect to an electrical interface 1610, which in various implementations can comprise a micro-USB interface. The electrical interface 1610, in turn, electrically communicates with an adapter 1612 (sometimes referred to as a "wall adapter"), which provides an AC-to-DC power conversion to supply a predetermined direct voltage (5V, in this example) to the docking station 786'. In the docked arrangement, each pin would be received within a corresponding aperture, or receptacle, formed into the data output interface 782 (FIG. 7A) of the wearable interactive notification device 100. The docking station 786' can be provided with Electro-Static Discharge (ESD) protectors 1614, 1616 to protect downstream components within the docking station 786'. A microcontroller 794 can be configured to: (a) manage communication to the wearable interactive notification device 100; (b) queue image update information and communicate the updated information to a docking station display 1618 (which can, in some implementations, be configured as shown in FIG. 14A at 1410); (c) store display icons and text libraries in a memory resource; and (d) provide manufacturing test support. In the docked arrangement shown, the microcontroller 794 communicates with the wearable interactive notification device 100 via UART interfaces 1602,1604, though these exemplary UART interfaces are not meant to be limiting as to the types of interfaces that may be used. In various implementations, the microcontroller 794 contains flash memory 1620 of at least 64 kB and RAM 1622 of at least 8 kB, and has at least one dedicated UART interface 1602,1604 (for communicating with the wearable interactive notification device 100) and at least one dedicated Serial Peripheral Interface (SPI) 1623 for communicating with the display 1618, optionally via a Zero Insertion Force (ZIF) connector 1624. In the example implementation discussed above with regard to FIG. 14, the display 1618 operates at 3.3V for the SPI 1623. Thus, a first LDO 1626 can be used to reduce the input 5V to an output of 3.3V for appropriate powering of both the display 1618 and the microcontroller 794. Furthermore, because the cellular modem 700 in the wearable interactive notification device 100 operates at a different voltage (such as the 1.8V mentioned above with regard to FIG. 7A) for the UART interfaces 1602,1604, a second LDO 1628 can be used to reduce the input 5V to an output of 1.8V. A voltage-level translator 1630 allows the 3.3V-powered microcontroller 794 to communicate with the 1.8V UART interfaces 1602, 1604.

It will be appreciated that the structure and/or functionality of the docking station 786' may be different than that illustrated in FIG. 16 and described herein. For example, the cellular modem 700 and other components and circuitry of the docking station 786' can be integrated within a common integrated circuit package or distributed among multiple integrated circuit packages. Similarly, the illustrated connection pathways are provided for purposes of illustration and not of limitation, and some components and/or interconnections may be omitted for purposes of clarity. It will be further appreciated that the docking station 786' may not include all of the components shown in FIG. 16, may include other components that are not explicitly shown in FIG. 16 or may utilize an architecture completely different than that shown in FIG. 16.

Docking Station Software

Figure 17:
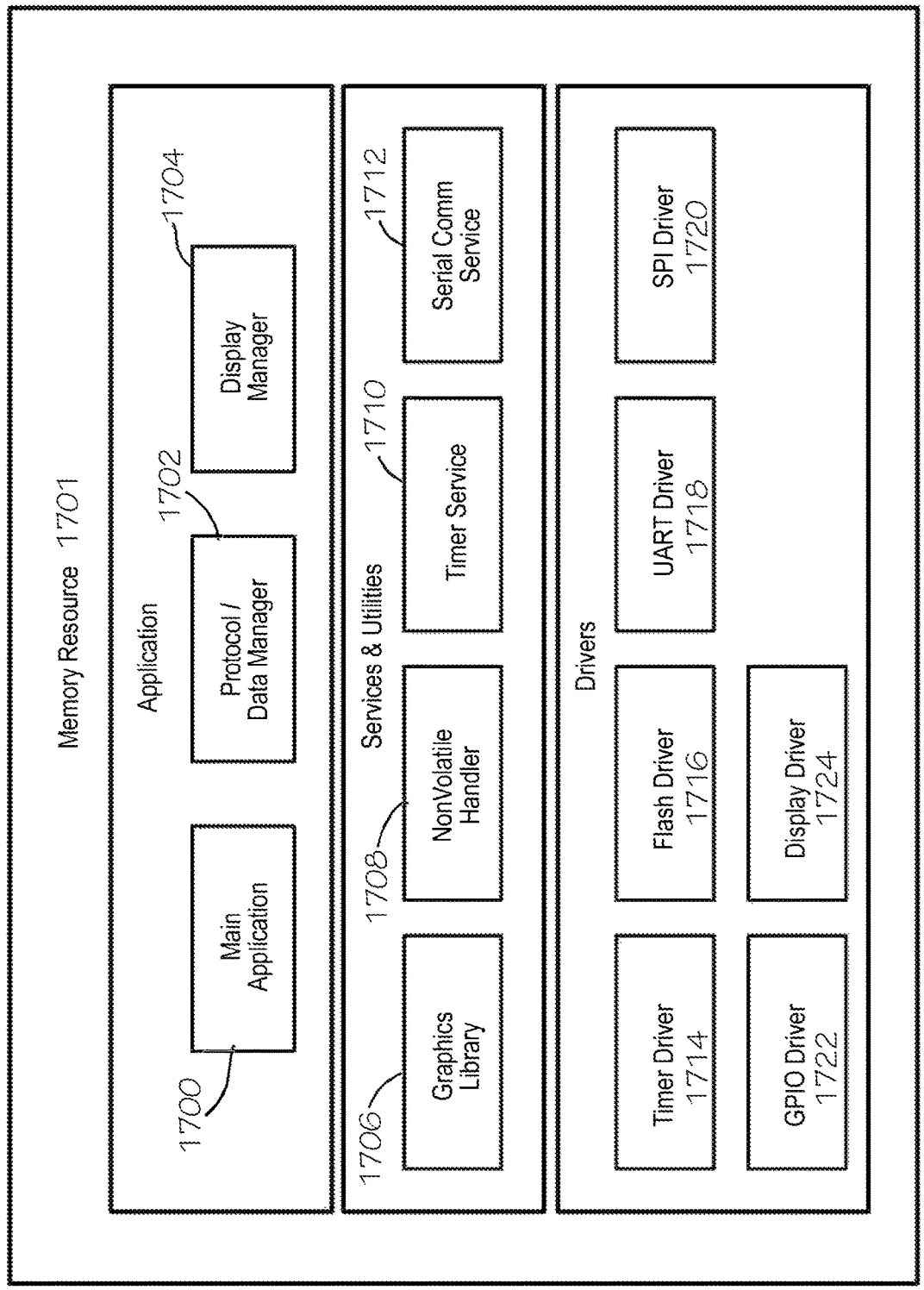
FIG. 17 illustrates an example of a memory resource storing a plurality of modules comprising applications, services and utilities components, and drivers, each module containing processor-executable instructions to operate a docking station for a wearable interactive notification device according to aspects of the present disclosure.

FIG. 17 illustrates an example of a memory resource 1701 storing a plurality of modules comprising applications, services and utilities components, and drivers, each module containing processor-executable instructions to operate the docking station 786' according to aspects of the present disclosure. In the example shown in FIG. 11, the memory resource 1701 shall be understood to diagrammatically represent a combination of the flash memory 1620 and RAM 1622 in the docking station 786' (FIG. 16), such that a given module in the memory resource 1701 may contain data and instructions stored solely in the flash memory 1620, solely in the RAM 1622, or both. However, the memory resource 1701 is not limited to the example of FIG. 17, and in various other implementations can comprise any electronic, magnetic, optical, or other physical storage device that stores executable instructions. In implementations other than those herein disclosed, the memory resource 1701 may take the various other forms discussed above with regard to FIG. 12. Data may be stored on the memory resource 1701 in the same manner discussed above with regard to memory resource 1201 of FIG. 12.

The various modules contained in the memory resource 1701 are now briefly described with reference to FIG. 17.

The Main Application 1700 comprises the main processing loop of the docking station 786'. It will initialize the system, all the managers, services, utilities, and drivers as needed. It is the infrastructure to trigger processing by the Application Managers 1702,1704, and handle events received from cloud and network services such as voice calls, SMS, data, and radio controls. An event could be an action or occurrence recognized by software, often originating asynchronously from an external source or signal, that may be handled by the software.

The Protocol/Data Manager 1702 processes the contents of the data sent to and received from the wearable interactive notification device 100. It can send and receive data directly to/from the Serial Communications Service 1712, which in turn uses the UART Driver 1718. It parses the data contents and makes it available to the Main Application 1700 to determine the execution path based on the data. It also receives data from the Main Application 1700 and formats it into the message structure and passes it back to the wearable interactive notification device 100 through the Serial Communications Service 1712.

The Display Manager 1704 manages the data to be displayed on the display (FIG. 14A at 1410 and FIG. 16 at 1618). It receives the data from the Protocol/Data Manager 1702 and makes use of the Graphics Library 1706 to display the data as desired. It also makes use of the NonVolatile Handler 1708 to maintain static portions of the display image.

The Graphics Library 1706 can comprise non-custom software used to display the data as desired on the display (FIG. 14A at 1410 and FIG. 16 at 1618). It receives data from the Display Manager 1704 and returns a formatted image ready for display.

The NonVolatile Handler 1708 provides application layer control of the nonvolatile data by maintaining the formatting and data structure of the memory resource 1701. It can be accessed by multiple application layer managers to store and retrieve data.

The Timer Service 1710 provides application layer control of the processor timers. It is used by the Main Application 1700 and other Managers to make use of timers as needed. It controls the timers and counters of processors 708 and 794 (FIG. 7A) through the Timer Driver 1714 and maintains higher level management of multiple timers required by the Main Application 1700.

The Serial Communication Service 1712 provides application layer control of the data to be transferred over the UART interfaces 1602,1604 (FIG. 16). The Serial Communication Service 1712 determines when to send data and handles the receiving of data from the wearable interactive notification device 100.

The Timer Driver 1714 directly interfaces with the timers and counters of the processors 708 and 794 (FIG. 7A). It is controlled directly by the Timer Service 1710 to enable/start a processor timer or counter.

The Flash Driver 1716 will directly interface with the flash memory 720 (FIG. 7A) of the wearable interactive notification device 100. The Flash Driver 1716 provides access to read, write, and erase portions of flash memory 720, which is controlled directly by the Non-Volatile Handler 1708. If external flash is required, it will use a SPI or I2C Driver to control the external component.

The UART Driver 1718 directly interfaces with the UART interface 784 (FIG. 7A) of the wearable interactive notification device 100. It handles the low level data flow and control over the UART. The UART Driver 1718 will be controlled by, and respond to, the Serial Communication Service 1712.

The SPI Driver 1720 directly interfaces with the SPI interface 1623 (FIG. 16). It is used by the Display Driver 1724 to handle the data transfer to the display (FIG. 14A at 1410 and FIG. 16 at 1618).

The Display Driver 1724 interfaces with the SPI Driver 1720 to send the image over the SPI 1623 (FIG. 16) to the display (FIG. 14A at 1410 and FIG. 16 at 1618). It is controlled by the Display Manager 1704.

Example of Verbal Dialog with Docked Wearable Interactive Notification Device

Figure 18:
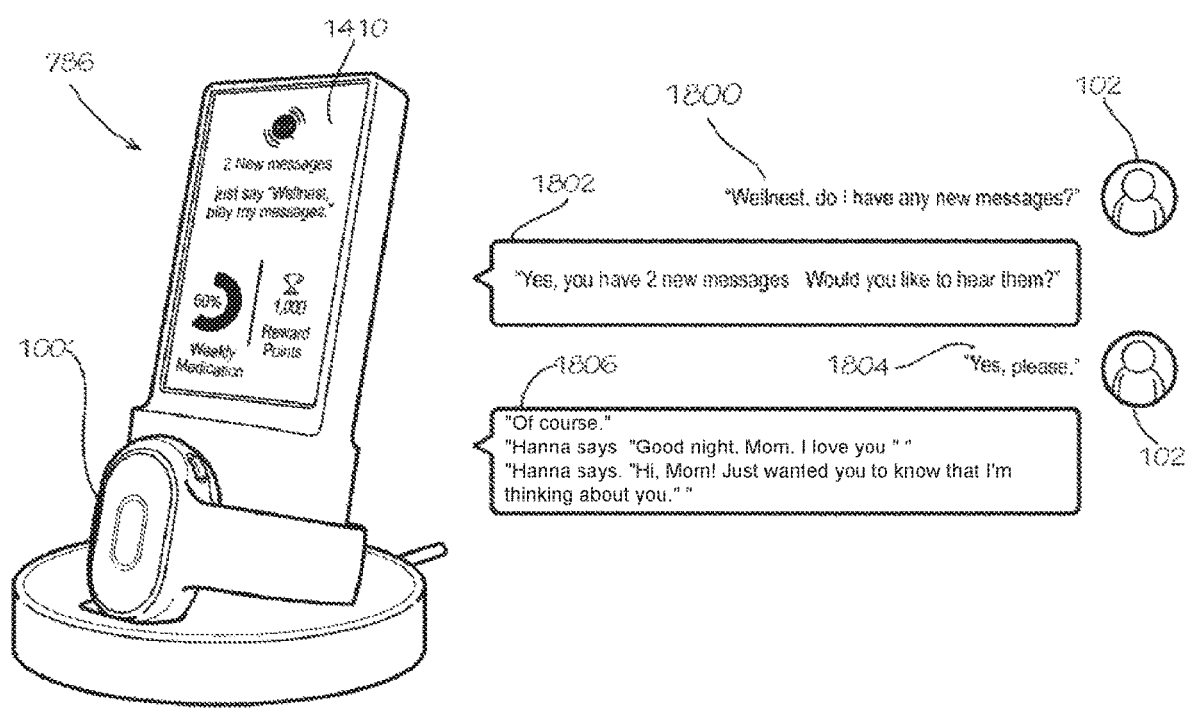
FIG. 18 is a perspective view illustrating a docked wearable interactive notification device according to aspects of the present disclosure, juxtaposed with an example of a verbal dialog between the docked device and a patient using the device.

FIG. 18 is a perspective view illustrating a docked wearable interactive notification device 100' juxtaposed with an example of a verbal dialog between the docked device 100' and a patient 102 using the device 100'. Responsive to a prompt 1800 from the patient 102, the docked wearable interactive notification device 100 issues a communication 1802 informing the patient 102 of the number of new messages detected, that number also being recited in one of the text lines appearing on the display 1410, and also asking the patient 102 whether she would like to hear them. Individuals within the care group 106 of the patient 102 can leave a message on the wearable interactive notification device 100 by sending that device a text message. Once sent, the text message gets stored in the database 226 (see FIG. 22 at entity titled "MESSAGES"). FIG. 18 shows that, upon receiving a "Yes" response 1804, the wearable interactive notification device 100 issues a verbal statement 1806 verbally reciting stored messages left by two persons within the patient's 102's care group 106 (FIG. 1), as well as identifying each individual in the care group 106 who left a message. The capability of the voice recognition service 126 to translate data from text to voice has been described above with regard to FIGS. 1 and 7A.

Figure 19:
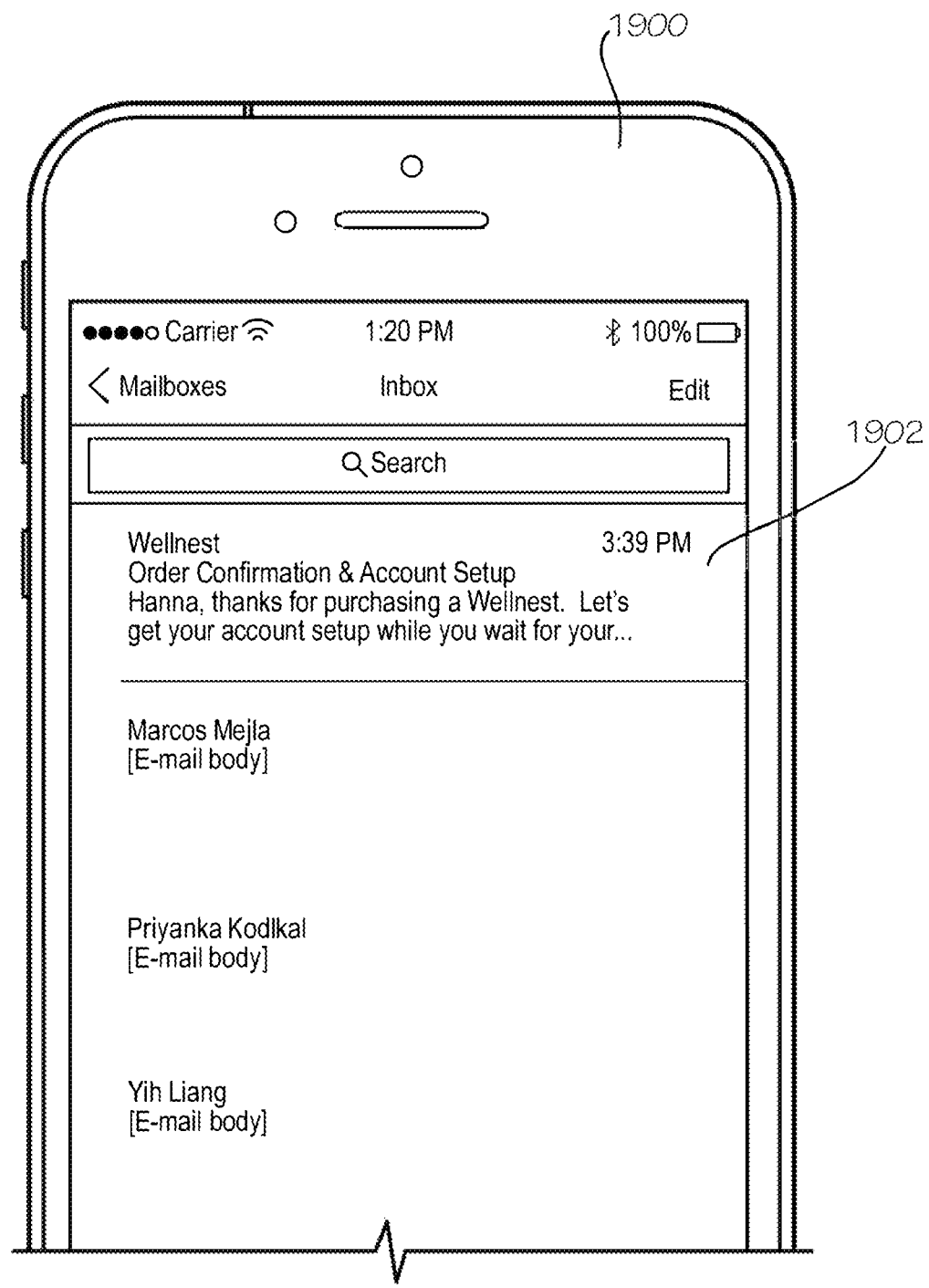
FIG. 19 is a screen diagram illustrating receipt, by an individual member of the patient's care group, of an e-mail from a database server in an interactive notification system according to aspects of the present disclosure.

User Interfaces for Setting Up Accounts for the Wearable Interactive Notification Device FIG. 19 is a screen diagram illustrating receipt, on a cell phone 1900 owned by an individual member of the patient's 102's care group 106, of an e-mail 1902 from the database server 124 in the interactive notification system 104 (FIG. 1). In the example shown, the e-mail 1902 is received by Hanna, one of the persons in the patient's 102's care group 106 (see FIG. 13A). The e-mail 1902 includes a hyperlink to a website where Hanna can enter information to establish an account for the wearable interactive notification device 100, using a series of user interfaces exemplified in FIGS. 20A-20T.

Figure 20C:
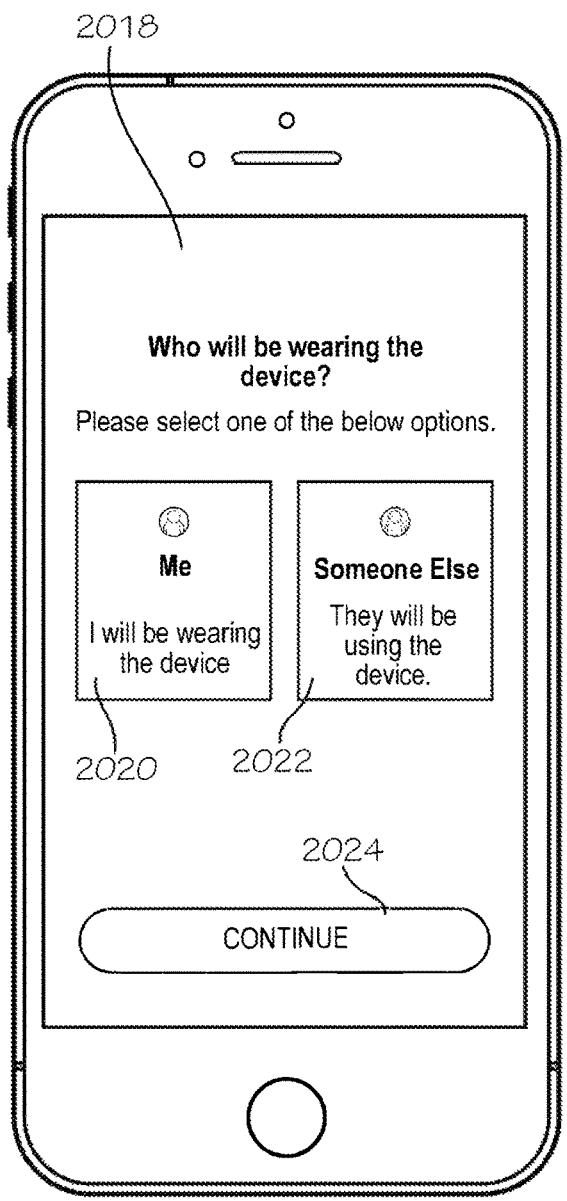
FIGS. 20A-20T illustrate example screen shots demonstrating various aspects of user interfaces presented by an account set-up procedure used for an interactive notification system according to aspects of the present disclosure.
Figure 20D:
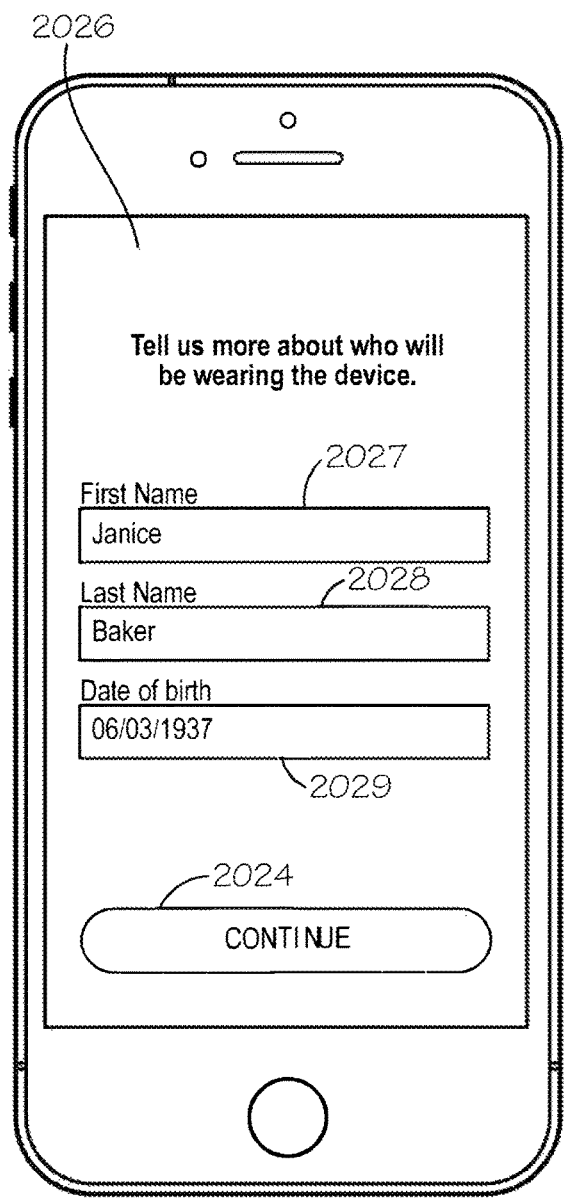
Figure 20E:
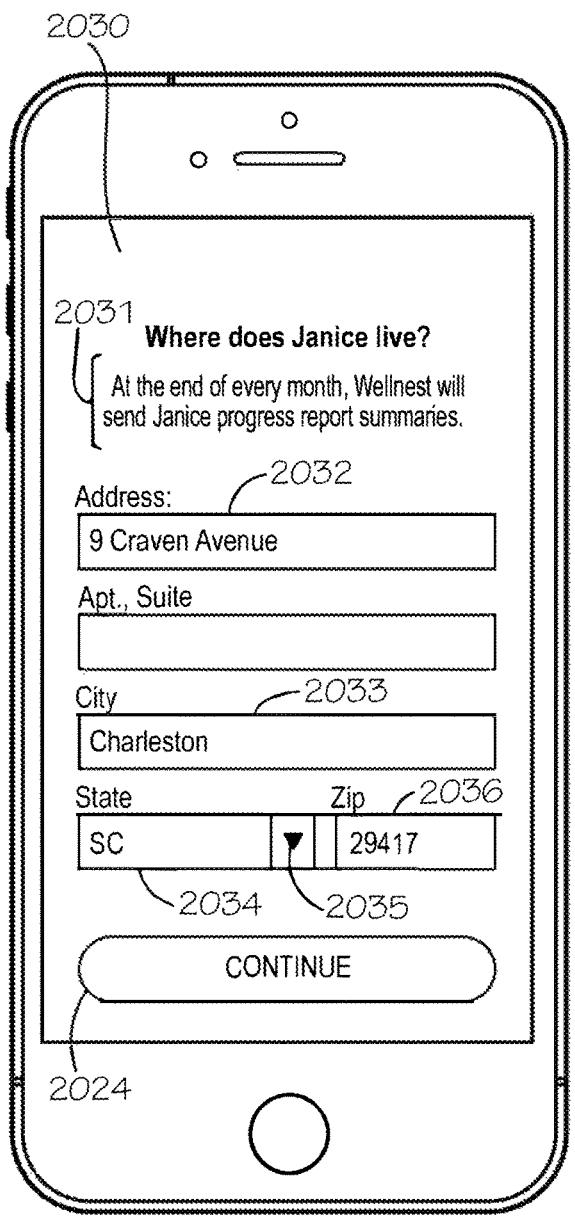
Figure 20F:
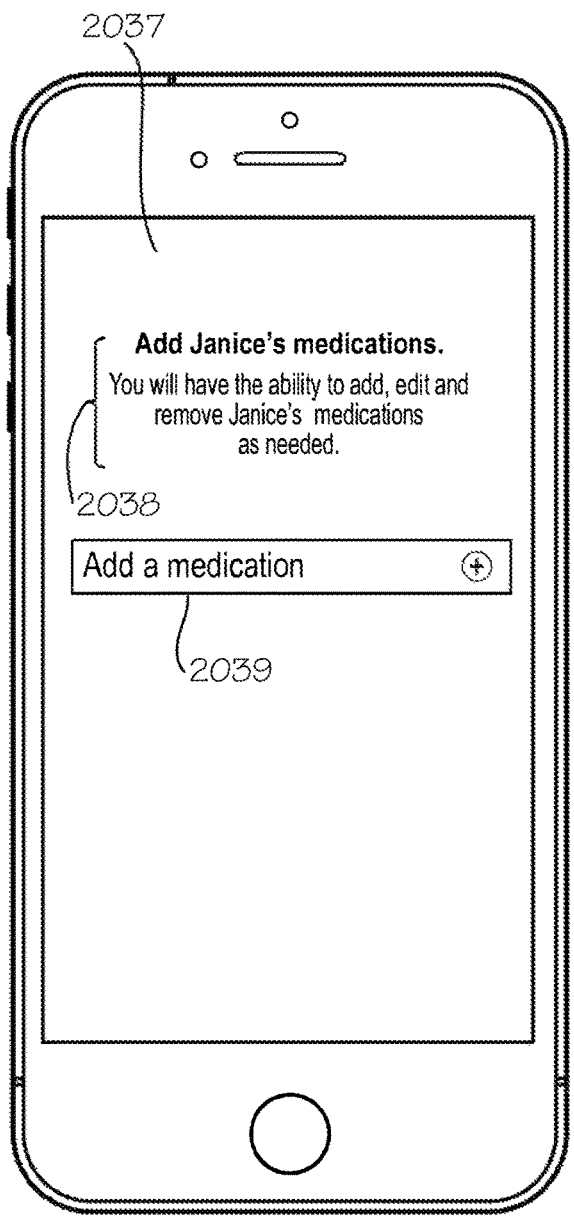
Figure 20G:
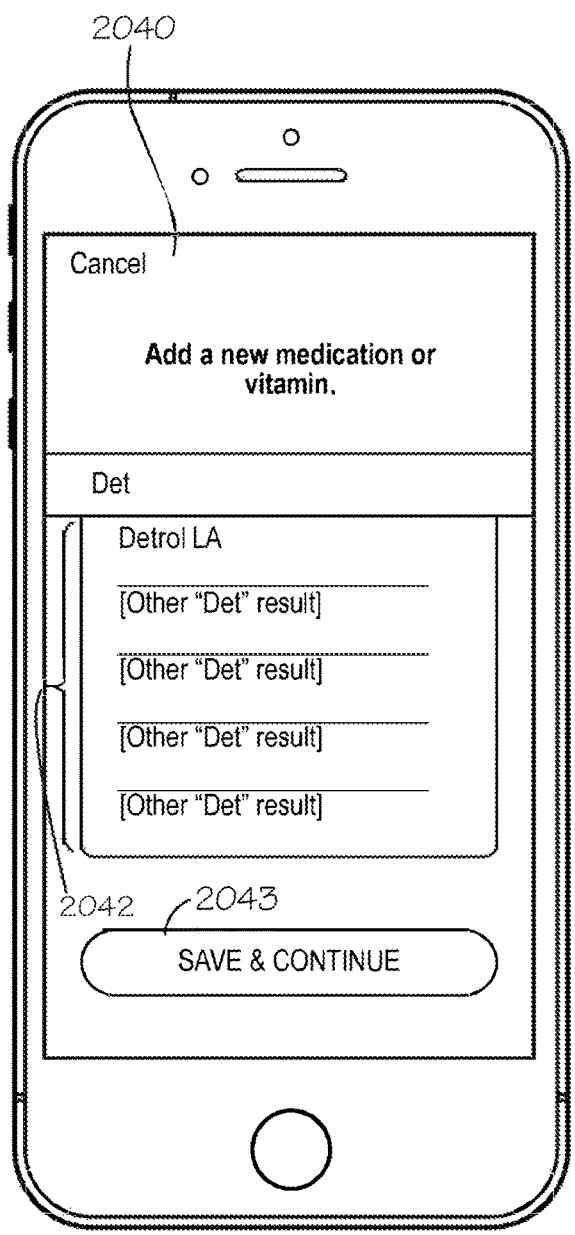
Figure 20H:
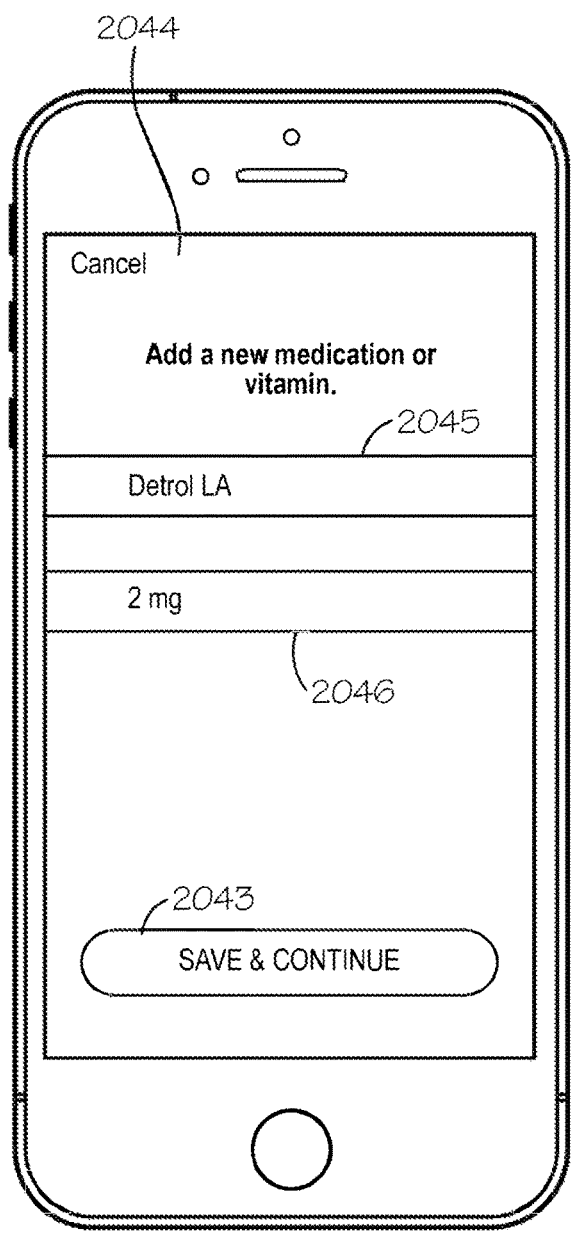
Figure 20I:
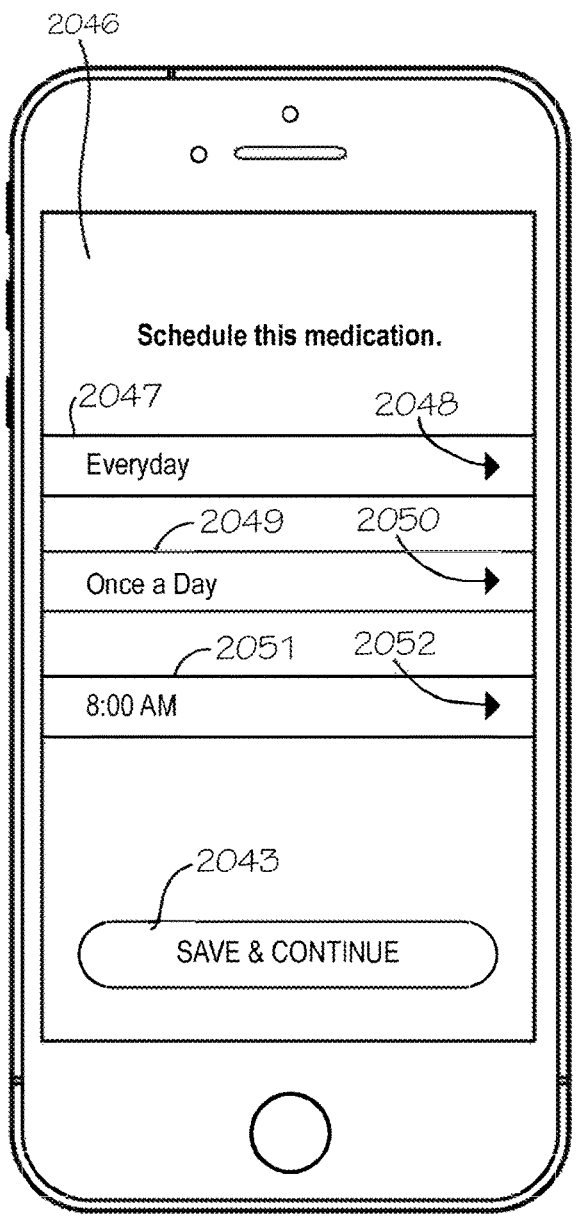
Figure 20J:
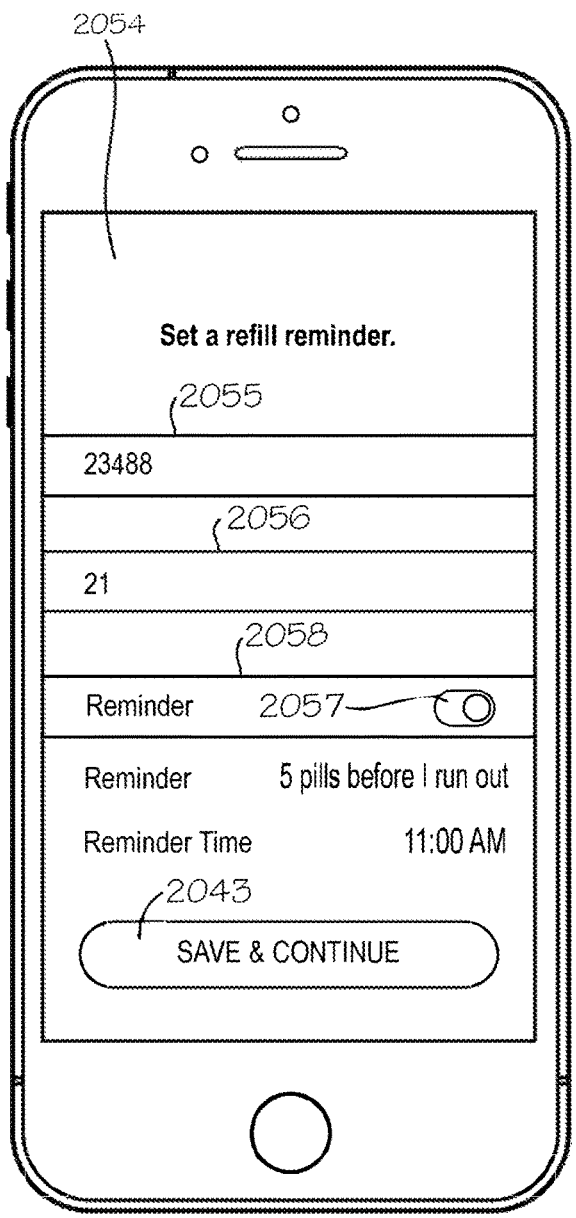
Figure 20K:
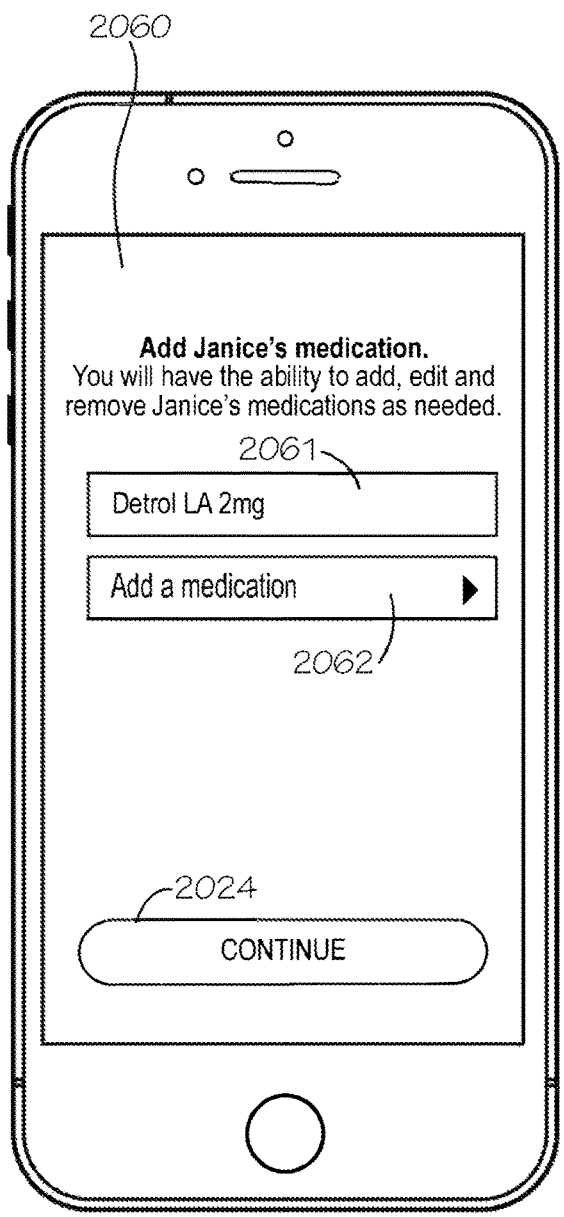
Figure 20L:
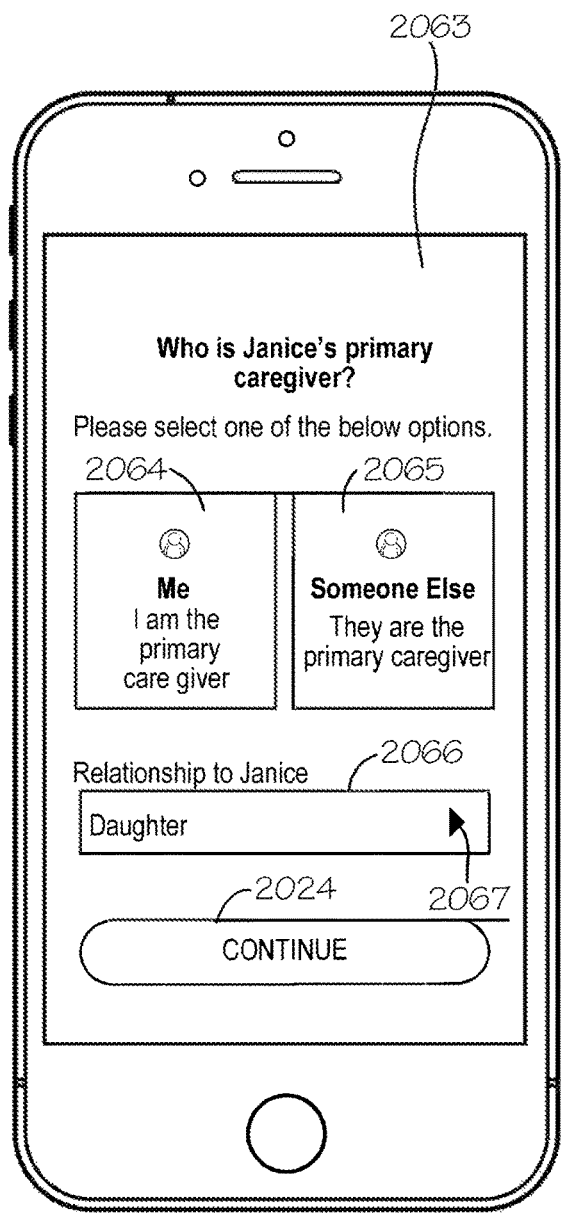
Figure 20O:
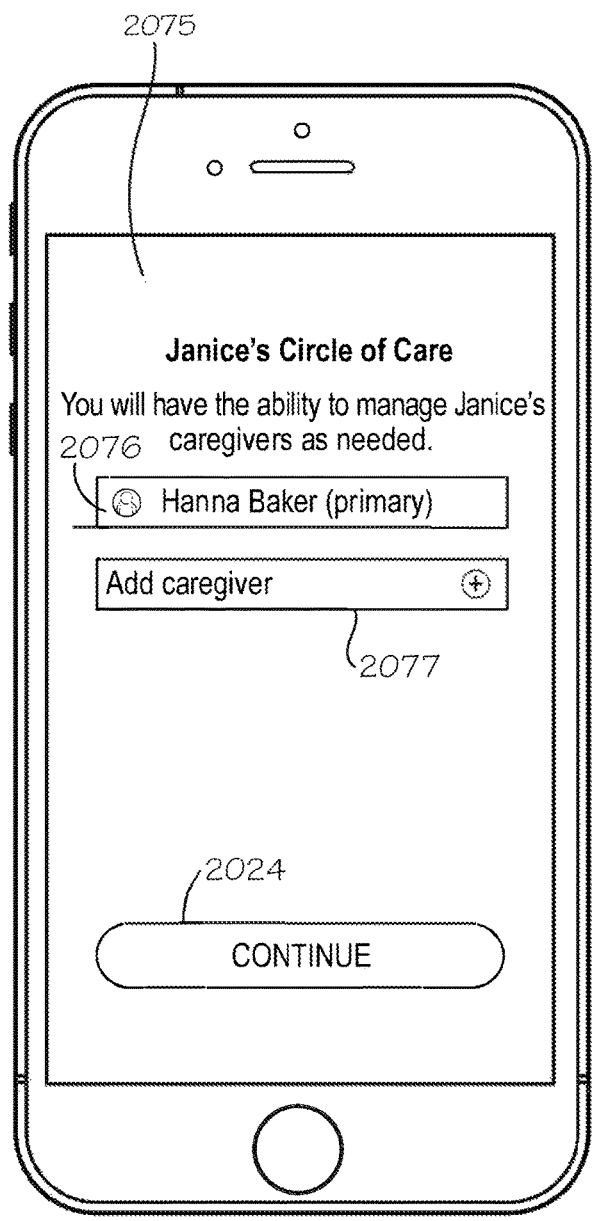
Figure 20P:
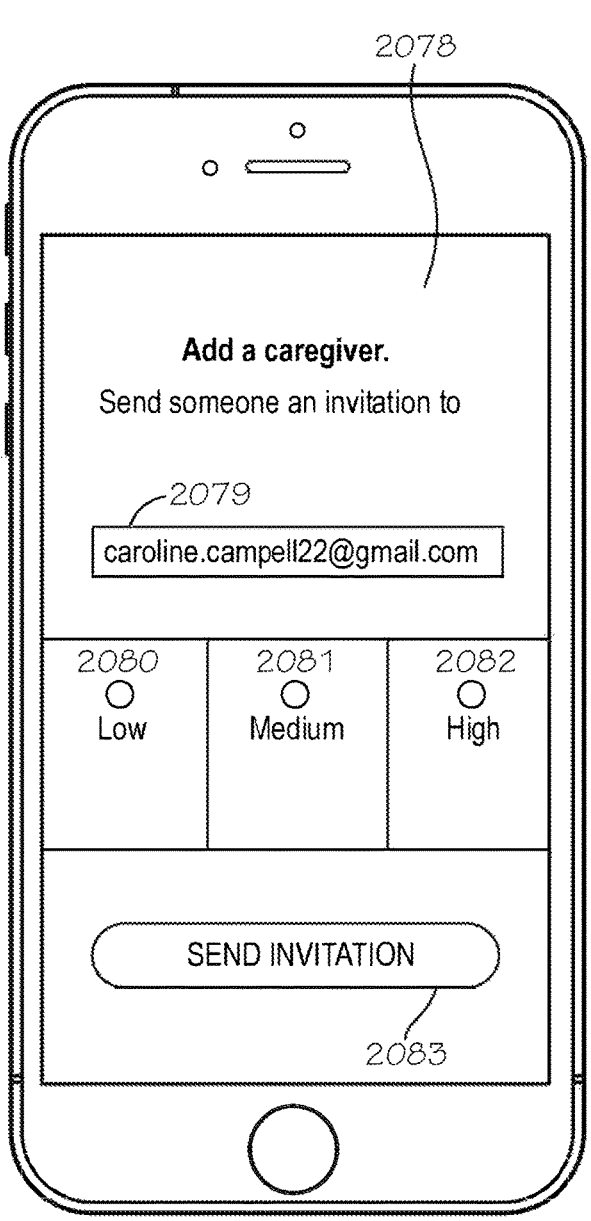
Figure 20S:
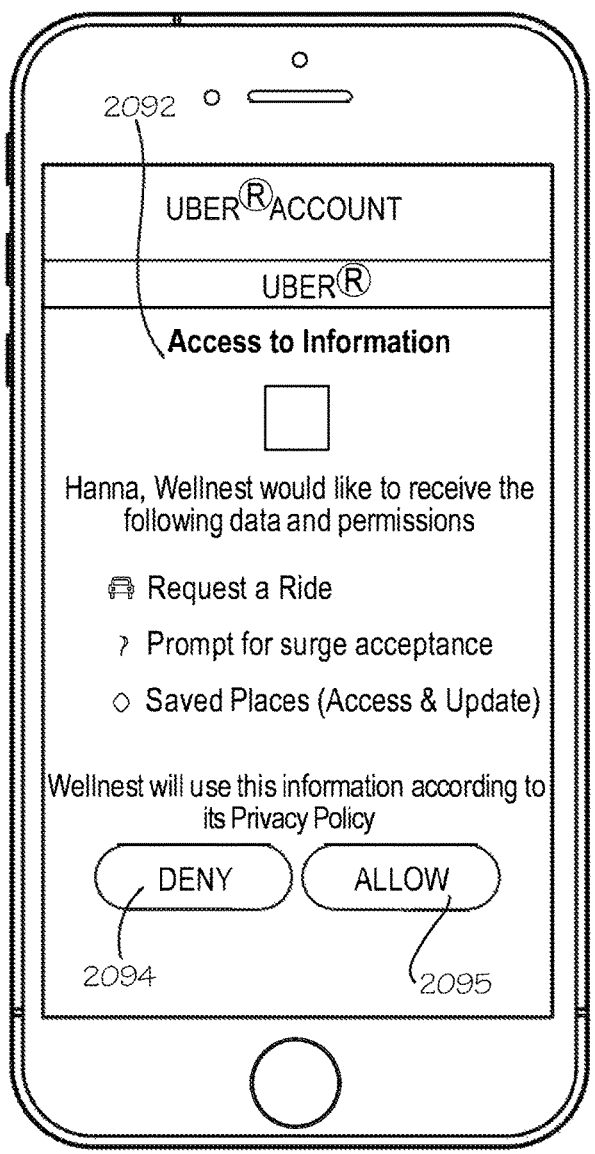
Figure 20T:
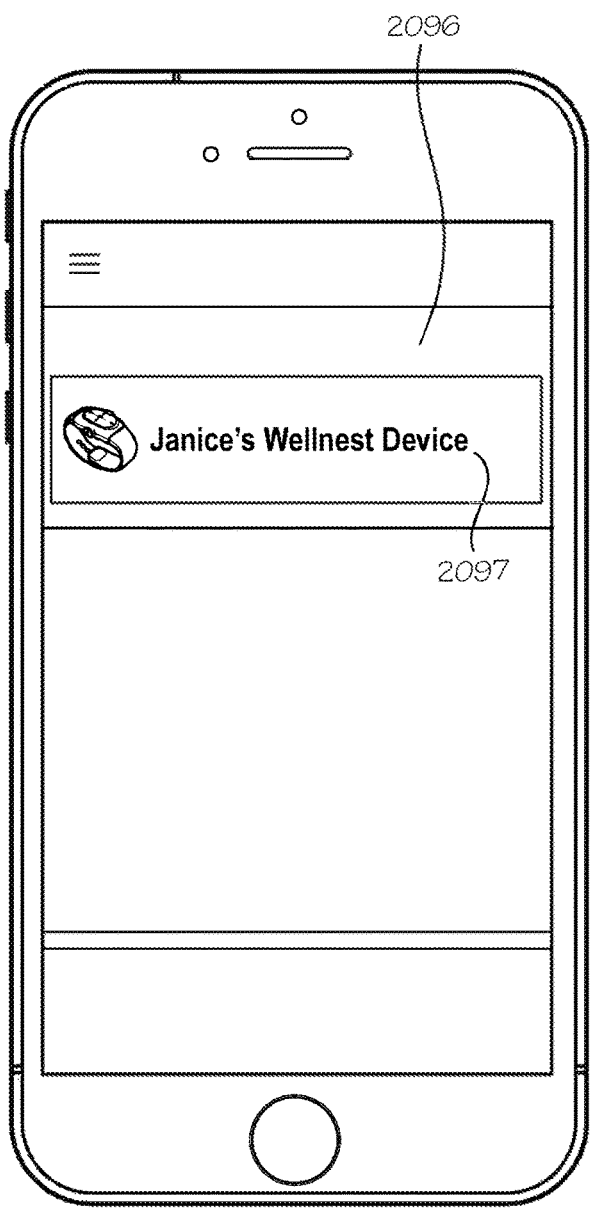

FIGS. 20A-20T illustrate example screen shots demonstrating various aspects of user interfaces presented by an account set-up procedure used for the interactive notification system 104 (FIG. 1).

In the user interface 2000 of FIG. 20A, Hanna enters her first name 2002, last name 2004, and e-mail address 2006, and creates a password 2008. In user interface 2010 (FIG. 20B), Hanna receives a welcome communication 2012, and the user interface 2010 presents Hanna with choices to initiate a setup process by clicking button 2014 or by skipping that process by clicking the caption 2016. In user interface 2018 (FIG. 20C), Hanna can select a box 2020 to set up the account for herself, or select another box 2022 to set up the account for someone else. In the present example, Hanna has selected box 2022. User interface 2018 presents Hanna with the ability to continue the set-up process by clicking the CONTINUE button 2024. The CONTINUE button 2024 recurs in subsequent user interfaces to be described herein, and it will be identified with the same numeral throughout to indicate that it has the same function as described immediately above, i.e., bringing Hanna to the next user interface in sequence. At user interface 2026 (FIG. 20D), since Hanna has elected to set up the account on behalf of another person (here, for example, her mother Janice Baker, who is a patient 102), Hanna enters her mother's first name 2027, last name 2028, and date of birth 2029. At user interface 2030 (FIG. 20E), Hanna enters data concerning her mother's address, i.e., street name 2032, city 2033, state 2034 (which can be selected from a menu by clicking arrow 2035), and zip code 2036. The user interface 2030 can also include a statement 2031 explaining the purpose for requesting the address information.

FIGS. 20F-20K display user interfaces for entry of medication information. An introductory user interface 2037 (FIG. 20F) recites lines of text letting Hanna know that she can begin to enter information about Janice's medications, and informing Hanna of the ability to add and remove medications. Clicking the "Add a medication" button 2039 allows Hanna to enter medication information in ensuing user interfaces. User interface 2040 (FIG. 20G) presents a search box 2041 where Hanna can search for the name of a medication to be added to the account. In the example shown, entering the first few letters brings up a search results list 2042, and Hanna selects the first name in that list, i.e., Detrol®. User interface 2040 presents Hanna with the ability to continue the set-up process by clicking the SAVE & CONTINUE button 2043. The SAVE & CONTINUE button 2043 recurs in subsequent user interfaces to be described herein, and it will be identified with the same numeral throughout to indicate that it has the same function as described immediately above, i.e., saving data just entered in database 226 (FIGS. 2 and 22) and bringing Hanna to the next user interface in sequence. In the example presented, Hanna clicks the SAVE & CONTINUE button 2043, bringing her to user interface 2044 (FIG. 20H), which displays the selected medication in window 2045 and allows Hanna to enter dosage information at box 2046. At user interface 2046 (FIG. 20I), Hanna enters scheduling information for the medication selected in the two preceding user interfaces. At box 2047, by clicking arrow 2048, Hanna is presented with a menu of choices from which she can select a response indicating whether the medication is to be taken every day. At box 2049, by clicking arrow 2050, Hanna is presented with a menu of choices from which she can select the prescribed daily frequency (how many times a day) with which the medication is to be taken. At box 2051, by clicking arrow 2052, Hanna is presented with a menu of choices as to the time of day at which the medication should be taken. At user interface 2054 (FIG. 20J), Hanna enters information regarding medication refills in boxes 2055 and 2056. By clicking on toggle switch/button 2057, Hanna can elect whether the interactive notification system 104 will send refill reminders to Janice. In this example, Hanna has turned that function on with the toggle switch/button 2057, so she is able to enter when the reminder is sent in relation to when pills are scheduled to run out (box 2058) and the time of day at which the reminder should be send (box 2059). At user interface 2060 (FIG. 20K), Hanna is presented with the opportunity to add another medication to the reminder scheme (box 2062) and repeat the same data entry steps for each additional medication as those described above with regard to FIGS. 20G-20I. Box 2061 shows that Detrol® is now a medication included within the reminder scheme.

FIGS. 20L-20Q display user interfaces for adding identifying data for persons to be included within a "Circle of Care," i.e., care group 106 (FIG. 1). At user interface 2063 (FIG. 20L), Hanna can select a box 2064 to indicate that she will be the primary caregiver in the Circle of Care, or select another box 2065 to indicate that someone else will be (or is) the primary caregiver. In this example, Hanna has selected box 2064 to indicate that she will be the primary caregiver. Next, at window 2066, by clicking arrow 2067, Hanna is presented with a menu from which she may select her relationship to Janice; thus, Hanna has selected "daughter." Next, at user interface 2068 (FIG. 20M), Hanna is prompted for her mobile phone number. User interface 2068 can include text 2069 including not only the request itself for that phone number, but also a statement justifying the request, such as that shown, namely: "We will send you important SMS notifications and alerts about your Wellnest wearer." In box 2070, Hanna has entered her mobile phone number. After Hanna clicks the CONTINUE button 2024 of user interface 2068, the database server 124 (FIG. 1) sends an SMS message to Janice's phone reciting a verification code, for security purposes. User interface 2071 (FIG. 20N) displays that SMS message 2072. Instructions 2073 direct Hanna to enter the verification code appearing in the SMS message 2072; thus, Hanna enters that verification code in window 2074. Upon clicking the CONTINUE button 2024 of user interface 2071, Hanna completes the process of adding herself to the Circle of Care. At user interface 2075 (FIG. 20O), Hanna is presented with the option to add other individuals to the Circle of Care (care group 106 of FIG. 1). Box 2076 confirms that Hanna is now a member of that care group 106. By clicking the "Add a caregiver" button 2077, Hanna can proceed with identifying another prospective member of care group 106. If she elects not to add anyone at that time, she can click the CONTINUE button 2024. User interface 2078 (FIG. 20P) appears upon clicking the "Add a caregiver" button 2077 in the preceding interface. In window 2079, Hanna enters the e-mail address of the prospective additional Circle of Care member. Next, Hanna can assign a priority to the prospective additional caregiver, by clicking a radio button above explanatory text, either "Low" (button 2080), "Medium" (button 2081), or "High" (button 2082). Upon clicking the SEND INVITATION button 2083, Hanna causes the database server 124 to send an automated e-mail to the e-mail address entered in box 2079. User interface 2084 (FIG. 20Q) shows at box 2085 that the prospective additional member ("Caroline Campbell") is at "pending" status because initially there is no confirmation that Ms. Campbell has accepted the invitation sent at user interface 2078 (FIG. 20P).

FIGS. 20R and 20S display user interfaces for linking an Uber® account, whether preexisting or created during the set-up process, to the account for the wearable interactive notification device 100. In such implementations, device 100 can be configured with a voice translation skill, or a skill for another voice translation service, that allows the voice translation service 126 (such as AVS) to communicate with an Uber® application. Once so linked, the wearable interactive notification device 100 is able to access Hanna's Uber® account member when launching the Uber® application to request, on behalf of her mother Janice, a ride from Uber®. In user interface 2086 (FIG. 20R), if Hanna already has an Uber® account, she follows the instructions 2087 by entering her Uber® account e-mail address (box 2088) and Uber® account password (box 2089), then clicking the SIGN IN button 2090. If, however, Hanna does yet not have an Uber® account, she can create one by clicking the hyperlink 2091 and initiating subsequent steps at the linked site. By the time Hanna accesses user interface 2092 (FIG. 20S), she now has an Uber® account and is prompted to decide whether she will grant permission for the interactive notification system 104 to access certain data 2093 associated with Hanna's Uber® account. Hanna clicks either the DENY button 2094 or the ALLOW button 2095.

In FIG. 20T, the user interface 2096 appears once Hanna completes the steps to set up the account for the wearable interactive notification device 100. User interface 2096 displays a button 2097 with the caption "Janice's Wellnest Device." Clicking button 2097 will provide Hanna with a separate set of user interfaces associated with Janice's wearable interactive notification device 100.

High-Level Application and Entity Relation Diagrams

Embodiments of the methods and systems are described below with reference to block diagrams of methods, systems, and apparatuses. It will be understood that each block of the block diagrams and flowchart illustrations, and combinations of blocks in the block diagrams and flowchart illustrations, respectively, can be implemented by program instructions. These program instructions may be programmed into programmable processing elements to produce logic that executes on the processing elements to create means for implementing the functions specified in the block or blocks, which describe and reference specific algorithms and inherent structure for accomplishing the functions as described and further explained herein.

These program instructions may also be stored in a processor-readable memory that can direct a processing apparatus to function in a particular manner, such that the instructions stored in the processor-readable memory produce an article of manufacture including processor-readable instructions for implementing the function specified in the block or blocks. The program instructions may also be loaded onto a processing apparatus to cause a series of operational steps to be performed on the programmable apparatus to produce a processor-implemented process such that the instructions that execute on the programmable apparatus provide steps for implementing the functions specified in the block or blocks.

Accordingly, blocks of the block diagrams support combinations of elements for performing the specified functions, combinations of steps for performing the specified functions and program instructions for performing the specified functions. It will also be understood that each block of the block diagrams, and combinations of blocks in the block diagrams, can be implemented by general purpose or special purpose hardware-based systems that perform the specified functions or steps, or combinations of special purpose hardware and instructions.

Figure 21A:
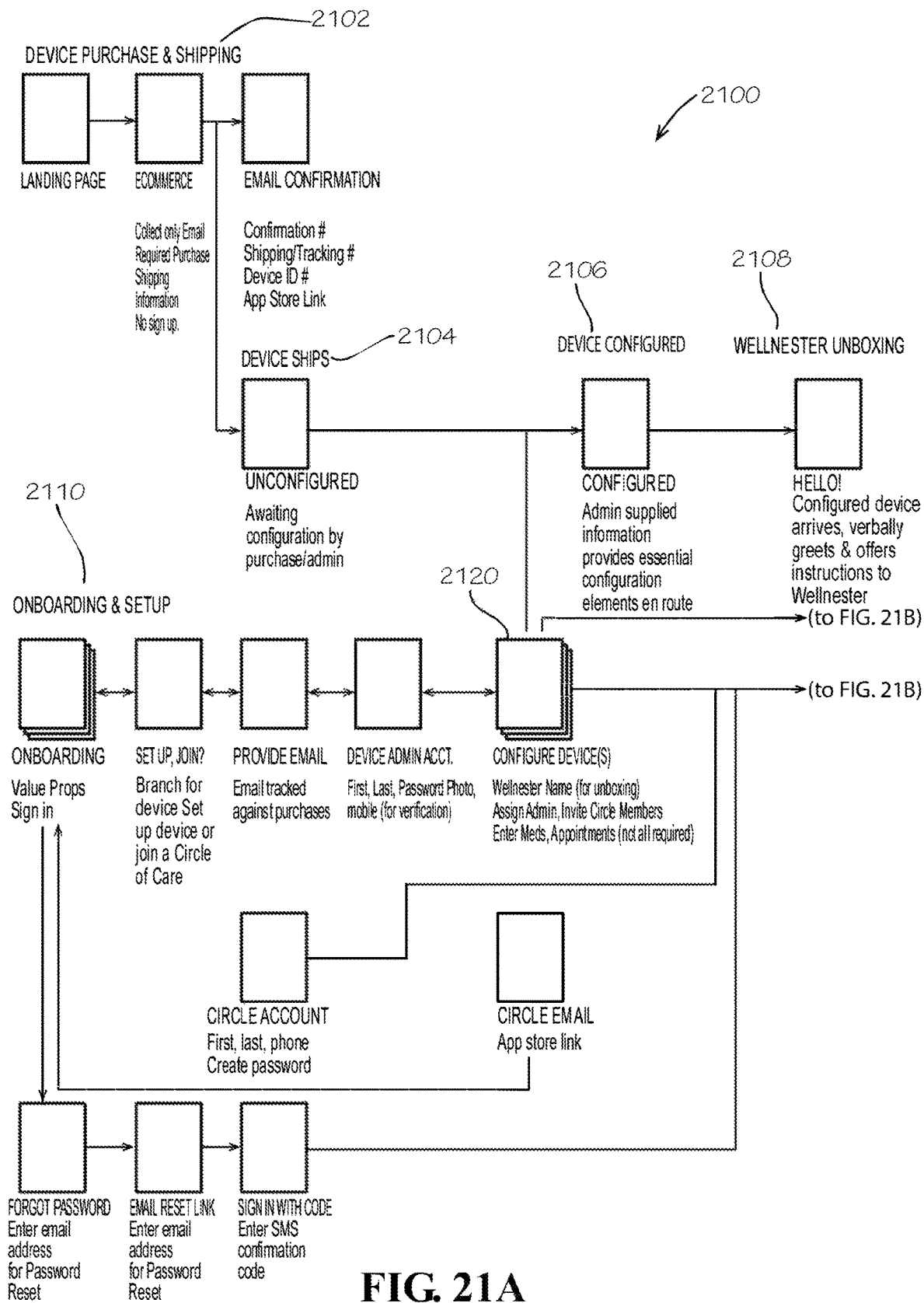
FIGS. 21A-21B comprise a high-level application flow diagram for an interactive notification system according to aspects of the present disclosure.
Figure 21B:
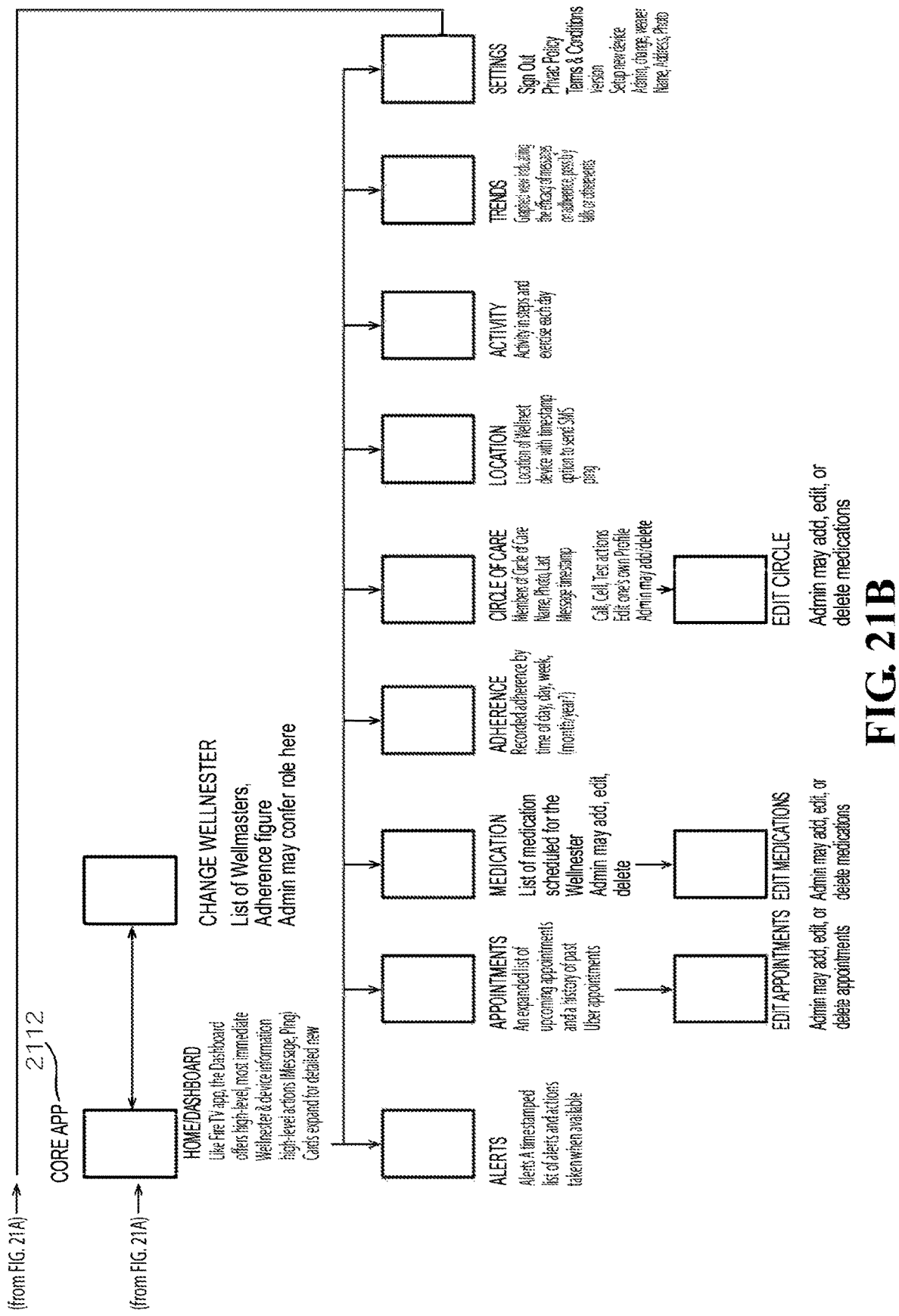

FIGS. 21A and 21B comprise a high-level application flow diagram 2100 for the interactive notification system 104 (FIG. 1). Diagram 2100 is organized under six main headings, or branches: "Device Purchase & Shipping (Web)" (2102), "Device Ships" (2104), "Device Configured" (2106), "Wellnester Unboxing" (2108), "Onboarding & Setup" (2110), and "Core Application" (2112).

Regarding the "Device Configured" branch 2106, since the wearable interactive notification device 100 is a cellular device, it may have up to a 33% charge on its battery while it is in transit from the manufacturer to a patient 102. In some implementations, the wearable interactive notification device 100 is configured to check for new data in the server database 124 four times a day. Thus, in such implementations, the wearable interactive notification device 100 is checking for new data four times a day while it in a courier's delivery truck. That means that after someone in the care group 106 has purchased the device 100 for the patient 102, and has thereafter set up an account for the device 100, such as via the interfaces discussed above with regard to FIGS. 20A-20T, new data is present in the server database 124 and can be retrieved by the device 100 while in transit.

The "Wellnester Unboxing" branch 2108 exemplifies how the set-up of the wearable interactive notification device 100 creates a more personal experience for the patient 102 who receives the wearable interactive notification device 100. By the time the patient receives the wearable interactive notification device 100 and takes it out of its box, the device 100 can immediately start interacting with the patient 102, hence the "HELLO!" caption for event 2108. When it is either taken out of the box, or when some other action occurs that is detected by the accelerometer 716 (FIG. 7A), an interrupt signal is sent by the wearable interactive notification device 100 to the server database 124, which can then send a command to the voice recognition service to send a voice signal to the device 100 corresponding to a greeting, using the patient's 102's name and the purchaser's names since those names were added to the database 226 in the database server 124 during the device set-up process referred to at event 2120 of FIG. 21A and detailed above with regard to FIGS. 20A-20T. Thus, using the names discussed above with regard to FIGS. 20A-20T, above, when Janice takes her wearable interactive notification device 100 out of its box, the wearable interactive notification device 100 could broadcast a verbal greeting to her such as: "Hello, Janice. Welcome to Wellnest. Hanna purchased this device for you and is now in your Circle of Care. I will remind you of your medications." In this manner the interactive notification system 104 creates a personal experience for Janice in her efforts to adhere to her medication schedule.

Figure 22:
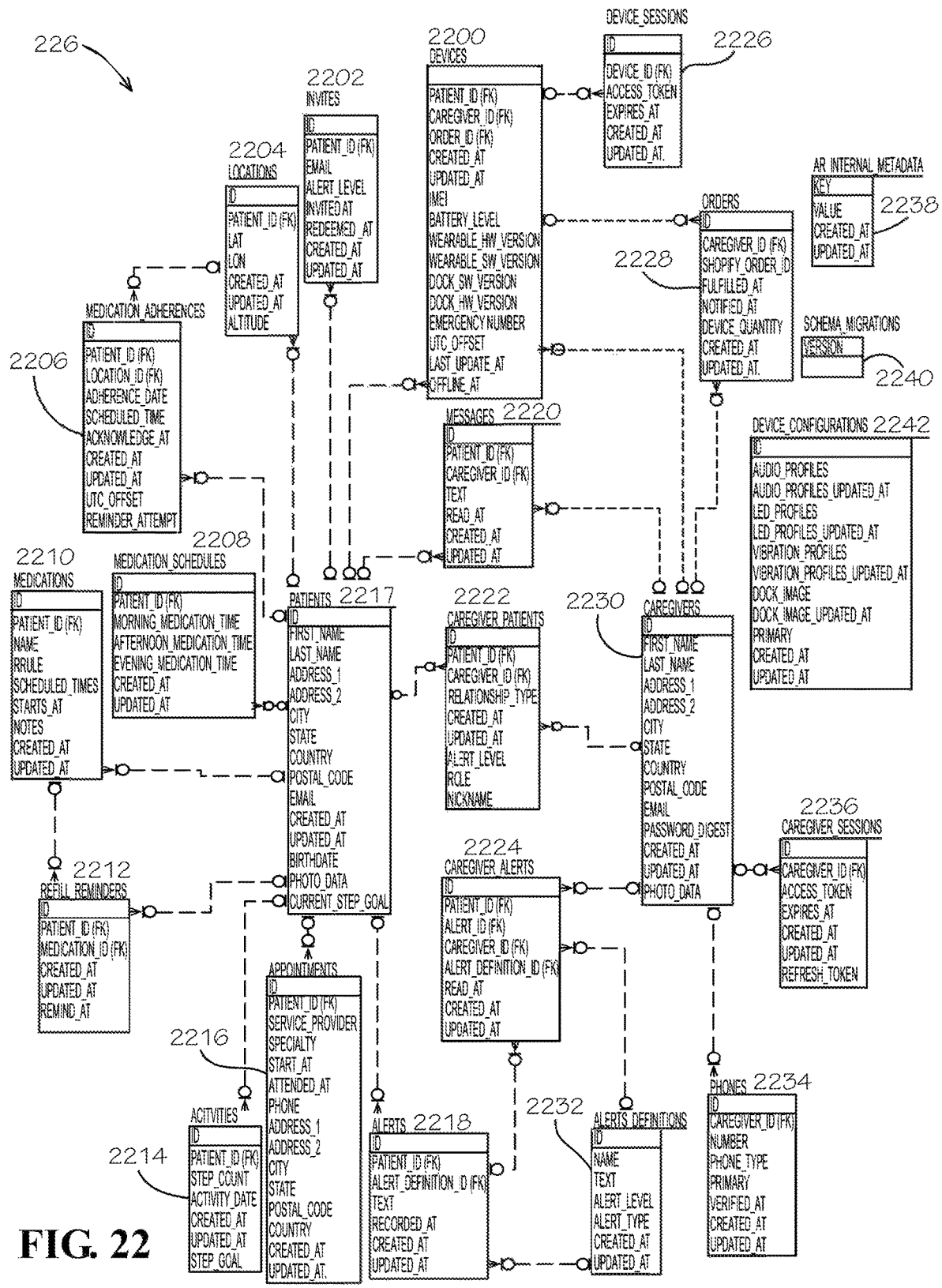
FIG. 22 is an entity relationship diagram illustrating a data model for a database used by or accessible to the interactive notification system, according to some aspects of the present disclosure.

FIG. 22 is an entity relationship diagram illustrating a data model for database 226, according to some aspects of the present disclosure. The database 226 can be implemented with an Oracle® platform, although other platforms can be used, including but not limited to Sysbase®, DB2®, Aurora®, and MS-SQL®. Those of ordinary skill in the relevant art will understand the terminology and symbols recited in FIG. 22, but some description of portions of FIG. 22 are nevertheless provided below to further promote understanding of the information stored within the database 226.

FIG. 22 shows entities 2200-2242, and the relationships between them, with some data items in the entities 2200-2242 being designated as a primary key (PK) or a foreign key (FK), i.e., defined in an entity other than the one in which the (FK) notation is recited. Entity 2200 contains information unique to each wearable interactive notification device 100, including but not limited to the IMEI number. Entity 2200 also contains data indicating the version numbers of the hardware and software comprising wearable interactive notification device 100 and the docking station 786. Entity 2202 reflects data concerning each person invited to be added to the Circle of Care, as discussed above with regard to FIGS. 20O-20R. Entities 2206-2210 contain information regarding the medications of the patient 102, the scheduling of when to take those medications, and record of adherences with such scheduling. Entity 2217 contains much of the patient data entered during the device setup process discussed above. Entity 2232 includes data elements: (i) ALERT_LEVEL, and (ii) ALERT_TYPE. The ALERT_LEVEL data element corresponds to the "Low," "Medium," or "High" designations associated with a Circle of Care member as discussed above with regard to FIG. 20P. The ALERT_TYPE data element categorizes an alert according to type, for example, emergency, a patient's falling, medication alert, and appointment alert. Entity 2230 ("CAREGIVERS") includes the data element PASSWORD_DIGEST. For security reasons, passwords cannot be stored in a database in such a clear form as could be used by a person attempting a security breach. Thus, the passwords are not only encrypted when they are stored, but they are also "salted," meaning that arbitrary data is added to the end of each encrypted password. That way even when two people's passwords are identical, the encrypted versions will be very different from one another. Finally, regarding entity 2228 ("ORDERS"), the NOTIFIED_AT data element represents a timestamp at which the purchaser was notified that his/her order was processed.

Examples of Text Alerts Sent to Members of Patient's Care Group

Figure 23A:
FIGS. 23A-23C are screen diagrams illustrating examples of Short Message Service (SMS, or text) notifications and responsive communications received, by an individual member of a patient's care group, from a database server in an interactive notification system according to aspects of the present disclosure.
Figure 23B:
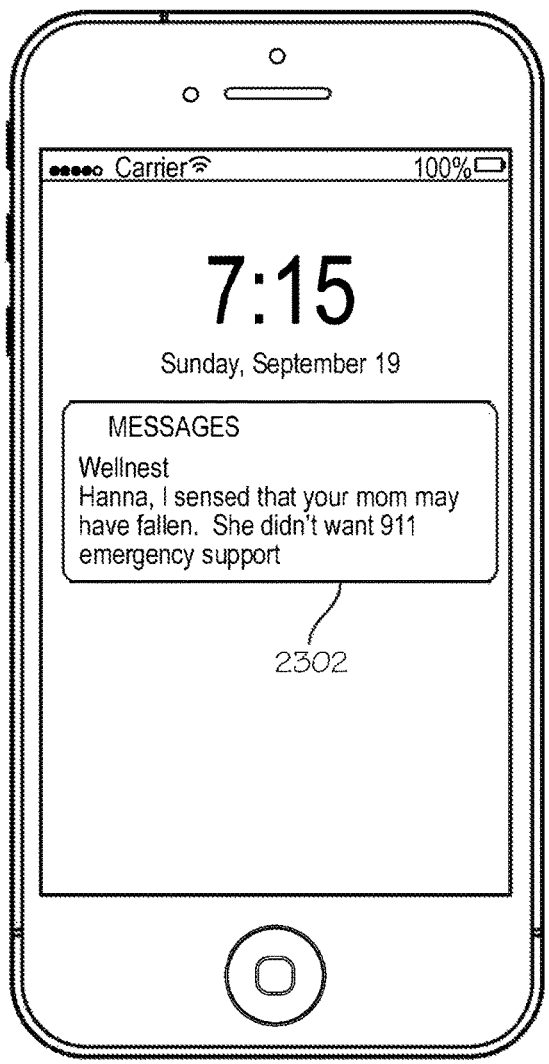
Figure 23C:
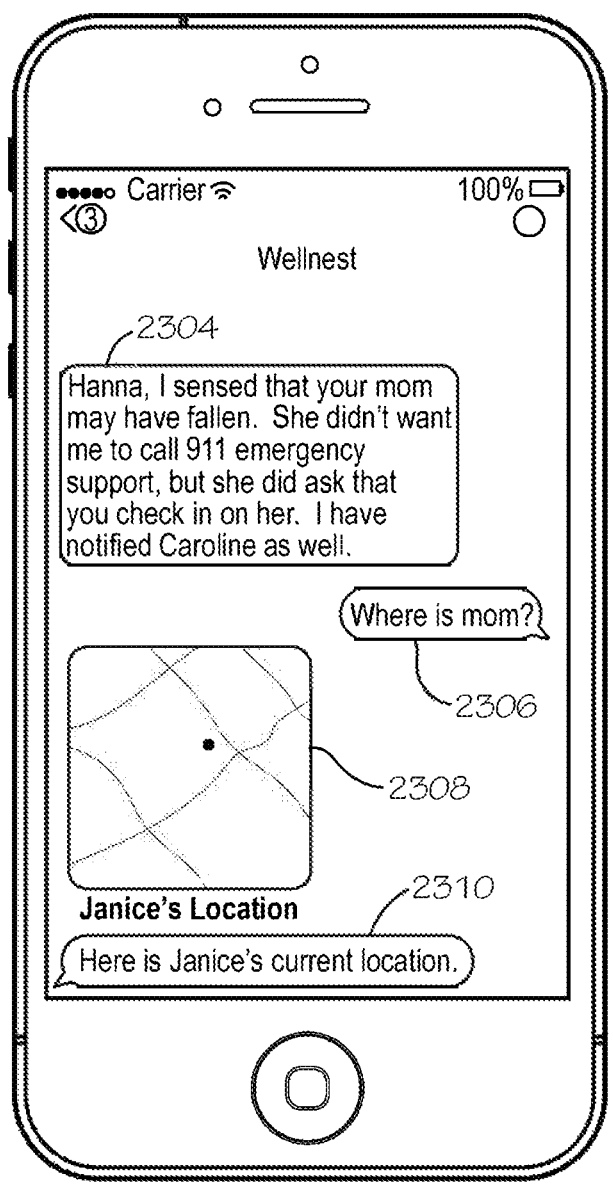

FIGS. 23A-23C are screen diagrams illustrating examples of SMS alerts and responsive communications received by an individual member of the patient's 102's care group 106, from the database server 124 in the interactive notification system 104 (FIG. 1). Using as an example the same names of Hanna and Janice that were used in the setup discussion of FIGS. 20A-20T, above, in FIG. 23A Hanna receives a text message 2300 from the database server 124 that Janice appears to have missed her evening medications. In FIG. 23B, Hanna receives a text message 2302 from the database server 124 comprising a different kind of alert, namely, an alert that Janice appeared to have fallen. However, based on Janice's verbal response to the wearable interactive notification device 100 that an e911 call was not needed, the verbal response having been processed by the voice recognition service 126 and sent to the database server 124 as text, the text message 2302 also indicates that Janice did not want 911 emergency support. In FIG. 23C, Hanna receives a text message 2304 from the database server 124 similar to text message 2302 in FIG. 23B, namely, that Janice fell, and that she did not want 911 assistance. This time, however, Janice asked her wearable interactive notification device 100 to have members in her care group 106 check on her, as in FIG. 13D, above. In this scenario, the "Caroline" referred to in the invitation during setup (FIG. 20Q) has now accepted the invitation and is a member of Janice's care group 106. Thus, the text message 2304 states that Caroline has also received a text notification of the reported incident. FIG. 23C demonstrates how the interactive notification system 104 allows Hanna to follow up with a text question, as at 2306, where Hanna asks the system 104 where Janice is located. The system 104, via the database server 124, recognizes the text in the question 2306 and interprets that text as a command to retrieve location data from the database 226, obtained by the database server 124 via the GNSS antenna 704 (FIG. 7A) of Janice's wearable interactive notification device 100. The system 104 responds with a map image 2308 pinpointing the location of Janice's device 100, and with a text message 2310 describing the image as "Janice's current location."

Figure 24:
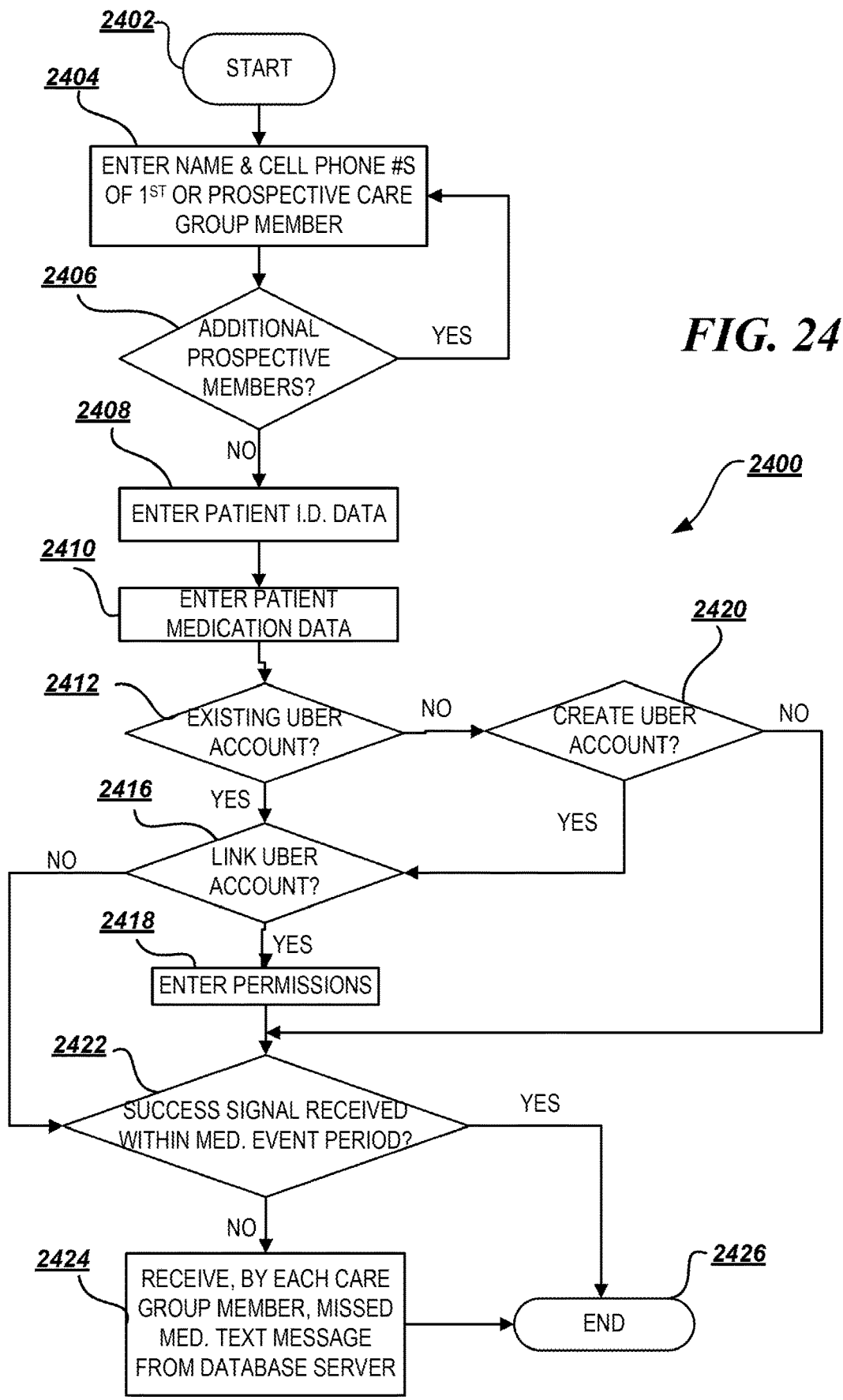
FIGS. 24 and 25 are flow charts illustrating an exemplary method for communicating an event concerning a patient to at least one other person, from the perspective of care group members and a database server, respectively, according to aspects of the present disclosure.
Figure 25:
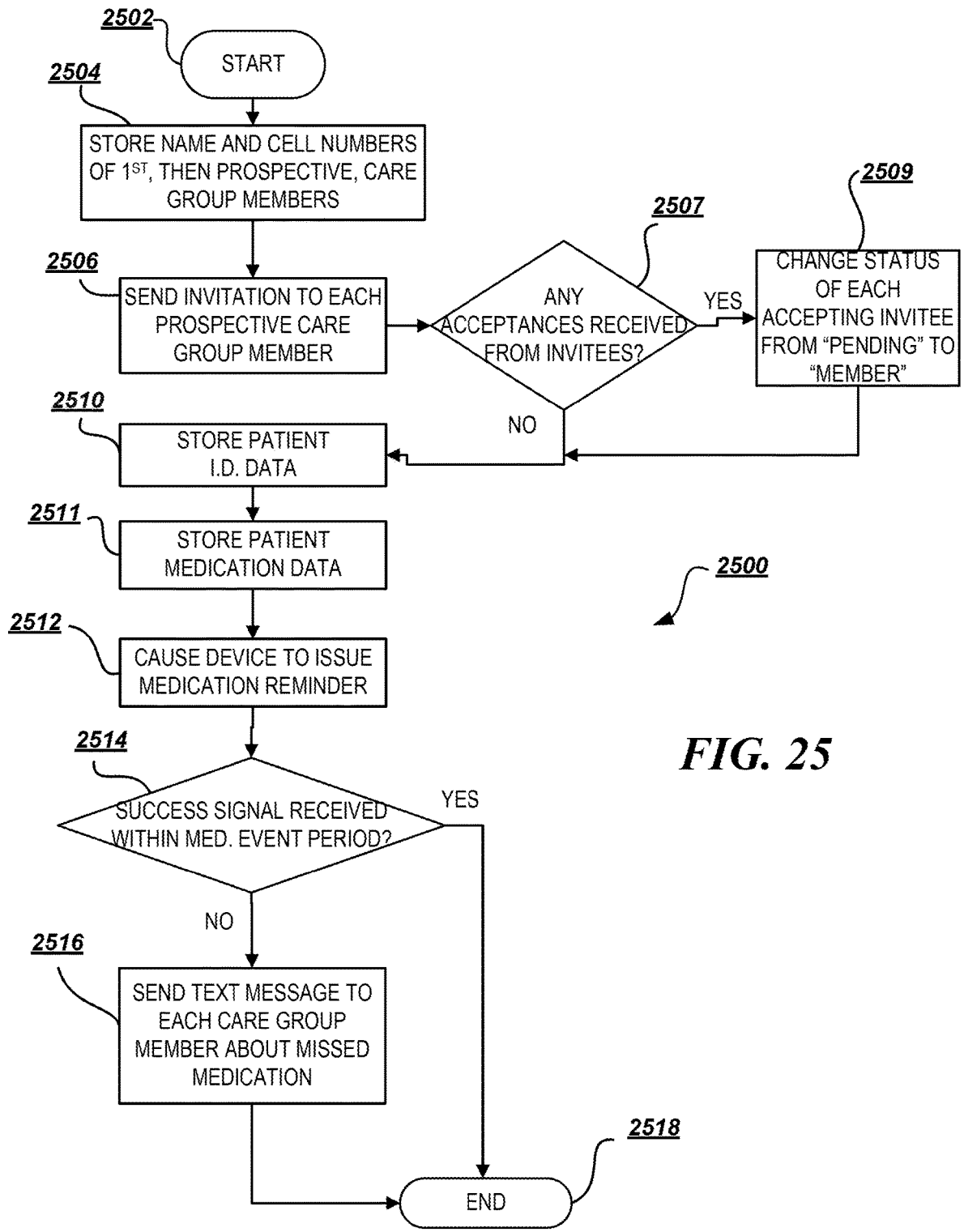

FIGS. 24 and 25 are flow charts illustrating an exemplary method for communicating an event concerning a patient to at least one other person, from the perspective of care group 106 members and a database server 124, respectively, according to aspects of the present disclosure, and tracing the steps discussed above with regard to the cell phone app and interfaces of FIGS. 20A-20T. Method 2400 starts at block 2402, and progresses to block 2404, where the first member of care group 106 (Hanna, in previous examples) enters her own name and cell phone number to begin the step of building a member list of at least one name, each name in the list identifying a person who has assented to become a member of a care group 106 for the patient 102. The member list is enhanced by considering the addition of other members at block 2406. If there are additional members to be considered, method 2400 loops back to block 2404, where the loop is repeated by Hanna who enters name and cell phone data for each prospective additional member of the care group 106. Referring to method 2500 of FIG. 25, such data thereby gets stored, at block 2504, in the database 226 within the database server 124. For each new name entered and for which Hanna clicked the SEND INVITATION button on a user interface discussed above, the database server 124, at block 2506, sends the text message invitation to the cell phone for each such new name. The database assigns a "pending" status to all invitees comprising prospective care group 106 members to whom an invitation has been sent but from whom an acceptance of the invitation has not yet been received. Method 2500 branches to block 2507, where it is ascertained whether any acceptance communications have been received from any invitees. If not, method 2500 proceeds to block 2510. If acceptances have been received, then the method instead branches to block 2509, where the database server 124 changes, at the database 226, the status of each accepting invitee from "pending" to "member," whereby the member will be designed by the database 226 to receive care group 106 communications from the database server 124. Once the database server has completed such membership updates, method 2500 proceeds from block 2509 to block 2510.

Referring again to FIG. 24, once all prospective new members have been invited, method 2400 advances to block 2408, where Hanna enters patient identification data, comprising at least a name of the patient 102 and a street address of the patient 102 (such information being stored in database 226 in method 2500, FIG. 25 at 2510). Next, at block 2410 of method 2400, Hanna enters patient medication data information into the database via her cellphone app, the patient medication information comprising at least, for each medication prescribed to the patient 102, a name of the medication, a dosage of the medication, a prescribed frequency for taking the medication, and at least one time of day for taking the medication. (In FIG. 25, at block 2511, the database server 124 stores the entered patient medication information into the database 226.) Next, starting with decision block 2412, Hanna can enter information regarding a taxi service such as Uber®, but at 2412, determination is first made as to whether she has an existing account. If so, method 2400 advances to decision block 2416, where Hanna decides whether to link her existing account to her member group 106 information. If so, method 2400 advances to block 2418, where Hanna enters her permissions (including whether they are denied) regarding access to certain information in her Uber® account, as discussed above. If, back at decision block 2412, Hanna does not have an Uber® account, method 2400 inquires, at decision block 2420, whether she would like to create an account. If so, the method 2400 branches to decision block 2416, described above. If not, method 2400 branches to decision block 2422. At decision block 2416, Hanna now decides whether she wants to link her Uber® account, in the manner previously described. If so, Method 2400 proceeds to block 2418, described above. If not, method 2400 skips to decision block 2422.

Referring to FIG. 25, at block 2512, the database server 124 causes the interactive notification device 100 designated for possession by the patient 102 to issue a medication reminder, the medication reminder comprising at least one of a visual reminder on a display of the device 100, a verbal reminder broadcast through a speaker 730 of the device 100, and a vibration reminder caused by activation of a vibration motor 714 in the device 100, the medication reminder issuing to the patient 102 upon an arrival of each time of day at which the patient 102 is scheduled to take a medication according to the patient medication information. Subsequent to initiation of the medication reminder to the patient 102, a medication event period is allowed to elapse, during which time the patient 102 is provided with the opportunity to take scheduled medication and send a success signal indicating that the patient consumed the scheduled medication. (This is done via either actuation of the button 710 during the medication event period, or a verbal command during that period, as discussed above). Method 2500 proceeds to decision block 2514, which asks the same question as decision block 2422 of FIG. 24, namely, whether the patient 102 sent a success signal within the mediation event period. If so, method 2500 ends at block 2518. If not, meaning that the medication event period elapsed without receipt by the database of a success signal, method 2500 proceeds to block 2516, where database server 124 sends text message to an entered cell phone number of each care group 106 member, the text message indicating that the patient 102 did not consume the scheduled medication during the medication event period. Method 2500 then ends at block 2518. The aforementioned text message is received by the care group members at block 2424 of FIG. 24, then the method 2400 similarly ends at block 2426.

Although several aspects have been disclosed in the foregoing specification, it is understood by those skilled in the art that many modifications and other aspects will come to mind to which this disclosure pertains, having the benefit of the teaching presented in the foregoing description and associated drawings. It is thus understood that the disclosure is not limited to the specific aspects disclosed hereinabove, and that many modifications and other aspects are intended to be included within the scope of any claims that can recite the disclosed subject matter.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, can be executed out of order from that shown or discussed, including substantially concurrently or in reverse order, depending on the functionality involved, as would be understood by those reasonably skilled in the art of the present disclosure. Many variations and modifications can be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A notification device, comprising:
at least one processor contained in a housing of the notification device, the housing configured for attachment to a user, and a portion of the housing comprising a display panel;
a voice translation service in communication with the at least one processor and at least one database server;
a speaker in communication with the voice translation service;
a button positioned beneath the display panel, the button being configured to be actuated during a medication event or outside of the mediation event in response to downward pressure by the user, and in response to actuation outside of the medication event, to open a channel of communication with the voice translation service in communication with the at least one processor;
an accelerometer within the housing of the notification device, the accelerometer being configured to detect a user free-fall condition outside of the medication event and, responsive to detection of the user free-fall condition, send an interrupt signal to the at least one processor;
at least one light-emitting diode (LED) in communication with the at least one processor, the LED being configured to backlight a device display beneath the display panel in response to a LED directive received by the at least one processor; and
a memory in communication with the at least one processor, the memory storing executable instructions for causing the at least one processor to provide a visual notification or reminder at the display panel responsive to a user free-fall condition detected by the accelerometer or a medication event in a medication schedule applicable to the user, wherein the visual notification or reminder causes at least one of the at least one LED to change its lighting state,
wherein the change of lighting state of the at least one LED comprises at least one of turning on from an off state, fading in from an off state, turning off from an on state, fading out from an on state, blinking, and pulsing; and
responsive to an interrupt signal from the accelerometer indicative of the user having fallen, cause to be broadcast by the speaker in the notification device a verbal statement in conjunction with the visual notification indicating that a countdown to an emergency 911 call is commencing, and reciting the countdown once the countdown is initiated; and responsive to a determination that the user did not instruct the notification device to stop prior to conclusion of the countdown, initiate the emergency 911 call on behalf of the user.

2. The notification device of claim 1, wherein the housing is wearable on a wrist of the user.

3. The notification device of claim 1, wherein the at least one LED is at least one selected from an icon LED and a ring LED, the icon LED being configured to backlight an icon on the device display, and the ring LED being configured to illuminate at least a portion of a ring-shaped path on the device display.

4. The notification device of claim 1, further comprising a vibration motor in communication with the at least one processor, wherein the memory stores further executable instructions for turning the vibration motor on from an off state during the medication event in the medication schedule applicable to the user.

5. The notification device of claim 1, further comprising:
an audio coder-decoder (CODEC) in communication with the at least one processor and the speaker,
wherein the memory further stores executable instructions for causing the at least one processor to broadcast through the speaker in the notification device a verbal medication reminder in conjunction with the visual reminder, the verbal medication reminder comprising an encoded voice signal comprising one of a streamed encoded voice signal from the voice translation service in communication with the processor and a stored encoded voice signal located in the memory.

6. The notification device of claim 5, further comprising:
a microphone in communication with the audio CODEC, the microphone configured to receive a voice command from the user, convert the voice command to a voice signal, and send the voice signal to the audio CODEC,
wherein the audio CODEC is configured to encode the voice signal to produce an encoded voice signal, and to transmit the encoded voice signal to the at least one processor;
wherein the memory further stores executable instructions for causing the at least one processor to transmit the encoded voice signal to the voice translation service in communication with the at least one database server; and
wherein the memory further stores executable instructions for causing the at least one processor to receive, from the voice translation service, a verbal response to the user's voice command, and to broadcast the response through the speaker.

7. The notification device of claim 6, wherein:
the audio CODEC comprises a plurality of inputs sharing a common connection to a bus, and
the at least one processor is further configured to selectively disable at least one of the speaker and the microphone responsive to a determination that the notification device is in an idle state.

8. The notification device of claim 1, wherein the button is a primary upper button, and further comprising a pair of side auxiliary buttons in communication with the at least one processor, the pair of side auxiliary buttons configured to, responsive to being pressed simultaneously, generate an interrupt signal, the interrupt signal configured to cause the at least one processor to send an emergency signal to the at least one database server in communication with the at least one processor.

9. The notification device of claim 8, wherein the interrupt signal is further configured to cause a modem in communication with the at least one processor to place an Enhanced 9-1-1 (E911) emergency call.

10. The notification device of claim 9, further comprising:
a radio frequency (RF) antenna in communication with the at least one processor, the RF antenna configured to wirelessly exchange communications with the at least one database server in communication with the at least one processor and the voice translation service in communication with the at least one database server; and
a Global Navigation Satellite System (GNSS) antenna in communication with the modem, the GNSS antenna configured to support at least a Global Positioning Satellite navigation system and to identify a contemporaneous geographic location of the notification device;
wherein the memory further stores executable instructions for causing the at least one processor to, when causing the at least one processor to send any emergency notification to the at least one database server, include the contemporaneous geographic location in the emergency notification.

11. The notification device of claim 10, further comprising:
a Bluetooth module in communication with the modem; and
a Bluetooth antenna in communication with the Bluetooth module, the Bluetooth antenna configured to wirelessly exchange communications with other Bluetooth-enabled devices.

12. The notification device of claim 1, wherein the interrupt signal is a first interrupt signal, and wherein the accelerometer is further configured to send a second interrupt signal to the at least one processor responsive to a single tap of the housing by the user.

13. The notification device of claim 12, wherein the memory further stores executable instructions for causing the at least one processor to, responsive to receipt of the second interrupt signal, send a communication to the at least one database server indicative of the user having taken a scheduled medication or the user instructing the notification device to stop prior to conclusion of the countdown to initiation of the emergency 911 call.

14. The notification device of claim 1, wherein the accelerometer is further configured to
count a number of steps taken by the user; and
responsive to an event comprising at least one of a verbal user request and engagement of the wearable interactive notification device with a docking station, send step count data indicating a counted number of steps to at least one of the docking station and the at least one database server.

15. A wireless notification system, comprising:
at least one database server, the at least one database server configured to store a medication schedule of a patient;
at least one voice translation service in communication with the at least one database server; and
a notification device comprising:
at least one processor configured to wirelessly communicate with the at least one database server and the at least one voice translation service, the at least one processor contained in a housing of the notification device, the housing configured for attachment to the patient, wherein a portion of the housing comprises a display panel;
an accelerometer within the housing of the notification device, the accelerometer being configured to detect a triggering event and to send an interrupt signal to the at least one processor upon detection of the triggering event, wherein the triggering event is an action detectable by the accelerometer selected from the notification device being taken out of a container in which it was shipped and the patient having fallen; and
a memory in communication with the at least one processor, wherein the memory stores executable instructions for causing the at least one processor to:
more than twice daily, and before the patient receives a shipment of the notification device, poll the at least one database server to ascertain whether any new data was entered in the at least one database server since a preceding act of polling by the at least one processor;
responsive to detecting that new data was entered into the at least one database server since the preceding act of polling by the at least one processor, ascertain whether the new data comprises at least one of purchaser information data and patient information data entered into the at least one database server by the purchaser entering the new data of the notification device;
responsive to receipt of the interrupt signal from the accelerometer indicative of the patient taking the notification device out of the container in which the notification device was shipped, cause the at least one database server to send to the voice translation service a personalized greeting in text form, the personalized greeting comprising a name of the purchaser and a name of the patient;
cause the voice translation service to translate the personalized greeting from text form into a verbal statement and to transmit a signal containing the verbal statement to the notification device, and causing the notification device to broadcast the verbal statement through a speaker in the notification device;
provide a visual reminder, at the display panel, of a medication event in the patient's medication schedule, transmit to the at least one voice translation service a voice signal corresponding to an utterance of the patient, and receive from the at least one voice translation service a verbal response to the utterance.

16. The wireless notification system of claim 15, wherein the memory stores executable instructions for causing the at least one processor to upon receipt of the interrupt signal from the accelerometer indicative of the patient having fallen, cause to be broadcasted to the speaker a verbal statement to the patient indicating that a countdown to an emergency 911 call is commencing, and initiating the countdown, and responsive to a determination that the patient did not instruct the notification device to stop prior to conclusion of the countdown, initiating the emergency 911 call on behalf of the patient.

17. The wireless notification system of claim 15, wherein the interrupt signal is a first interrupt signal, and wherein the accelerometer is further configured to send a second interrupt signal to the at least one processor responsive to a single tap of the housing of the notification device by the user.

18. The wireless notification system of claim 17, wherein the memory further stores executable instructions for causing the at least one processor to, responsive to receipt of the second interrupt signal, send a communication to the at least one database server indicative of the patient having instructed the notification device to stop prior to conclusion of the countdown to initiation of the emergency 911 call.

19. The wireless notification system of claim 15, wherein the notification device further comprises at least one light-emitting diode (LED) in communication with the at least one processor, the LED being configured to backlight a device display beneath the display panel in response to a LED directive received by the at least one processor; and wherein the memory further stores executable instructions for causing the at least one processor to provide a visual notification at the display panel responsive to receipt of the interrupt signal from the accelerometer, the visual notification causing at least one of the at least one LED to change its lighting state.

20. The wireless notification system of claim 15, further comprising:

an audio coder-decoder (CODEC) in communication with the at least one processor and the speaker, and wherein the memory stores executable instructions for causing the at least one processor to broadcast the verbal statement through the speaker in the notification device in conjunction with providing the visual notification at the display panel response to the user free-fall condition detected by the accelerometer, wherein the verbal statement comprises a voice signal comprising one of a streamed encoded voice signal from the voice translation service in communication with the processor and a stored encoded voice signal located in the memory.

* * * * *